(12) United States Patent
Rozzelle et al.

(10) Patent No.: US 8,318,469 B2
(45) Date of Patent: Nov. 27, 2012

(54) THERMUS BROCKIANUS NUCLEIC ACID POLYMERASES

(75) Inventors: James E. Rozzelle, San Francisco, CA (US); Elena V. Bolchakova, Union City, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 1284 days.

(21) Appl. No.: 11/300,194

(22) Filed: Dec. 13, 2005

(65) Prior Publication Data
US 2006/0141514 A1 Jun. 29, 2006

Related U.S. Application Data

(62) Division of application No. 10/302,817, filed on Nov. 22, 2000, now Pat. No. 7,052,877.

(60) Provisional application No. 60/334,434, filed on Nov. 30, 2001.

(51) Int. Cl.
*C12N 9/12* (2006.01)
*C12N 9/00* (2006.01)

(52) U.S. Cl. .................. 435/194; 435/183; 530/350

(58) Field of Classification Search ................. None
See application file for complete search history.

(56) References Cited

U.S. PATENT DOCUMENTS

| 5,474,920 A | 12/1995 | Moses |
|---|---|---|
| 5,541,311 A | 7/1996 | Dahlberg et al. |
| 6,875,573 B2 * | 4/2005 | Fuller et al. ............. 435/6 |

OTHER PUBLICATIONS

Ngo et al. In The Protein Folding Problem and Tertiary Structure Prediction, 1994, Merz et al. (ed.), Birkhauser, Boston, MA, pp. 433 and 492-495.*
C. Vieille et al., "Hyperthermophilic Enzymes: Sources, Uses, and Molecular Mechanisms for Thermostability" *Microbiology and Molecular Biology Reviews*, vol. 65, No. 1, Mar. 2001, pp. 1-43.
F. Lawyer et al., "Isolation, Characterization, and Expression in *Escherichia coli* of the DNA Polymerase Gene from *Thermus aquaticus*" The Journal of Biological Chemistry, vol. 264, No. 11, Apr. 15, 1989, pp. 6427-6437.
International Search Report dated Jun. 12, 2003 issued in PCT/US02/37657.

* cited by examiner

*Primary Examiner* — Richard Hutson

(57) ABSTRACT

The invention provides nucleic acids and polypeptides for nucleic acid polymerases from a thermophilic organism, *Thermus brockianus*. The invention also provides methods for using these nucleic acids and polypeptides.

6 Claims, 10 Drawing Sheets

```
2A2N:2161  ctcttcggccgcaggcgctacgt gccgacctcaacg ccggt aaagagcgtgcgggag
           |||||||||||||||||||||||      ||||||||| |||||      ||||||||||||
YS38:2161  ctcttcggccgcaggcgctacgt gccgacctcaacg ccggt aaagagcgtgcgggag     SEQ ID NO: 2
                                                                            SEQ ID NO: 1

2A2N:2221  gcggcggagcgcatgccctttaa catgccgtgcaggc cgcg ctgacctgatgaag
           |||||||||||||||||||||||     |||||||||| ||||      |||||||||||
YS38:2221  gcggcggagcgcatgccctttaa catgccgtgcaggc cgcg ctgacctgatgaag     SEQ ID NO: 2
                                                                            SEQ ID NO: 1

2A2N:2281  ctcgccatggtgaggctcttccct aggctccccag tt cccgaggatgtctcccag
           |||||||||||||||||||||||||     ||||||||| ||     |||||||||||||
YS38:2281  ctcgccatggtgaggctcttccct aggctccccag tt cccgaggatgtctcccag     SEQ ID NO: 2
                                                                            SEQ ID NO: 1

2A2N:2341  gtccacgacgagtcctcctggagg ccgagtgagc ggcgagcggcgg cctg
           ||||||||||||||||||||||||      |||||||||| |||||||||||||||
YS38:2341  gtccacgacgagtcctcctggagg ccgagtgagc ggcgagcggcgg cctg          SEQ ID NO: 2
                                                                            SEQ ID NO: 1

2A2N:2401  gccaaggaggtcatggagggagt ctggccctgcctggagtggaagtggc
           |||||||||||||||||||||||       |||||||||||||||||||||||
YS38:2401  gccaaggaggtcatggagggagt ctggccctgcctggagtggaagtggc            SEQ ID NO: 2
                                                                            SEQ ID NO: 1

2A2N:2461  atcggggaggactggctttccgccaagggctag 2493
           |||||||||||||||||||||||||||||||||
YS38:2461  atcggggaggactggctttccgccaagggctag 2493                        SEQ ID NO: 2
                                                                            SEQ ID NO: 1
```

FIG. 2A

|  |  | 1 |  |  |  |  | 50 |
|---|---|---|---|---|---|---|---|
| SEQ ID NO: 59 | Taq | MRGMLPLFEP | KGRVLLVDGH | HLAYRTFHAL | KGLTTSRGEP | VQAVYGFAKS |
| SEQ ID NO: 60 | Tth | MEAMLPLFEP | KGRVLLVDGH | HLAYRTFFAL | KGLTTSRGEP | VQAVYGFAKS |
| SEQ ID NO: 61 | Tfi | MTPLPLDLEEP | PKRVLLVDGH | HLAYRTFYAL | S.LTTSRGEP | VQMVYGFAKS |
| SEQ ID NO: 62 | Tfl | MAMLPLFEP | KGRVLLVDGH | HLAYRTFPAL | KGLTTSRGEP | VQAVYGFAKS |
| SEQ ID NO: 9 | Tbr YS38 | ...MLPLFEP | KGRVLLVDGH | HLAYRNFFAL | KGLTTSRGEP | VQGVYGFAKS |
| SEQ ID NO: 10 | Tbr 2AZN | ...MLPLFEP | KGRVLLVDGH | HLAYRMFFAL | KGLTTSRGEP | VQGVYGFAKS |

|  |  | 51 |  |  |  |  | 100 |
|---|---|---|---|---|---|---|---|
| SEQ ID NO: 59 | Taq | LLKALKEDG. | DAVIVVFDAK | APSFRHEAYG | GYRAGRAPTP | EDFPRQLALI |
| SEQ ID NO: 60 | Tth | LLKALKEDGY | KAVFVVFDAK | APSFRHEAYE | AYKAGRAPTP | EDFPRQLALI |
| SEQ ID NO: 61 | Tfi | LLKALKEDG. | QAVVVFDAK | APSFRHEAYE | AYKAGRAPTP | EDFPRQLALV |
| SEQ ID NO: 62 | Tfl | LLKALKEDG. | DVVVVFDAK | APSFRHEAYG | AYKAGRAPTP | EDFPRQLALI |
| SEQ ID NO: 9 | Tbr YS38 | LLKALKEDG. | DVVIVVFDAK | APSFRHEAYG | AYKAGRAPTP | EDFPRQLALI |
| SEQ ID NO: 10 | Tbr 2AZN | LLKALKEDG. | DVVIVVFDAK | APSFRHEAYG | AYKAGRAPTP | EDFPRQLALM |

|  |  | 101 |  |  |  |  | 150 |
|---|---|---|---|---|---|---|---|
| SEQ ID NO: 59 | Taq | KELVDLLGLA | RLEVPGYEAD | DVLASLAKKA | EREGYEVRIL | TADKDLYQLL |
| SEQ ID NO: 60 | Tth | KELVDLLGFT | RLEVPGYEAD | DVLATLAKKA | EREGYEVRIL | TADRDLYQLV |
| SEQ ID NO: 61 | Tfi | KELVDLLGLV | RLEAPGYEAD | DVLGTLAKKA | EREGMEVRIL | TCDRDFPQLL |
| SEQ ID NO: 62 | Tfl | KELVDLLGLE | RLEVPGFEAD | DVLATLAKKA | EREGYEVRIL | TADRDLYQLL |
| SEQ ID NO: 9 | Tbr YS38 | KELVDLLGLE | DVVIVVFGFEAD | DVLAALAKKA | EREGYEVRIL | TADRDLPQLL |
| SEQ ID NO: 10 | Tbr 2AZN | KELVDLLGLE | DVVIVVFGFEAD | DVLAALAKKA | EREGYEVRIL | TADRDLPQLL |

|  |  | 151 |  |  |  |  | 200 |
|---|---|---|---|---|---|---|---|
| SEQ ID NO: 59 | Taq | SDRIHVLHPE | GYLITPAWLW | EKYGLRPDQW | ADYRALTGDE | SDNLPGVKGI |
| SEQ ID NO: 60 | Tth | SDRVAVLHPE | GHLITPEWLW | EKYGLRPDQW | VDFRALVGDP | SDNLPGVKGI |
| SEQ ID NO: 61 | Tfi | SEKVSVLLPD | GTLVTPKDVQ | ERYGLVTPERW | ERYGVPPERW | SDNIPGVAGI |
| SEQ ID NO: 62 | Tfl | SERIAILHPE | GYLITPAKLY | EKYGLRPEQW | VDFRALTGDR | SDNIPGVKGI |
| SEQ ID NO: 9 | Tbr YS38 | SDRIAVLHPE | GHLITPQWLN | ERYGLRPEQW | VDYRALAGDP | SDNIPGVKGI |
| SEQ ID NO: 10 | Tbr 2AZN | SDRIAVLHPE | GHLITPQWLN | ERYGLRPEQW | VDFRALAGDP | SDNIPGVKGI |

```
                              401                                                                    450
SEQ ID NO: 59   Taq    EWTEEAGERA ALSERLFANL MGRLEGEERL LWLYREVERP LSRAVLAHMEA
SEQ ID NO: 60   Tth    EWTEDAAHRA LLSERLHRNL LKRLEGEERL LWLYREVERP LSRVLAHMEA
SEQ ID NO: 61   Tfi    EFTEDAAERA LLSERLFQHL FPRLS..EKL LWLYQEVERP LSRVLAHMEA
SEQ ID NO: 62   Tfl    EWTEDAGERA LLAERLFQTL KERLKGEERL LWLYEEVERP LSRVLAHMEA
SEQ ID NO: 9    Tbr YS38  EWTEEAGERA LLAERLYENL LSRLKGEERL LWLYEEVERP LSRVLAHMEA
SEQ ID NO: 10   Tbr 2A2N  EWTEEAGERA LLAERLYENL LSRLKGEERL LWLYREVERP LSRVLAHMEA 451                                                                    500
SEQ ID NO: 59   Taq    TGVRLDVAYL RALSLEVAEE IARLEAEVFR LAGHPFNLNS RDQLERVLFD
SEQ ID NO: 60   Tth    TGVRLDVAYL QALSLELAEE IRRLEEEVFR LAGHPFNLNS RDQLERVLFD
SEQ ID NO: 61   Tfi    RGVRLDVPLL EALSFELEKE MERLEGEVFR LAGHPFNLNS RDQLERVLPD
SEQ ID NO: 62   Tfl    TGVRLDVAYL QALSLEVAEE VRQLEEEVFR LAGHPFNLNS RDQLERVLFD
SEQ ID NO: 9    Tbr YS38  TGVRLDVPYL RALSLEVAAE MGRLEEEVFR LAGHPFNLNS RDQLERVLFD
SEQ ID NO: 10   Tbr 2A2N  TGVRLDVPYL RALSLEVAAE MGRLEEEVFR LAGHPFNLNS RDQLERVLFD 501                                                                    550
SEQ ID NO: 59   Taq    ELGLPAIGKT EKTGKRSTSA AVLEALREAH PIVEKILQYR ELTKLKSTYI
SEQ ID NO: 60   Tth    ELRLPALGKT QKTGKRSTSA AVLEALREAH PIVEKILQHR ELTKLKNTYV
SEQ ID NO: 61   Tfi    ELGLTPVGRT EKTGKRSTSA GALEALRGAH PIVELILQYR ELSKLKSTYL
SEQ ID NO: 62   Tfl    ELGLPAIGKT EKTGKRSTSA AVLEALREAH PIVDKILQYR ELTKLKNTYI
SEQ ID NO: 9    Tbr YS38  ELGLPPIGKT EKTGKRSTSA AVLEALREAH PIVEKILQYR ELAKLKGTYI
SEQ ID NO: 10   Tbr 2A2N  ELGLPPIGKT EKTGKRSTSA AVLEALRGAH PIVEKILQYR ELAKLKGTYI 551                                                                    600
SEQ ID NO: 59   Taq    DPLPDLIHPR TGRLHTRFNQ TATATGRLSS SDPNLQNIPV RTPLGQRIRR
SEQ ID NO: 60   Tth    DPLPSLVHPR TGRLHTRFNQ TATATGRLSS SDPNLQNIPV RTPLGQRIRR
SEQ ID NO: 61   Tfi    DPLPRLVHPR TGRLHTRFNQ TATATGRLSS SDPNLQNIPV RTPLGQRIRK
SEQ ID NO: 62   Tfl    DPLPALVHPR TGRLHTRFNQ TATATGRLSS SDPNLQNIPV RTPLGQRIRR
SEQ ID NO: 9    Tbr YS38  DLLPALVHPR TGRLHTRFNQ TATATGRLSS SDPNLQNIPV RTPLGQRIRR
SEQ ID NO: 10   Tbr 2A2N  DPLPALVHPR TGRLHTRFNQ TATATGRLSS SDPNLQNIPV RTPLGQRIRR
```

FIG. 2D

```
                                                                              650
                          601
Taq   SEQ ID NO: 59   AFIAEEGWLL VALDYSQIEL RVLAHLSGDE NLIRVFQEGR DIHTETASWM
Tth   SEQ ID NO: 60   AFVAEAGWAL VALDYSQIEL RVLAHLSGDE NLIRVFQEGK DIHTQTASWM
Tfi   SEQ ID NO: 61   LAADYSQIEL LAADYSQIEL RVLAHLSGDE NLKRVFREGK DIHTETAAWM
Tfl   SEQ ID NO: 62   AFVAEEGWLL VVLDYSQIEL RVLAHLSGDE NLIRVFQEGR DIHTQTASWM
Tbr   SEQ ID NO: 9    AFVAEEGYLL VALDYSQIEL RVLAHLSGDE NLIRVFQEGR DIHTQTASWM
Tbr 2A2N SEQ ID NO: 10 AFVAEEGYLL VALDYSQIEL RVLAHLSGDE NLIRVFQEGR DIHTQTASWM 651                                                700
Taq   SEQ ID NO: 59   FGVPREAVDP LMRRAAKTIN FGVLYGMSAH RLSQELAIPY EEAQAFIERY
Tth   SEQ ID NO: 60   FGVPPEAVDP LMRRAAKTVN FGVLYGMSAH RLSQELAIPY EEAVAFIERY
Tfi   SEQ ID NO: 61   FGLDPALVDP KMRRAAKTIN FGVLYGMSAH RLSQELGIDY KEAEAFIERY
Tfl   SEQ ID NO: 62   FGVSPEGVDP LMRRAAKTIN FGVLYGMSAH RLSGELSIPY EEAVAFIERY
Tbr   SEQ ID NO: 9    FGLPAEAIDP LRRRAAKTIN FGVLYGMSAH RLSQELGIPY EEAVAFIDRY
Tbr 2A2N SEQ ID NO: 10 FGLPAEAIDP LRRRAAKTIN FGVLYGMSAH RLSQELGIPY EEAVAFIDRY 701                                                750
Taq   SEQ ID NO: 59   FQSFPKVRAW IEKTLEEGRM RGYVETLFGR RRYVPDLEAR VKSVREAAER
Tth   SEQ ID NO: 60   FQSFPKVRAW IEKTLEEGRM RGYVETLFGR RRYVPDLNAR VKSVREAAER
Tfi   SEQ ID NO: 61   FQSFPKVRAW IERTLEEGRT RGYVETLFGR RRYVPDLASR VRSVREAAER
Tfl   SEQ ID NO: 62   FQSFPKVRAW IEGTLEEGRR RGYVETLFGR RRYVPDLNAR RVSVREAAER
Tbr   SEQ ID NO: 9    FQSYPKVRAW IERTLEEGRQ RGYVETLFGR RRYVPDLEAR VKSVREAAER
Tbr 2A2N SEQ ID NO: 10 FQSYPKVRAW IERTLEEGRQ RGYVETLFGR RRYVPDLEAR VKSVREAAER 751                                                800
Taq   SEQ ID NO: 59   MAFNMPVQGT AADLMKLAMV KLFPRLEEMG ARMLLQVHDE LVLEAPKERA
Tth   SEQ ID NO: 60   MAFNMPVQGT AADLMKLAMV KLFPRLEEMG ARMLLQVHDE LLLEAPQARA
Tfi   SEQ ID NO: 61   MAFNMPVQGT AADLMKRAMV RLFPRLKPLG AMLLLQVHDE LVLEVPEDRA
Tfl   SEQ ID NO: 62   MAFNMPVQGT AADLMKLAMV RLFPRLQELG ARMLLQVHDE LVLEAPEDRA
Tbr   SEQ ID NO: 9    MAFNMPVQGT AADLMKLAMV RLFPRLPEWG ARMLLQVHDE LLLEAPKERA
Tbr 2A2N SEQ ID NO: 10 MAFNMPVQGT AADLMKLAMV RLFPRLPEVG ARMLLQVHDE LLLEAPKERA
```

FIG. 2E

```
                              801                                              837
SEQ ID NO: 59  Taq         EAVARLAKEV  MEGVYPLAVP  LEVEVGIGED  WLSAKE.
SEQ ID NO: 60  Tth         EEVAALAKEA  MEKAYPLAVP  LEVEVGMGED  WLSAKG.
SEQ ID NO: 61  Tfi         EEAKALVKEV  MEDNAYPLDVP LEVEVGVGRD  WLEAKQD
SEQ ID NO: 62  Tfl         ERVAALAKEV  MEGVWPLQVP  LEVEVGLGED  WLSAKE.
SEQ ID NO: 9   Tbr  YS38   EEAAALAKEV  MEGVWPLAVP  LEVEVGIGED  WLSAKG.
SEQ ID NO: 10  Tbr  2AZN   EEAAALAKEV  MEGVWPLAVP  LEVEVGIGED  WLSAKG.
```

THERMUS BROCKIANUS NUCLEIC ACID POLYMERASES

CROSS REFERENCE TO RELATED APPLICATIONS

This application is a Divisional Application of U.S. Non-Provisional application Ser. No. 10/302,817, filed Nov. 22, 2002, now U.S. Pat. No. 7,052,877, which claims a priority benefit under 35 U.S.C. §119(e) from U.S. Patent Application No. 60/334,434, filed Nov. 30, 2001, and which is incorporated herein by reference.

FIELD OF THE INVENTION

The invention relates to nucleic acids and polypeptides for a nucleic acid polymerase isolated from a thermophilic organism, Thermus brockianus.

BACKGROUND OF THE INVENTION

DNA polymerases are naturally-occurring intracellular enzymes used by a cell for replicating DNA by reading one nucleic acid strand and manufacturing its complement. Enzymes having DNA polymerase activity catalyze the formation of a bond between the 3' hydroxyl group at the growing end of a nucleic acid primer and the 5' phosphate group of a newly added nucleotide triphosphate. Nucleotide triphosphates used for DNA synthesis are usually deoxyadenosine triphosphate (A), deoxythymidine triphosphate (T), deoxycytosine triphosphate (C) and deoxyguanosine triphosphate (G), but modified or altered versions of these nucleotides can also be used. The order in which the nucleotides are added is dictated by hydrogen-bond formation between A and T nucleotide bases and between G and C nucleotide bases.

Bacterial cells contain three types of DNA polymerases, termed polymerase I, II and III. DNA polymerase I is the most abundant polymerase and is generally responsible for certain types of DNA repair, including a repair-like reaction that permits the joining of Okazaki fragments during DNA replication. Pol I is essential for the repair of DNA damage induced by UV irradiation and radiomimetic drugs. Pol II is thought to play a role in repairing DNA damage that induces the SOS response. In mutants that lack both pol I and III, pol II repairs UV-induced lesions. Pol I and II are monomeric polymerases while pol III is a multisubunit complex.

Enzymes having DNA polymerase activity are often used in vitro for a variety of biochemical applications including cDNA synthesis and DNA sequencing reactions. See Sambrook e al., Molecular Cloning: A Laboratory Manual (3rd ed. Cold Spring Harbor Laboratory Press, 2001, hereby incorporated by reference. DNA polymerases are also used for amplification of nucleic acids by methods such as the polymerase chain reaction (PCR) (Mullis et al., U.S. Pat. Nos. 4,683,195, 4,683,202, and 4,800,159, incorporated by reference) and RNA transcription-mediated amplification methods (e.g., Kacian et al., PCT Publication No. WO91/01384, incorporated by reference).

DNA amplification utilizes cycles of primer extension through the use of a DNA polymerase activity, followed by thermal denaturation of the resulting double-stranded nucleic acid in order to provide a new template for another round of primer annealing and extension. Because the high temperatures necessary for strand denaturation result in the irreversible inactivations of many DNA polymerases, the discovery and use of DNA polymerases able to remain active at temperatures above about 37° C. provides an advantage in cost and labor efficiency.

Thermostable DNA polymerases have been discovered in a number of thermophilic organisms including Thermus aquaticus, Thermus thermophilus, and species within the genera the Bacillus, Thermococcus, Sulfobus, and Pyrococcus. A full length thermostable DNA polymerase derived from Thermus aquaticus (Taq) has been described by Lawyer, et al., J. Biol. Chem. 264:6427-6437 (1989) and Gelfand et al, U.S. Pat. No. 5,466,591. The cloning and expression of truncated versions of that DNA polymerase are further described in Lawyer et al., in PCR Methods and Applications, 2:275-287 (1993), and Barnes, PCT Publication No. WO92/06188 (1992). Sullivan reports the cloning of a mutated version of the Taq DNA polymerase in EPO Publication No. 0482714A1 (1992). A DNA polymerase from Thermus thermophilus has also been cloned and expressed. Asakura et al., J. Ferment. Bioeng. (Japan), 74:265-269 (1993). However, the properties of the various DNA polymerases vary. Accordingly, new DNA polymerases are needed that have improved sequence discrimination, better salt tolerance, varying degrees of thermostability, improved tolerance for labeled or dideoxy nucleotides and other valuable properties.

SUMMARY OF THE INVENTION

The invention provides nucleic acid polymerases isolated from a thermophilic organism, Thermus brockianus, for example, from strains YS38 and 2AZN.

In one embodiment, the invention provides an isolated nucleic acid comprising SEQ ID NO:1, SEQ ID NO:2, SEQ ID NO:3, or SEQ ID NO:4, SEQ ID NO:5, SEQ ID NO:6, SEQ ID NO:7 or SEQ ID NO:8, and complementary nucleic acids. In another embodiment, the invention provides an isolated nucleic acid encoding a polypeptide comprising an amino acid sequence that has at least 96% identity to SEQ ID NO:9, SEQ ID NO:10, SEQ ID NO:11, SEQ ID NO:12, SEQ ID NO:13, SEQ ID NO:14, SEQ ID NO:15 or SEQ ID NO:16. The invention also provides vectors comprising these isolated nucleic acids, including expression vectors comprising a promoter operably linked to these isolated nucleic acids. Host cells comprising such isolated nucleic acids and vectors are also provided by the invention, particularly host cells capable of expressing a thermostable polypeptide encoded by the nucleic acid, where the polypeptide has DNA polymerase activity.

The invention also provides isolated polypeptides that can include amino acid sequence comprising any one of SEQ ID NO:9-50. The isolated polypeptides provided by the invention preferably are thermostable and have a DNA polymerase activity between 50,000 U/mg protein and 500,000 U/mg protein.

The invention further provides a method of synthesizing DNA that includes contacting a polypeptide comprising SEQ ID NO:9, SEQ ID NO:10, SEQ ID NO:11, SEQ ID NO:12, SEQ ID NO:13, SEQ ID NO:14, SEQ ID NO:15 or SEQ ID NO:16 with a DNA under conditions sufficient to permit polymerization of DNA.

The invention further provides a method for thermocyclic amplification of nucleic acid that comprises contacting a nucleic acid with a thermostable polypeptide having SEQ ID NO:9, SEQ ID NO:10, SEQ ID NO:11, SEQ ID NO:12, SEQ ID NO:13, SEQ ID NO:14, SEQ ID NO:15 or SEQ ID NO:16 under conditions suitable for amplification of the nucleic acid, and amplifying the nucleic acid. In general, one or more primers are included in the amplication mixture, where each primer can hybridize to a separate segment of the nucleic acid. Such amplification can include cycling the temperature to permit denaturation of nucleic acids, annealing of a primer to a template nucleic acid and polymerization of a nucleic acid complementary to the template nucleic acid. Amplification can be, for example, by Strand Displacement Amplification or Polymerase Chain Reaction.

The invention also provides a method of primer extending DNA comprising contacting a polypeptide comprising SEQ ID NO:9, SEQ ID NO:10, SEQ ID NO:11, SEQ ID NO:12, SEQ ID NO:13, SEQ ID NO:14, SEQ ID NO:15 or SEQ ID NO:16 with a DNA and a primer capable of hybridizing to a segment of the DNA under conditions sufficient to permit polymerization of DNA. Such primer extension can be performed, for example, to sequence DNA or to amplify DNA.

The invention further provides a method of making a DNA polymerase comprising SEQ ID NO:9, SEQ ID NO:10, SEQ ID NO:11, SEQ ID NO:12, SEQ ID NO:13, SEQ ID NO:14, SEQ ID NO:15 or SEQ ID NO:16. The method comprises incubating a host cell under conditions sufficient for RNA transcription and translation, wherein the host cell comprises a nucleic acid that encodes a polypeptide comprising SEQ ID NO:9, SEQ ID NO:10, SEQ ID NO:11, SEQ ID NO:12, SEQ ID NO:13, SEQ ID NO:14, SEQ ID NO:15 or SEQ ID NO:16 operably linked to a promoter. In one embodiment, the method uses a nucleic acid that comprises SEQ ID NO:1, SEQ ID NO:2, SEQ ID NO:3, SEQ ID NO:4, SEQ ID NO:5, SEQ ID NO:6, SEQ ID NO:7 or SEQ ID NO:8. The invention is also directed to a DNA polymerase made by this method.

The invention also provides a kit that includes a container containing a DNA polymerase that has an amino acid sequence comprising SEQ ID NO:9, SEQ ID NO:10, SEQ ID NO:11, SEQ ID NO:12, SEQ ID NO:13, SEQ ID NO:14, SEQ ID NO:15 or SEQ ID NO:16. The kit can also contain an unlabeled nucleotide, a labeled nucleotide, a balanced mixture of nucleotides, a chain terminating nucleotide, a nucleotide analog, a buffer solution, a solution containing magnesium, a cloning vector, a restriction endonuclease, a sequencing primer, a solution containing reverse transcriptase, or a DNA or RNA amplification primer. Such kits can, for example, be adapted for performing DNA sequencing, DNA amplification, RNA amplification or primer extension reactions.

DESCRIPTION OF THE FIGURE

Figure 1A:
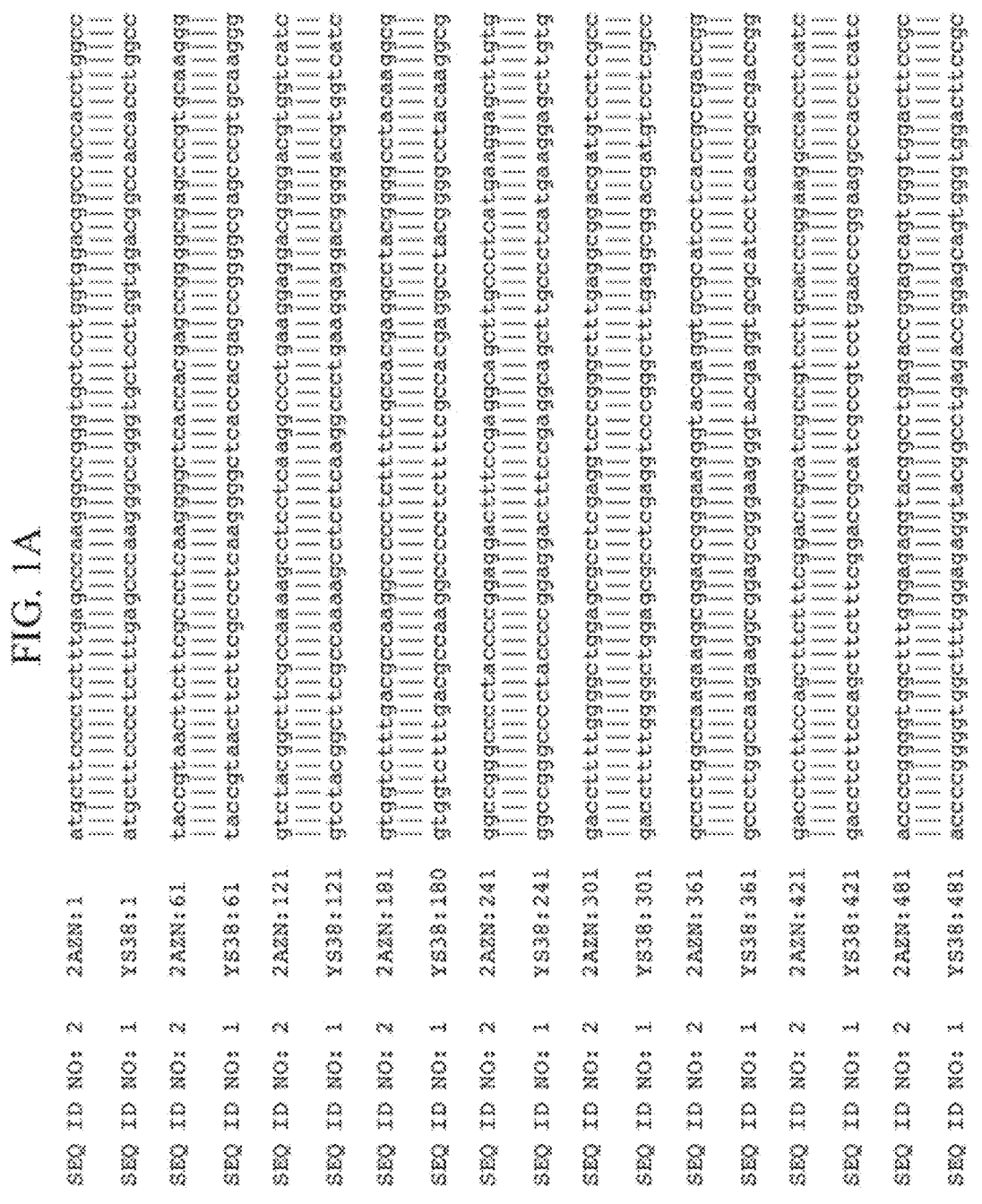
Figure 1B:
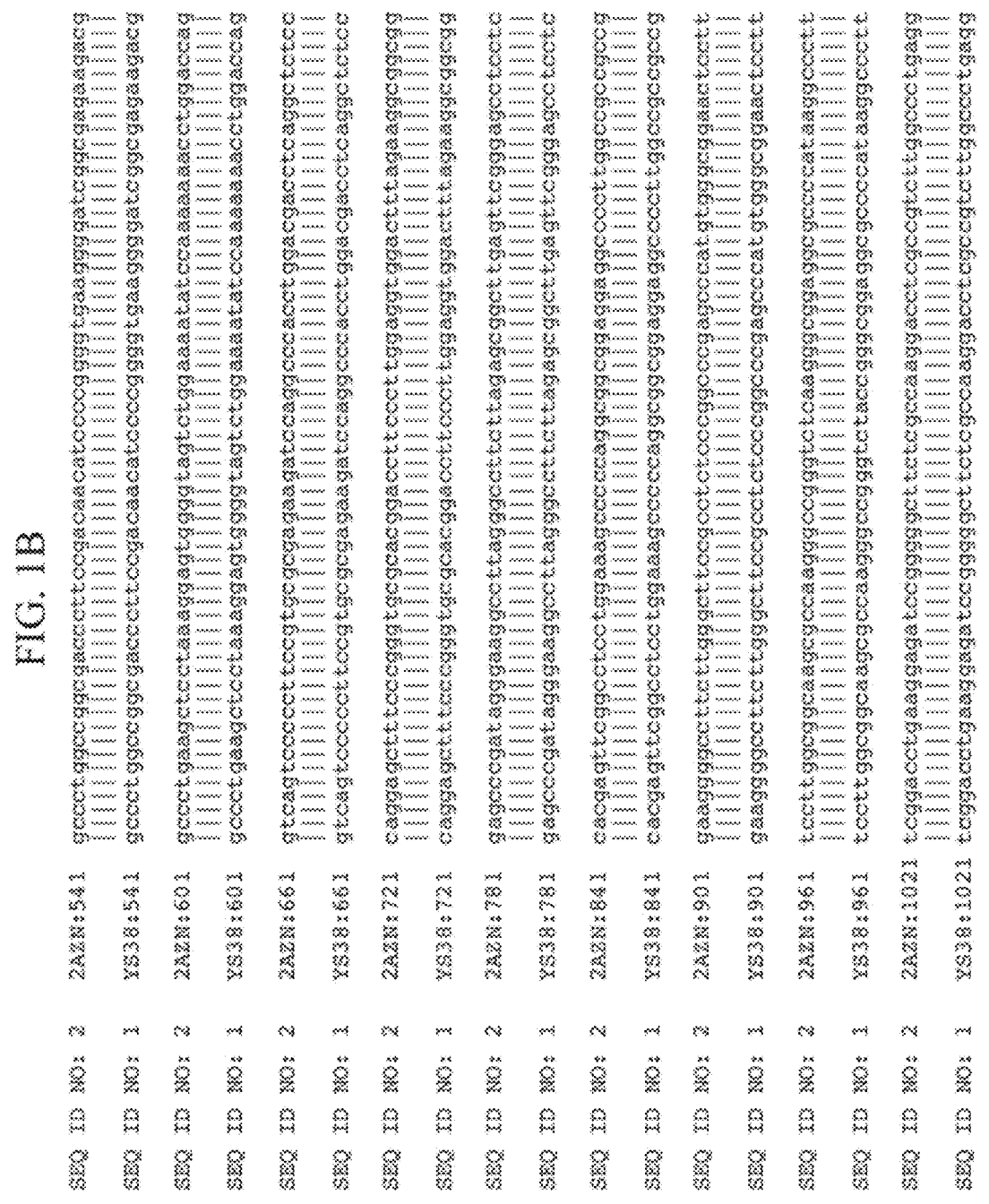
Figure 1C:
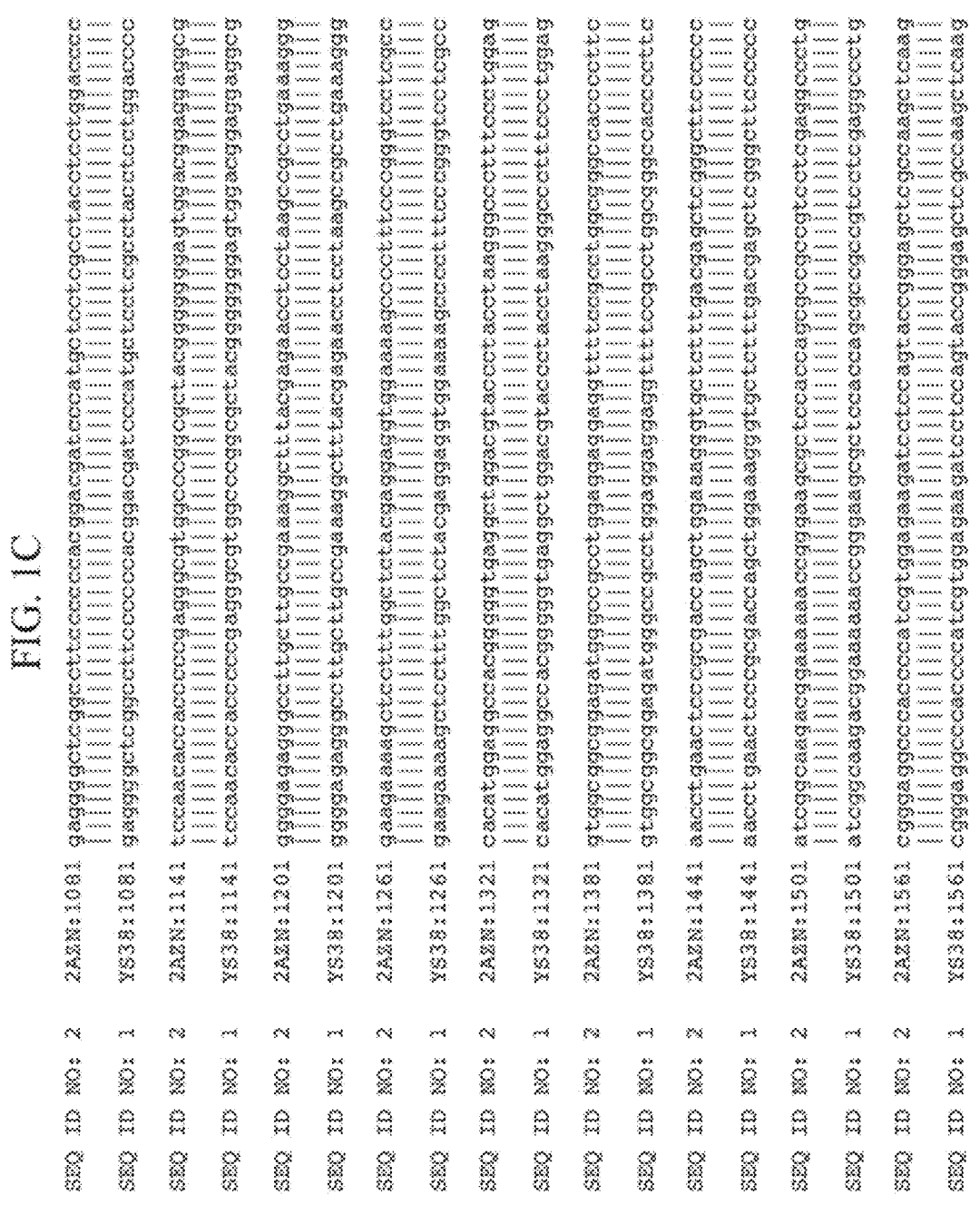
Figure 1D:
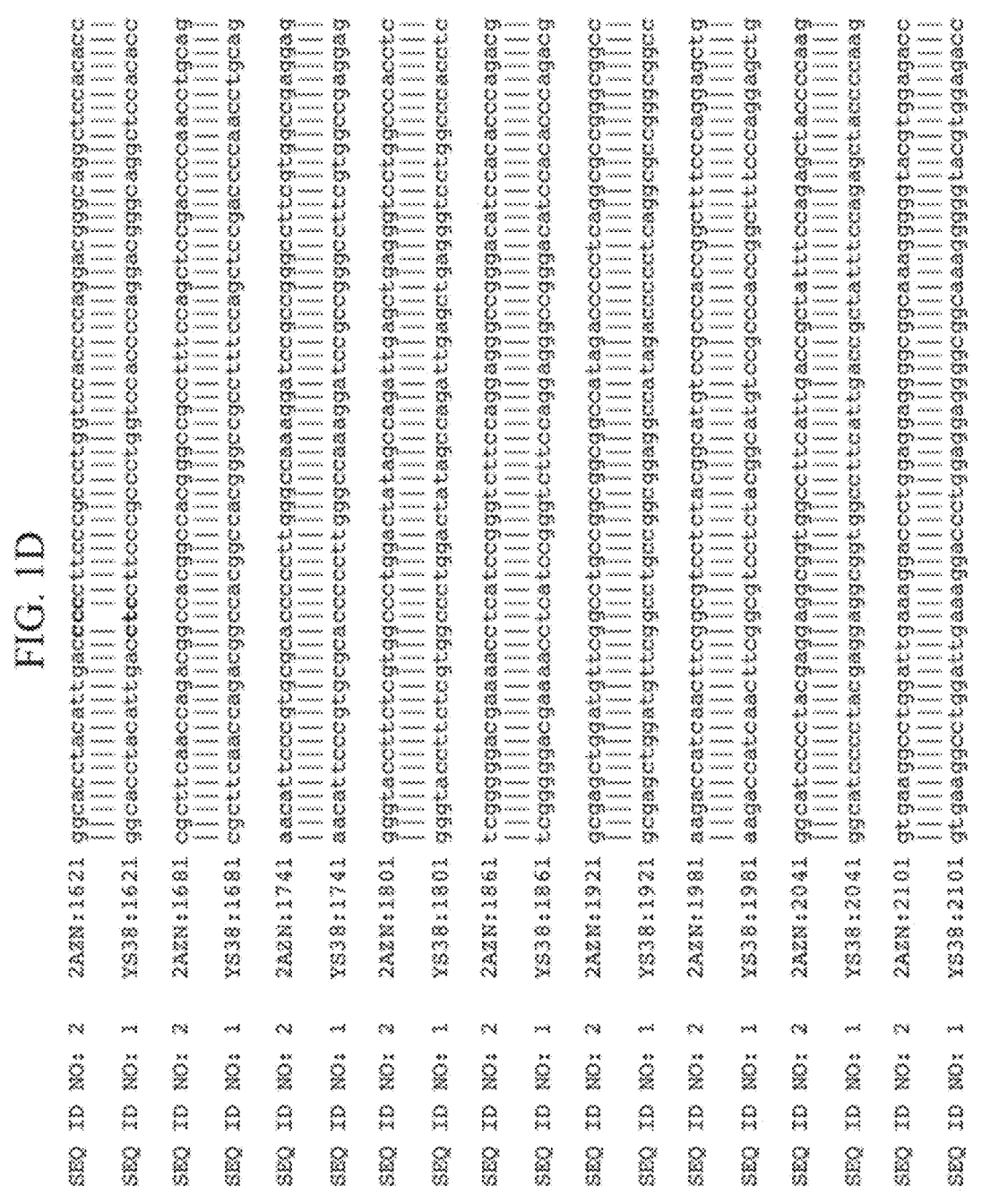

FIG. 1 provides an alignment of nucleic acid polymerase nucleic acids from Thermus brockianus strains 2AZN (SEQ ID NO:2) and YS38 (SEQ ID NO:1). Two codon differences exist between these strains. One is silent and the other is a difference of C vs T at position 1637 (indicated in boldface), encoding a difference of leucine vs proline at amino acid position 546.

FIG. 2 provides a comparison of amino acid sequences for polymerases from Thermus aquaticus (Taq, SEQ ID NO:59), Thermus thermophilus (Tth, SEQ ID NO:60), Thermus filiformis (Tfi, SEQ ID NO:61), Thermus flavus (Tfl, SEQ ID NO:62), Thermus brockianus strain YS38 (TbrYS38, SEQ ID NO:9) and Thermus brockianus strain 2AZN (Tbr 2AZN, SEQ ID NO:10).

DETAILED DESCRIPTION OF THE INVENTION

The present invention relates to nucleic acid and amino acid sequences encoding nucleic acid polymerases from thermophilic organisms. In particular, the present invention provides nucleic acid polymerases from Thermus brockianus. The nucleic acid polymerases of the invention can be used in a variety of procedures, including DNA primer extension, DNA sequencing, reverse transcription and DNA amplification procedures.

DEFINITIONS

The term "amino acid sequence" refers to the positional arrangement and identity of amino acids in a peptide, polypeptide or protein molecule. Use of the term "amino acid sequence" is not meant to limit the amino acid sequence to the complete, native amino acid sequence of a peptide, polypeptide or protein.

"Chimeric" is used to indicate that a DNA sequence, such as a vector or a gene, is comprised of more than one DNA sequence of distinct origin that is fused by recombinant DNA techniques to another DNA sequence, resulting in a longer DNA sequence that does not occur naturally.

The term "coding region" refers to the nucleic acid segment that codes for a protein of interest. The coding region of a protein is bounded on the 5' side by the nucleotide triplet "ATG" that encodes the initiator methionine and on the 3' side by one of the three triplets that specify stop codons (i.e., TAA, TAG, TGA).

"Constitutive expression" refers to expression using a constitutive promoter.

"Constitutive promoter" refers to a promoter that is able to express the gene that it controls in all, or nearly all, phases of the life cycle of the cell.

"Complementary" or "complementarity" are used to define the degree of base-pairing or hybridization between nucleic acids. For example, as is known to one of skill in the art, adenine (A) can form hydrogen bonds or base pair with thymine (T) and guanine (G) can form hydrogen bonds or base pair with cytosine (C). Hence, A is complementary to T while G is complementary to C. Complementarity may be complete when all bases in a double-stranded nucleic acid are base paired. Alternatively, complementarity may be "partial," when only some of the bases in a nucleic acid are matched according to the base pairing rules. The degree of complementarity between nucleic acid strands has an effect on the efficiency and strength of hybridization between nucleic acid strands.

The "derivative" of a reference nucleic acid, protein, polypeptide or peptide, is a nucleic acid, protein, polypeptide or peptide, respectively, with a related but different sequence or chemical structure than the respective reference nucleic acid, protein, polypeptide or peptide. A derivative nucleic acid, protein, polypeptide or peptide is generally made purposefully to enhance or incorporate some chemical, physical or functional property that is absent or only weakly present in the reference nucleic acid, protein, polypeptide or peptide. A derivative nucleic acid generally can differ in nucleotide sequence from a reference nucleic acid whereas a derivative protein, polypeptide or peptide can differ in amino acid sequence from the reference protein, polypeptide or peptide, respectively. Such sequence differences can be one or more substitutions, insertions, additions, deletions, fusions and truncations, which can be present in any combination. Differences can be minor (e.g., a difference of one nucleotide or amino acid) or more substantial. However, the sequence of the derivative is not so different from the reference that one of skill in the art would not recognize that the derivative and reference are related in structure and/or function. Generally, differences are limited so that the reference and the derivative are closely similar overall and, in many regions, identical. A "variant" differs from a "derivative" nucleic acid, protein, polypeptide or peptide in that the variant can have silent structural differences that do not significantly change the chemical, physical or functional properties of the reference nucleic acid, protein, polypeptide or peptide. In contrast, the differences between the reference and derivative nucleic acid, protein, polypeptide or peptide are intentional changes made to improve one or more chemical, physical or functional properties of the reference nucleic acid, protein, polypeptide or peptide.

The terms "DNA polymerase activity," "synthetic activity" and "polymerase activity" are used interchangeably and refer to the ability of an enzyme to synthesize new DNA strands by the incorporation of deoxynucleoside triphosphates. A protein that can direct the synthesis of new DNA strands by the incorporation of deoxynucleoside triphosphates in a template-dependent manner is said to be "capable of DNA synthetic activity."

The term "5' exonuclease activity" refers to the presence of an activity in a protein that is capable of removing nucleotides from the 5' end of a nucleic acid.

The term "3' exonuclease activity" refers to the presence of an activity in a protein that is capable of removing nucleotides from the 3' end of a nucleic acid.

"Expression" refers to the transcription and/or translation of an endogenous or exogeneous gene in an organism. Expression generally refers to the transcription and stable accumulation of mRNA. Expression may also refer to the production of protein.

"Expression cassette" means a nucleic acid sequence capable of directing expression of a particular nucleotide sequence. Expression cassettes generally comprise a promoter operably linked to the nucleotide sequence to be expressed (e.g., a coding region) that is operably linked to termination signals. Expression cassettes also typically comprise sequences required for proper translation of the nucleotide sequence. The expression cassette comprising the nucleotide sequence of interest may be chimeric, meaning that at least one of its components is heterologous with respect to at least one of its other components. The expression of the nucleotide sequence in the expression cassette may be under the control of a constitutive promoter or under control of an inducible promoter that initiates transcription only when the host cell is exposed to some particular external stimulus. In the case of a multicellular organism, the promoter can also be specific to a particular tissue or organ or stage of development.

The term "gene" is used broadly to refer to any segment of nucleic acid associated with a biological function. The term "gene" encompasses the coding region of a protein, polypeptide, peptide or structural RNA. The term "gene" also includes sequences up to a distance of about 2 kb on either end of a coding region. These sequences are referred to as "flanking" sequences or regions (these flanking sequences are located 5' or 3' to the non-translated sequences present on the mRNA transcript). The 5' flanking region may contain regulatory sequences such as promoters and enhancers or other recognition or binding sequences for proteins that control or influence the transcription of the gene. The 3' flanking region may contain sequences that direct the termination of transcription, post-transcriptional cleavage and polyadenylation as well as recognition sequences for other proteins. A protein or polypeptide encoded in a gene can be full length or any portion thereof, so that all activities or functional properties are retained, or so that only selected activities (e.g., enzymatic activity, ligand binding, or signal transduction) of the full-length protein or polypeptide are retained. The protein or polypeptide can include any sequences necessary for the production of a proprotein or precursor polypeptide. The term "native gene" refers to gene that is naturally present in the genome of an untransformed cell.

"Genome" refers to the complete genetic material that is naturally present in an organism and is transmitted from one generation to the next.

The terms "heterologous nucleic acid," or "exogenous nucleic acid" refer to a nucleic acid that originates from a source foreign to the particular host cell or, if from the same source, is modified from its original form. Thus, a heterologous gene in a host cell includes a gene that is endogenous to the particular host cell but has been modified through, for example, the use of DNA shuffling. The terms also include non-naturally occurring multiple copies of a naturally occurring nucleic acid. Thus, the terms refer to a nucleic acid segment that is foreign or heterologous to the cell, or normally found within the cell but in a position within the cell or genome where it is not ordinarily found.

The term "homology" refers to a degree of similarity between a nucleic acid and a reference nucleic acid or between a polypeptide and a reference polypeptide. Homology may be partial or complete. Complete homology indicates that the nucleic acid or amino acid sequences are identical. A partially homologous nucleic acid or amino acid sequence is one that is not identical to the reference nucleic acid or amino acid sequence. Hence, a partially homologous nucleic acid has one or more nucleotide differences in its sequence relative to the nucleic acid to which it is being compared. The degree of homology can be determined by sequence comparison. Alternatively, as is well understood by those skilled in the art, DNA-DNA or DNA-RNA hybridization, under various hybridization conditions, can provide an estimate of the degree of homology between nucleic acids, (see, e.g., Haines and Higgins (eds.), Nucleic Acid Hybridization, IRL Press, Oxford, U.K.).

"Hybridization" refers to the process of annealing complementary nucleic acid strands by forming hydrogen bonds between nucleotide bases on the complementary nucleic acid strands. Hybridization, and the strength of the association between the nucleic acids, is impacted by such factors as the degree of complementary between the hybridizing nucleic acids, the stringency of the conditions involved, the Tm of the formed hybrid, and the G:C ratio within the nucleic acids.

"Inducible promoter" refers to a regulated promoter that can be turned on in one or more cell types by an external stimulus, such as a chemical, light, hormone, stress, temperature or a pathogen.

An "initiation site" is region surrounding the position of the first nucleotide that is part of the transcribed sequence, which is defined as position +1. All nucleotide positions of the gene are numbered by reference to the first nucleotide of the transcribed sequence, which resides within the initiation site. Downstream sequences (i.e., sequences in the 3' direction) are denominated positive, while upstream sequences (i.e., sequences in the 5' direction) are denominated negative.

An "isolated" or "purified" nucleic acid or an "isolated" or "purified" polypeptide is a nucleic acid or polypeptide that, by the hand of man, exists apart from its native environment and is therefore not a product of nature. An isolated nucleic acid or polypeptide may exist in a purified form or may exist in a non-native environment such as, for example, within a transgenic host cell.

The term "invader oligonucleotide" refers to an oligonucleotide that contains sequences at its 3' end that are substantially the same as sequences located at the 5' end of a probe oligonucleotide. These regions will compete for hybridization to the same segment along a complementary target nucleic acid.

The term "label" refers to any atom or molecule that can be used to provide a detectable (preferably quantifiable) signal, and that can be attached to a nucleic acid or protein. Labels may provide signals detectable by fluorescence, radioactivity, colorimetry, gravimetry, X-ray diffraction or absorption, magnetism, enzymatic activity, and the like.

The term "nucleic acid" refers to deoxyribonucleotides or ribonucleotides and polymers thereof in either single- or double-stranded form, composed of monomers (nucleotides) containing a sugar, phosphate and a base that is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the reference sequence explicitly indicated.

The term "oligonucleotide" as used herein is defined as a molecule comprised of two or more deoxyribonucleotides or ribonucleotides, preferably more than three, and usually more than ten or fifteen. There is no precise upper limit on the size of an oligonucleotide. However, in general, an oligonucleotide is shorter than about 250 nucleotides, preferably shorter than about 200 nucleotides and more preferably shorter than about 100 nucleotides. The exact size will depend on many factors, which in turn depends on the ultimate function or use of the oligonucleotide. The oligonucleotide may be generated in any manner, including chemical synthesis, DNA replication, reverse transcription, or a combination thereof.

The terms "open reading frame" and "ORF" refer to the amino acid sequence encoded between translation initiation and termination codons of a coding sequence. The terms "initiation codon" and "termination codon" refer to a unit of three adjacent nucleotides ('codon') in a coding sequence that specifies initiation and chain termination, respectively, of protein synthesis (mRNA translation).

"Operably linked" means joined as part of the same nucleic acid molecule, so that the function of one is affected by the other. In general, "operably linked" also means that two or more nucleic acids are suitably positioned and oriented so that they can function together. Nucleic acids are often operably linked to permit transcription of a coding region to be initiated from the promoter. For example, a regulatory sequence is said to be "operably linked to" or "associated with" a DNA sequence that codes for an RNA or a polypeptide if the two sequences are situated such that the regulatory sequence affects expression of the coding region (i.e., that the coding sequence or functional RNA is under the transcriptional control of the promoter). Coding regions can be operably-linked to regulatory sequences in sense or antisense orientation.

The term "probe oligonucleotide" refers to an oligonucleotide that interacts with a target nucleic acid to form a cleavage structure in the presence or absence of an invader oligonucleotide. When annealed to the target nucleic acid, the probe oligonucleotide and target form a cleavage structure and cleavage occurs within the probe oligonucleotide. The presence of an invader oligonucleotide upstream of the probe oligonucleotide can shift the site of cleavage within the probe oligonucleotide (relative to the site of cleavage in the absence of the invader).

"Promoter" refers to a nucleotide sequence, usually upstream (5') to a coding region, which controls the expression of the coding region by providing the recognition site for RNA polymerase and other factors required for proper transcription. "Promoter" includes but is not limited a minimal promoter that is a short DNA sequence comprised of a TATA-box. Hence, a promoter includes other sequences that serve to specify the site of transcription initiation and control or regulate expression, for example, enhancers. Accordingly, an "enhancer" is a DNA sequence that can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Promoters may be derived in their entirety from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions.

The terms "protein," "peptide" and "polypeptide" are used interchangeably herein.

"Regulatory sequences" and "regulatory elements" refer to nucleotide sequences that control some aspect of the expression of nucleic acid sequences. Such sequences or elements can be located upstream (5' non-coding sequences), within, or downstream (3' non-coding sequences) of a coding sequence. "Regulatory sequences" and "regulatory elements" influence the transcription, RNA processing or stability, or translation of the associated coding sequence. Regulatory sequences include enhancers, introns, promoters, polyadenylation signal sequences, splicing signals, termination signals, and translation leader sequences. Regulatory sequences also include natural and synthetic sequences.

As used herein, the term "selectable marker" refers to a gene that encodes an observable or selectable trait that is expressed and can be detected in an organism having that gene. Selectable markers are often linked to a nucleic acid of interest that may not encode an observable trait in order to trace or select for the presence of the nucleic acid of interest. Any selectable marker known to one of skill in the art can be used with the nucleic acids of the invention. Some selectable markers allow the host to survive under circumstances where, without the marker, the host would otherwise die. Examples of selectable markers include antibiotic resistance, for example, tetracycline or ampicillin resistance.

As used herein the term "stringency" is used to define the conditions of temperature, ionic strength, and the presence of other compounds such as organic solvents, under which nucleic acid hybridizations are conducted. With "high stringency" conditions, nucleic acid base pairing will occur only between nucleic acids that have a high frequency of complementary base sequences. With "weak" or "low" stringency conditions nucleic acids the frequency of complementary sequences is usually less, so that nucleic acids with differing sequences can be detected and/or isolated.

The terms "substantially similar" and "substantially homologous" refer to nucleotide and amino acid sequences that represent functional equivalents of the instant inventive sequences. For example, altered nucleotide sequences that simply reflect the degeneracy of the genetic code but nonetheless encode amino acid sequences that are identical to the inventive amino acid sequences are substantially similar to the inventive sequences. In addition, amino acid sequences that are substantially similar to the instant sequences are those wherein overall amino acid identity is sufficient to provide an active, thermally stable DNA polymerase I. For example, amino acid sequences that are substantially similar to the sequences of the invention are those wherein the overall amino acid identity is 80% or greater, preferably 90% or greater, such as 91%, 92%, 93%, or 94%, and more preferably 95% identity or greater, such as 96%, 97%, 98%, or 99% identity, relative to the amino acid sequences of the invention.

A "terminating agent," "terminating nucleotide" or "terminator" in relation to DNA synthesis or sequencing refers to compounds capable of specifically terminating a DNA sequencing reaction at a specific base, such compounds include but are not limited to, dideoxynucleosides having a 2',3' dideoxy structure (e.g., ddATP, ddCTP, ddGTP and ddTTP).

"Thermostable" means that a nucleic acid polymerase remains active at a temperature greater than about 37° C. Preferably, the nucleic acid polymerases of the invention remain active at a temperature greater than about 42° C. More preferably, the nucleic acid polymerases of the invention remain active at a temperature greater than about 50° C. Even more preferably, the nucleic acid polymerases of the invention remain active after exposure to a temperature greater than about 60° C. Most preferably, the nucleic acid polymerases of the invention remain active despite exposure to a temperature greater than about 70° C.

A "transgene" refers to a gene that has been introduced into the genome by transformation and is stably maintained. Transgenes may include, for example, genes that are either heterologous or homologous to the genes of a particular organism to be transformed. Additionally, transgenes may comprise native genes inserted into a non-native organism, or chimeric genes. The term "endogenous gene" refers to a native gene in its natural location in the genome of an organism. A "foreign" or "exogenous" gene refers to a gene not normally found in the host organism but that is introduced by gene transfer.

The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms." Transformation may be accomplished by a variety of means known to the art including calcium DNA co-precipitation, electroporation, viral infection, and the like.

The "variant" of a reference nucleic acid, protein, polypeptide or peptide, is a nucleic acid, protein, polypeptide or peptide, respectively, with a related but different sequence than the respective reference nucleic acid, protein, polypeptide or peptide. The differences between variant and reference nucleic acids, proteins, polypeptides or peptides are silent or conservative differences. A variant nucleic acid differs from a reference nucleic acid in nucleotide sequence whereas a variant nucleic acid, protein, polypeptide or peptide differs in amino acid sequence from the reference protein, polypeptide or peptide, respectively. A variant and reference nucleic acid, protein, polypeptide or peptide may differ in sequence by one or more substitutions, insertions, additions, deletions, fusions and truncations, which may be present in any combination. Differences can be minor (e.g., a difference of one nucleotide or amino acid) or more substantial. However, the structure and function of the variant is not so different from the reference that one of skill in the art would not recognize that the variant and reference are related in structure and/or function. Generally, differences are limited so that the reference and the variant are closely similar overall and, in many regions, identical.

The term "vector" is used to refer to a nucleic acid that can transfer another nucleic acid segment(s) into a cell. A "vector" includes, inter alia, any plasmid, cosmid, phage or nucleic acid in double- or single-stranded, linear or circular form that may or may not be self-transmissible or mobilizable. It can transform prokaryotic or eukaryotic host cells either by integration into the cellular genome or by existing extrachromosomally (e.g., autonomous replicating plasmid with an origin of replication). Vectors used in bacterial systems often contain an origin of replication that allows the vector to replicate independently of the bacterial chromosome. The term "expression vector" refers to a vector containing an expression cassette.

The term "wild-type" refers to a gene or gene product that has the characteristics of that gene or gene product when isolated from a naturally occurring source. A wild-type gene is the gene form most frequently observed in a population and thus arbitrarily is designated the "normal" or "wild-type" form of the gene. In contrast, the term "variant" or "derivative" refers to a gene or gene product that displays modifications in sequence and or functional properties (i.e., altered characteristics) when compared to the wild-type gene or gene product. Naturally occurring derivatives can be isolated. They are identified by the fact that they have altered characteristics when compared to the wild-type gene or gene product.

Polymerase Nucleic Acids

The invention provides isolated nucleic acids encoding *Thermus brockianus* nucleic acid polymerases, as well as derivative, fragment and variant nucleic acids thereof that encode active, thermally stable nucleic acid polymerases. Thus, one aspect of the invention includes the nucleic acid polymerases encoded by the polynucleotide sequences contained in *Thermus brockianus* strains YS38 and AZN. Any nucleic acid encoding amino acid sequence SEQ ID NO:9, SEQ ID NO:10, SEQ ID NO:11, SEQ ID NO:12, SEQ ID NO:13, SEQ ID NO:14, SEQ ID NO:15, and SEQ ID NO:16, which are amino acid sequences for wild type and several derivative *Thermus brockianus* polymerases, are also contemplated by the present invention.

In one embodiment, the invention provides a nucleic acid of SEQ ID NO:1, a wild type *Thermus brockianus* nucleic acid encoding nucleic acid polymerase from strain YS38:

```
  1  ATGCTTCCCC TCTTTGAGCC CAAGGGCCGG GTGCTCCTGG
     TGGACGGCCA

51  CCACCTGGCC TACCGTAACT TCTTCGCCCT CAAGGGGCTC
     ACCAGGAGCC

101  GGGGCGAGCC CGTGCAAGGG GTCTACGGCT TCGCCAAAAG
     CCTCCTCAAG

151  GCCCTGAAGG AGGACGGGGA CGTGGTCATC GTGGTCTTTG
     ACGCCAAGGC

201  CCCCTCTTTT CGCCACGAGG CCTACGGGGC CTACAAGGCG
     GGCCGGGGCC

251  CTACCCCGGA GGACTTTCCG AGGCAGCTTG CCCTCATGAA
     GGAGCTTGTG

301  GACCTTTTGG GGCTGGAGCG CCTCGAGGTC CCGGGCTTTG
     AGGCGGACGA

351  TGTCCTCGCC GCCCTGGCCA AGAAGGCGGA GCGGGAAGGG
     TACGAGGTGC
```

```
 401  GCATCCTCAC CGCCGACCGG GACCTCTTCC AGCTTCTTTC
      GGACCGCATC

451  GCCGTCCTGC ACCCGGAAGG CCACCTCATC ACCCCGGGGT
      GGCTTTGGGA

501  GAGGTACGGC CTGAGACCGG AGCAGTGGGT GGACTTCCGC
      GCCCTGGCCG

551  GCGACCCTTC CGACAACATC CCCGGGGTGA AGGGGATCGG
      CGAGAAGACG

601  GCCCTGAAGC TCCTAAAGGA GTGGGGTAGT CTGGAAAATA
      TCCAAAAAAA

651  CCTGGACCAG GTCAGTCCCC CTTCCGTGCG CGAGAAGATC
      CAGGCCCACC

701  TGGACGACCT CAGGCTCTCC CAGGAGCTTT CCCGGGTGCG
      CACGGACCTT

751  CCCTTGGAGG TGGACTTTAG AAGGCGGCGG GAGCCCGATA
      GGGAAGGCCT

801  TAGGGCCTTC TTAGAGCGGC TTGAGTTCGG GAGCCTCCTC
      CACGAGTTCG

851  GCCTCCTGGA AAGCCCCCAG GCGGCGGAGG AGGCCCCTTG
      GCCGCCGCCG

901  GAAGGGGCCT TCTTGGGCTT CCGCCTCTCC CGGCCCGAGC
      CCATGTGGGC

951  GGAACTCCTT TCCTTGGCGG CAAGCGCCAA GGGCCGGGTC
      TACCGGGCGG

1001  AGGCGCCCCA TAAGGCCCTT TCGGAGCTGA AGGAGATCCG
      GGGGCTTCTC

1051  GCCAAGGACC TCGCCGTCTT GGGCCTGAGG GAGGGGCTCG
      GCCTTCCCCC

1101  CACGGACGAT CCCATGCTCC TCGCCTACCT CGTGGACCCC
      TCCAACACCA

1151  CCCCCGAGGG CGTGGCCCGG CGCTACGGGG GGGAGTGGAC
      GGAGGAGGCC

1201  GGGGAGAGGG CCTTGCTTGC CGAAAGGCTT TACGAGAACC
      TCCTAAGCCG

1251  CCTGAAAGGG GAAGAAAAGC TCCTTTGGCT CTACGAGGAG
      GTGGAAAAGC

1301  CCCTTTCCCG GGTCCTCGCC CACATGGAGG CGACGGGGGT
      GAGGCTGGAC

1351  GTACCCTACC TAAGGGCCCT TTCCCTGGAG GTGGCGGCGG
      AGATGGGCCG

1401  CCTGGAGGAG GAGGTTTTCC GCCTGGCGGG CCACCCCTTC
      AACCTGAACT

1451  CCCGCGACCA GCTGGAAAGG GTGCTCTTTG ACGAGCTCGG
      GCTTCCCCCC

1501  ATCGGCAAGA CGGAAAAAAC CGGGAAGCGC TCCACCAGCG
      CCGCCGTCCT

1551  CGAGGCCCTG CGGGAGGCCC ACCCCATCGT GGAGAAGATC
      CTCCAGTACC

1601  GGGAGCTCGC CAAGCTCAAG GCACCTACA TTGACCTCCT
      TCCCGCCCTG

1651  GTCCACCCCA GGACGGGCAG GCTCCACACC CGCTTCAACC
      AGACGGCCAC

1701  GGCCACGGGC GGCCTTTCCA GCTCCGACCC CAACCTGCAG
      AACATTCCCG
```

```
1751  TGCGCACCCC CTTGGGCCAA AGGATCCGCC GGGCCTTCGT
      GGCCGAGGAG

1801  GGGTACCTTC TCGTGGCCCT GGACTATAGC CAGATTGAGC
      TGAGGGTCCT

1851  GGCCCACCTC TCGGGGACG AAAACCTCAT CCGGGTCTTC
      CAGGAGGGCC

1901  GGGACATCCA CACCCAGACG GCGAGCTGGA TGTTCGGCCT
      GCCGGCGGAG

1951  GCCATAGACC CCCTCAGGCG CCGGGCGGCC AAGACCATCA
      ACTTCGGCGT

2001  CCTCTACGGC ATGTCCGCCC ACCGGCTTTC CCAGGAGCTG
      GGCATCCCCT

2051  ACGAGGAGGC GGTGGCCTTC ATTGACCGCT ATTTCCAGAG
      CTACCCCAAG

2101  GTGAAGGCCT GGATTGAAAG GACCCTGGAG GAGGGGCGGC
      AAAGGGGGTA

2151  CGTGGAGACC CTCTTCGGCC GCAGGCGCTA CGTGCCCGAC
      CTCAACGCCC

2201  GGGTAAAGAG CGTGCGGGAG GCGGCGGAGC GCATGGCCTT
      TAACATGCCC

2251  GTGCAGGGCA CCGCCGCTGA CCTGATGAAG CTCGCCATGG
      TGAGGCTCTT

2301  CCCTAGGCTT CCCGAGGTGG GGGCGAGGAT GCTCCTCCAG
      GTCCACGACG

2351  AGCTCCTCCT GGAGGCGCCC AAGGAGCGGG CGGAGGAGGC
      GGCGGCCCTG

2401  GCCAAGGAGG TCATGGAGGG GGTCTGGCCC CTGGCCGTGC
      CCCTGGAGGT

2451  GGAGGTGGGC ATCGGGGAGG ACTGGCTTTC CGCCAAGGGC
      TAG
```

In another embodiment, the invention provides a nucleic acid of SEQ ID NO:2, another wild type *Thermus brockianus* nucleic acid encoding a nucleic acid polymerase, but from strain 2AZN.

```
   1  ATGCTTCCCC TCTTTGAGCC CAAGGGCCGG GTGCTCCTGG
      TGGACGGCCA

51  CCACCTGGCC TACCGTAACT TCTTCGCCCT CAAGGGGCTC
      ACCACGAGCC

101  GGGGCGAGCC CGTGCAAGGG GTCTACGGCT TCGCCAAAAG
      CCTCCTCAAG

151  GCCCTGAAGG AGGACGGGGA CGTGGTCATC GTGGTCTTTG
      ACGCCAAGGC

201  CCCCTCTTTT CGCCACGAGG CCTACGGGGC CTACAAGGCG
      GGCCGGGCCC

251  CTACCCCGA GGACTTTCCG AGGCAGCTTG CCCTCATGAA
      GGAGCTTGTG

301  GACCTTTTGG GGCTGGAGCG CGTCGAGGTC CCGGGCTTTG
      AGGCGGACGA

351  TGTCCTCGCC GCCCTGGCCA AGAAGGCGGA GCGGGAAGGG
      TACGAGGTGC

401  GCATCCTCAC CGCCGACCGG GACCTCTTCC AGCTTCTTTC
      GGACCGCATC
```

```
 451  GCCGTCCTGC ACCCGGAAGG CCACCTCATC ACCCCGGGGT
      GGCTTTGGGA

501  GAGGTACGGC CTGAGACCGG AGCAGTGGGT GGACTTCCGC
      GCCCTGGCCG

551  GCGACCCTTC CGACAACATC CCCGGGGTGA AGGGGATCGG
      CGAGAAGACG

601  GCCCTGAAGC TCCTAAAGGA GTGGGGTAGT CTGGAAAATA
      TCCAAAAAAA

651  CCTGGACCAG GTCAGTCCCC CTTCCGTGCG CGAGAAGATC
      CAGGCCCACC

701  TGGACGACCT CAGGCTCTCC CAGGAGCTTT CCCGGGTGCG
      CACGGACCTT

751  CCCTTGGAGG TGGACTTTAG AAGGCGGCGG GAGCCCGATA
      GGGAAGGCCT

801  TAGGGCCTTC TTAGAGCGGC TTGAGTTCGG GAGCCTCCTC
      CACGAGTTCG

851  GCCTCCTGGA AAGCCCCAG GCGGCGGAGG AGGCCCCTTG
      GCCGCCGCCG

901  GAAGGGGCCT TCTTGGGCTT CCGCCTCTCC CGGCCCGAGC
      CCATGTGGGC

951  GGAACTCCTT TCCTTGGCGG CAAGCGCCAA GGGCCGGGTC
      TACCGGGCGG

1001  AGGCGCCCCA TAAGGCCCTT TCGGACCTGA AGGAGATCCG
      GGGGCTTCTC

1051  GCCAAGGACC TCGCCGTCTT GGCCCTGAGG GAGGGGCTCG
      GCCTTCCCCC

1101  CACGGACGAT CCCATGCTCC TCGCCTACCT CCTGGACCCC
      TCCAACACCA

1151  CCCCCGAGGG CGTGGCCCGG CGCTACGGGG GGGAGTGGAC
      GGAGGAGGCC

1201  GGGGAGAGGG CCTTGCTTGC CGAAAGGCTT TACGAGAACC
      TCCTAAGCCG

1251  CCTGAAAGGG GAAGAAAAGC TCCTTTGGCT CTACGAGGAG
      GTGGAAAAGC

1301  CCCTTTCCCG GGTCCTCGCC CACATGGAGG CCACGGGGGT
      GAGGCTGGAC

1351  GTACCCTACC TAAGGGCCCT TTCCCTGGAG GTGGCGGCGG
      AGATGGGCCG

1401  CCTGGAGGAG GAGGTTTTCC GCCTGGCGGG CCACCCCTTC
      AACCTGAACT

1451  CCCGCGACCA GCTGGAAAGG GTGCTCTTTG ACGAGCTCGG
      GCTTCCCCCC

1501  ATCGGCAAGA CGGAAAAAAC CGGGAAGCGC TCCACCAGCG
      CCGCCGTCCT

1551  CGAGGCCCTG CGGGAGGCCC ACCCCATCGT GGAGAAGATC
      CTCCAGTACC

1601  GGGAGCTCGC CAAGCTCAAG GCACCTACA TTGACCCCCT
      TCCCGCCCTG

1651  GTCCACCCCA GGACGGGCAG GCTCCACACC CGCTTCAACC
      AGACGGCCAC

1701  GGCCACGGGC CGCCTTTCCA GCTCCGACCC CAACCTGCAG
      AACATTCCCG

1751  TGCGCACCCC CTTGGGCCAA AGGATCCGCC GGGCCTTCGT
      GGCCGAGGAG

1801  GGGTACCTTC TCGTGGCCCT GGACTATAGC CAGATTGAGC
      TGAGGGTCCT

1851  GGCCCACCTC TCGGGGACG AAAACCTCAT CCGGGTCTTC
      CAGGAGGGCC

1901  GGGACATCCA CACCCAGACG GCGAGCTGGA TGTTCGGCCT
      GCCGGCGGAG

1951  GCCATAGACC CCCTCAGGCG CCGGGCGGCC AAGACCATCA
      ACTTCGGCGT

2001  CCTCTACGGC ATGTCCGCCC ACCGGCTTTC CCAGGAGCTG
      GGCATCCCCT

2051  ACGAGGAGGC GGTGGCCTTC ATTGACCGCT ATTTCCAGAG
      CTACCCCAAG

2101  GTGAAGGCCT GGATTGAAAG GACCCTGGAG GAGGGGCGGC
      AAAGGGGGTA

2151  CGTGGAGACC CTCTTCGGCC GCAGGCGCTA CGTGCCCGAC
      CTCAACGCCC

2201  GGGTAAAGAG CGTGCGGGAG GCGGCGGAGC GCATGGCCTT
      TAACATGCCC

2251  GTGCAGGGCA CCGCCGCTGA CCTGATGAAG CTCGCCATGG
      TGAGGCTCTT

2301  CCCTAGGCTT CCCGAGGTGG GGGCGAGGAT GCTCCTCCAG
      GTCCACGACG

2351  AGCTCCTCCT GGAGGCGCCC AAGGAGCGGG CGGAGGAGGC
      GGCGGCCCTG

2401  GCCAAGGAGG TCATGGAGGG AGTCTGGCCC CTGGCCGTGC
      CCCTGGAGGT

2451  GGAGGTGGGC ATCGGGGAGG ACTGGCTTTC CGCCAAGGGC
      TAGTCGAC
```

In another embodiment, the invention provides a nucleic acid from *Thermus brockianus* strain YS38 having SEQ ID NO:3, a derivative nucleic acid having GAC (encoding Asp) in place of GGC (encoding Gly) at positions 127-129. SEQ ID NO:3 is provided below:

```
   1  ATGCTTCCCC TCTTTGAGCC CAAGGGCCGG GTGCTCCTGG
      TGGACGGCCA

51  CCACCTGGCC TACCGTAACT TCTTCGCCCT CAAGGGGCTC
      ACCACGAGCC

101  GGGGCGAGCC CGTGCAAGGG GTCTACGACT TCGCCAAAAG
      CCTCCTCAAG

151  GCCCTGAAGG AGGACGGGGA CGTGGTCATC GTGGTCTTTG
      ACGCCAAGGC

201  CCCCTCTTTT CGCCACGAGG CCTACGGGGC CTACAAGGCG
      GGCCGGGCCC

251  CTACCCCGGA GGACTTTCCG AGGCAGCTTG CCCTCATGAA
      GGAGCTTGTG

301  GACCTTTTGG GGCTGGAGCG CCTCGAGGTC CCGGGCTTTG
      AGGCGGACGA

351  TGTCCTCGCC GCCCTGGCCA AGAAGGCGGA GCGGGAAGGG
      TACGAGGTGC

401  GCATCCTCAC CGCCGACCGG GACCTCTTCC AGCTTCTTTC
      GGACCGCATC

451  GCCGTCCTGC ACCCGGAAGG CCACCTCATC ACCCCGGGGT
      GGCTTTGGGA
```

-continued

```
 501  GAGGTACGGC CTGAGACCGG AGCAGTGGGT GGACTTCCGC
      GCCCTGGCCG
 551  GCGACCCTTC CGACAACATC CCCGGGGTGA AGGGGATCGG
      CGAGAAGACG
 601  GCCCTGAAGC TCCTAAAGGA GTGGGGTAGT CTGGAAAATA
      TCCAAAAAAA
 651  CCTGGACCAG GTCAGTCCCC CTTCCGTGCG CGAGAAGATC
      CAGGCCCACC
 701  TGGACGACCT CAGGCTCTCC CAGGAGCTTT CCCGGGTGCG
      CACGGACCTT
 751  CCCTTGGAGG TGGACTTTAG AAGGCGGCGG GAGCCCGATA
      GGGAAGGCCT
 801  TAGGGCCTTC TTAGAGCGGC TTGAGTTCGG GAGCCTCCTC
      CACGAGTTCG
 851  GCCTCCTGGA AAGCCCCCAG GCGGCGGAGG AGGCCCCTTG
      GCCGCCGCCG
 901  GAAGGGGCCT TCTTGGGCTT CCGCCTCTCC CGGCCCGAGC
      CCATGTGGGC
 951  GGAACTCCTT TGCTTGGCGG CAAGCGCCAA GGGCCGGGTC
      TACCGGGCGG
1001  AGGCGCCCCA TAAGGCCCTT TCGGACCTGA AGGAGATCCG
      GGGGCTTCTC
1051  GCCAAGGACC TCGCCGTCTT GGCCCTGAGG GAGGGGCTCG
      GCCTTCCCCC
1101  CACGGACGAT CCCATGCTCC TCGCCTACCT CCTGGACCCC
      TCCAACACCA
1151  CCCCCGAGGG CGTGGCCCGG CGCTACGGGG GGGAGTGGAC
      GGAGGAGGCG
1201  GGGGAGAGGG CCTTGCTTGC CGAAAGGCTT TACGAGAACC
      TCCTAAGCCG
1251  CCTGAAAGGG GAAGAAAAGC TCCTTTGGCT CTACGAGGAG
      GTGGAAAAGC
1301  CCCTTTCCCG GGTCCTCGCC CACATGGAGG CCACGGGGGT
      GAGGCTGGAC
1351  GTACCCTACC TAAGGGCCCT TTCCCTGGAG GTGGCGGCGG
      AGATGGGGCG
1401  CCTGGAGGAG GAGGTTTTCC GCCTGGCGGG CCACCCCTTC
      AACCTGAACT
1451  CCCGCGACCA GCTGGAAAGG GTGCTCTTTG ACGAGCTCGG
      GCTTCCCCCC
1501  ATCGGCAAGA CGGAAAAAAC CGGGAAGCGC TCCACCAGCG
      CCGCCGTCCT
1551  CGAGGCCCTG CGGGAGGCCC ACCCCATCGT GGAGAAGATC
      CTCCAGTACC
1601  GGGAGCTCGC CAAGCTCAAG GGCACCTACA TTGACCTCCT
      TCCCGCCCTG
1651  GTCCACCCCA GGACGGGCAG GCTCCACACC CGCTTCAACC
      AGACGGCCAC
1701  GGCCACGGGC CGCCTTTCCA GCTCCGACCC CAACCTGCAG
      AACATTCCCG
1751  TGCGCACCCC CTTGGGCCAA AGGATCCGCC GGGCCTTCGT
      GGCCGAGGAG
1801  GGGTACCTTC TCGTGGCCCT GGACTATAGC CAGATTGAGC
      TGAGGGTCCT
1851  GGCCCACCTC TCGGGGGACG AAAACCTCAT CCGGGTCTTC
      CAGGAGGGCC
1901  GGGACATCCA CACCCAGACG GCGAGCTGGA TGTTCGGCCT
      GCCGGCGGAG
1951  GCCATAGACC CCCTCAGGCG CCGGGCGGCC AAGACCATCA
      ACTTCGGCGT
2001  CCTCTACGGC ATGTCCGCCC ACCGGCTTTC CCAGGAGCTG
      GGCATCCCCT
2051  ACGAGGAGGC GGTGGCCTTC ATTGACCGCT ATTTCCAGAG
      CTACCCCAAG
2101  GTGAAGGCCT GGATTGAAAG GACCCTGGAG GAGGGGCGGC
      AAAGGGGGTA
2151  CGTGGAGACC CTCTTCGGCC GCAGGCGCTA CGTGCCCGAC
      CTCAACGCCC
2201  GGGTAAAGAG CGTGCGGGAG GCGGCGGAGC GCATGGCCTT
      TAACATGCCC
2251  GTGCAGGGCA CCGCCGCTGA CCTGATGAAG CTCGCCATGG
      TGAGGCTCTT
2301  CCCTAGGCTT CCCGAGGTGG GGGCGAGGAT GCTCCTCCAG
      GTCCACGACG
2351  AGCTCCTCCT GGAGGCGCCC AAGGAGCGGG CGGAGGAGGC
      GGCGGCCCTG
2401  GCCAAGGAGG TCATGGAGGG GGTCTGGCCC CTGGCCGTGC
      CCCTGGAGGT
2451  GGAGGTGGGC ATCGGGGAGG ACTGGCTTTC CGCCAAGGGC
      TAG
```

In another embodiment, the invention provides a derivative nucleic acid related to *Thermus brockianus* strain 2AZN having SEQ ID NO:4. SEQ ID NO:4 is a derivative nucleic acid having GAC (encoding Asp) in place of GGC (encoding Gly) at positions 127-129 and is provided below:

```
   1  ATGCTTCCCC TCTTTGAGCC CAAGGGCCGG GTGCTCCTGG
      TGGACGGCCA
  51  CCACCTGGCC TACCGTAACT TCTTCGCCCT CAAGGGGCTC
      ACCACGAGCC
 101  GGGGCGAGCC CGTGCAAGGG GTCTACGACT TCGCCAAAAG
      CCTCCTCAAG
 151  GCCCTGAAGG AGGACGGGGA CGTGGTCATC GTGGTCTTTG
      ACGCCAAGGC
 201  CCCCTCTTTT CGCCACGAGG CCTACGGGGC CTACAAGGCG
      GGCCGGGCCC
 251  CTACCCCGGA GGACTTTCCG AGGCAGCTTG GCCTCATGAA
      GGAGCTTGTG
 301  GACCTTTTGG GGCTGGAGCG CCTCGAGGTC CCGGGCTTTG
      AGGCGGACGA
 351  TGTCCTCGCC GCCCTGGCCA AGAAGGCGGA GCGGGAAGGG
      TACGAGGTGC
 401  GCATCCTCAC CGCCGACCGG GACCTCTTCC AGCTTCTTTC
      GGACCGCATC
 451  GCCGTCCTGC ACCCGGAAGG CCACCTCATC ACCCCGGGGT
      GGCTTTGGGA
 501  GAGGTACGGC CTGAGACCGG AGCAGTGGGT GGACTTCCGC
      GCCCTGGCCG
```

-continued

```
 551 GCGACCCTTC CGACAACATC CCCGGGGTGA AGGGGATCGG
     GGAGAAGACG

601 GCCCTGAAGC TCCTAAAGGA GTGGGGTAGT CTGGAAAATA
     TCCAAAAAAA

651 CCTGGACCAG GTCAGTCCCC CTTCCGTGCG CGAGAAGATC
     CAGGCCCACC

701 TGGACGACCT CAGGCTCTCC CAGGAGCTTT CCCGGGTGCG
     CACGGACCTT

751 CCCTTGGAGG TGGACTTTAG AAGGCGGCGG GAGCCCGATA
     GGGAAGGCCT

801 TAGGGCCTTC TTAGAGCGGC TTGAGTTCGG GAGCCTCCTC
     CACGAGTTCG

851 GCCTCCTGGA AAGCCCCCAG GCGGCGGAGG AGGCCCCTTG
     GCCGCCGCCG

901 GAAGGGGCCT TCTTGGGCTT CCGCCTCTCC CGGCCCGAGC
     CCATGTGGGC

951 GGAACTCCTT TCCTTGGCGG CAAGCGCCAA GGGCCGGGTC
     TACCGGGCGG

1001 AGGCGCCCCA TAAGGCCCTT TCGGACCTGA AGGAGATCCG
     GGGGCTTCTC

1051 GCCAAGGACC TCGCCGTCTT GGCCCTGAGG GAGGGGCTCG
     GCCTTCCCCC

1101 CACGGACGAT CCCATGCTCC TCGCCTACCT CCTGGACCCC
     TCCAACACCA

1151 CCCCCGAGGG CGTGGCCCGG CGCTACGGGG GGGAGTGGAC
     GGAGGAGGCG

1201 GGGGAGAGGG CCTTGCTTGC CGAAAGGCTT TACGAGAACC
     TCCTAAGCCG

1251 CCTGAAAGGG GAAGAAAAGC TCCTTTGGCT CTACGAGGAG
     GTGGAAAAGC

1301 CCCTTTCCCG GGTCCTCGCC CACATGGAGG CCACGGGGGT
     GAGGCTGGAC

1351 GTACCCTACC TAAGGGCCCT TTCCCTGGAG GTGGCGGCGG
     AGATGGGCCG

1401 CCTGGAGGAG GAGGTTTTCC GCCTGGCGGG CCACCCCTTC
     AACCTGAACT

1451 CCCGCGACCA GCTGGAAAGG GTGCTCTTTG ACGAGCTCGG
     GCTTCCCCCC

1501 ATCGGCAAGA CGGAAAAAAC CGGGAAGCGC TCCACCAGCG
     CCGCCGTCCT

1551 CGAGGCCCTG CGGGAGGCCC ACCCCATCGT GGAGAAGATC
     CTCCAGTACC

1601 GGGAGCTCGC CAAGCTCAAG GGCACCTACA TTGACCCCCT
     TCCCGCCCTG

1651 GTCCACCCCA GGACGGGCAG GCTCCACACC CGCTTCAACC
     AGACGGCCAC

1701 GGCCACGGGC CGCCTTTCCA GCTCCGACCC CAACCTGCAG
     AACATTCCCG

1751 TGCGCACCCC CTTGGGCCAA AGGATCCGCC GGGCCTTCGT
     GGCCGAGGAG

1801 GGGTACCTTC TCGTGGCCCT GGACTATAGC CAGATTGAGC
     TGAGGGTCCT

1851 GGCCCACCTC TCGGGGGACG AAAACCTCAT CCGGGTCTTC
     CAGGAGGGCC

1901 GGGACATCCA CACCCAGACG GCGAGCTGGA TGTTCGGCCT
     GCCGGCGGAG

1951 GCCATAGACC CCCTCAGGCG CCGGGCGGCC AAGACCATCA
     ACTTCGGCGT

2001 CCTCTACGGC ATGTCCGCCC ACCGGCTTTC CCAGGAGCTG
     GGCATCCCCT

2051 ACGAGGAGGC GGTGGCCTTC ATTGACCGCT ATTTCCAGAG
     CTACCCCAAG

2101 GTGAAGGCCT GGATTGAAAG GACCCTGGAG GAGGGGCGGC
     AAAGGGGGTA

2151 CGTGGAGACC CTCTTCGGCC GCAGGCGCTA CGTGCCCGAC
     GTCAACGCCC

2201 GGGTAAAGAG CGTGCGGGAG GCGGCGGAGC GCATGGCCTT
     TAACATGCCC

2251 GTGCAGGGCA CCGCCGCTGA CCTGATGAAG CTCGCCATGG
     TGAGGCTCTT

2301 CCCTAGGCTT CCCGAGGTGG GGGCGAGGAT GCTCCTCCAG
     GTCCACGACG

2351 AGCTCCTCCT GGAGGCGCCC AAGGAGCGGG CGGAGGAGGC
     GGCGGCCCTG

2401 GCCAAGGAGG TCATGGAGGG AGTCTGGCCC CTGGCCGTGC
     CCCTGGAGGT

2451 GGAGGTGGGC ATCGGGGAGG ACTGGCTTTC CGCCAAGGGC
     TAGTCGAC
```

In another embodiment, the invention provides a derivative nucleic acid related to *Thermus brockianus* strain YS38, having SEQ ID NO:5. SEQ ID NO:5 is a derivative nucleic acid having TAC (encoding Tyr) in place of TTC (encoding Phe) at positions 1993-95 and is provided below:

```
   1 ATGCTTCCCC TCTTTGAGCC CAAGGGCCGG GTGCTCCTGG
     TGGACGGCCA

51 CCACCTGGCC TACCGTAACT TCTTCGCCCT CAAGGGGCTC
     ACCACGAGCC

101 GGGGCGAGCC CGTGCAAGGG GTCTACGGCT TCGCCAAAAG
     CCTCCTCAAG

151 GCCCTGAAGG AGGACGGGGA CGTGGTCATC GTGGTCTTTG
     ACGCCAAGGC

201 CCCCTCTTTT CGCCACGAGG CCTACGGGGC CTACAAGGCG
     GGCCGGGCCC

251 CTACCCCGGA GGACTTTCCG AGGCAGCTTG CCCTCATGAA
     GGAGCTTGTG

301 GACCTTTTGG GGCTGGAGCG CCTCGAGGTC CCGGGCTTTG
     AGGCGGACGA

351 TGTCCTCGCC GCCCTGGCCA AGAAGGCGGA GCGGGAAGGG
     TACGAGGTGC

401 GCATCCTCAC GGCCGACCGG GACCTCTTCC AGCTTCTTTC
     GGACCGCATC

451 GCCGTCCTGC ACCCGGAAGG CCACCTCATC ACCCCGGGGT
     GGCTTTGGGA

501 GAGGTACGGC CTGAGACCGG AGCAGTGGGT GGACTTCCGC
     GCCCTGGCCG

551 GCGACCCTTC CGACAACATC CCCGGGGTGA AGGGGATCGG
     CGAGAAGACG
```

-continued

```
 601 GCCCTGAAGC TCCTAAAGGA GTGGGGTAGT CTGGAAAATA
     TCCAAAAAAA
 651 CCTGGACCAG GTCAGTCCCC CTTCCGTGCG CGAGAAGATC
     CAGGCCCACC
 701 TGGACGACCT CAGGCTCTCC CAGGAGCTTT CCCGGGTGCG
     CACGGACCTT
 751 CCCTTGGAGG TGGACTTTAG AAGGCGGCGG GAGCCCGATA
     GGGAAGGCCT
 801 TAGGGCCTTC TTAGAGCGGC TTGAGTTCGG GAGCCTCCTC
     CACGAGTTCG
 851 GCCTCCTGGA AAGCCCCCAG GCGGCGGAGG AGGCCCCTTG
     GCCGCCGCCG
 901 GAAGGGGCCT TCTTGGGCTT CCGCCTCTCC CGGCCCGAGC
     CCATGTGGGC
 951 GGAACTCCTT TCCTTGGCGG CAAGCGCCAA GGGCCGGGTC
     TACCGGGCGG
1001 AGGCGCCCCA TAAGGCCCTT TCGGACCTGA AGGAGATCCG
     GGGGCTTCTC
1051 GCCAAGGACC TCGCCGTCTT GGCCCTGAGG GAGGGGCTCG
     GCCTTCCCCC
1101 CACGGACGAT CCCATGCTCC TCGCCTACCT CCTGGACCCC
     TCCAACACCA
1151 CCCCCGAGGG CGTGGCCCGG CGCTACGGGG GGGAGTGGAC
     GGAGGAGGCG
1201 GGGGAGAGGG CCTTGCTTGC CGAAAGGCTT TACGAGAACC
     TCCTAAGCCG
1251 CCTGAAAGGG GAAGAAAAGC TCCTTTGGCT CTACGAGGAG
     GTGGAAAAGC
1301 CCCTTTCCCG GGTCCTCGCC CACATGGAGG CCACGGGGGT
     GAGGCTGGAC
1351 GTACCCTACC TAAGGGCCCT TTCCCTGGAG GTGGCGGCGG
     AGATGGGCCG
1401 CCTGGAGGAG GAGGTTTTCC GCCTGGCGGG CCACCCCTTC
     AACCTGAACT
1451 CCCGCGACCA GCTGGAAAGG GTGCTCTTTG ACGAGCTCGG
     GCTTCCCCCC
1501 ATCGGCAAGA CGGAAAAAAC CGGGAAGCGC TCCACCAGCG
     CCGCCGTCCT
1551 CGAGGCCCTG CGGGAGGCCC ACCCCATCGT GGAGAAGATC
     CTCCAGTACC
1601 GGGAGCTCGC CAAGCTCAAG GCACCTACA TTGACCTCCT
     TCCCGCCCTG
1651 GTCCACCCCA GGACGGGCAG GCTCCACACC CGCTTCAACC
     AGACGGCCAC
1701 GGCCACGGGC CGCCTTTCCA GCTCCGACCC CAACCTGCAG
     AACATTCCCG
1751 TGCGCACCCC CTTGGGCCAA AGGATCCGCC GGGCCTTCGT
     GGCCGAGGAG
1801 GGGTACCTTC TCGTGGCCCT GGACTATAGC CAGATTGAGC
     TGAGGGTCCT
1851 GGCCCACCTC TCGGGGACG AAAACCTCAT CCGGGTCTTC
     CAGGAGGGCC
1901 GGGACATCCA CACCCAGACG GGGAGCTGGA TGTTCGGCCT
     GCCGGCGGAG
1951 GCCATAGACC CCCTCAGGCG CCGGGCGGCC AAGACCATCA
     ACTACGGCGT
2001 CCTCTACGGC ATGTCCGCCC ACCGGCTTTC CCAGGAGCTG
     GGCATCCCCT
2051 ACGAGGAGGC GGTGGCCTTC ATTGACCGCT ATTTCCAGAG
     GTACCCCAAG
2101 GTGAAGGCCT GGATTGAAAG GACCCTGGAG GAGGGGCGGC
     AAAGGGGGTA
2151 CGTGGAGACC CTCTTCGGCC GCAGGCGCTA CGTGCCCGAC
     CTCAACGCCC
2201 GGGTAAAGAG CGTGCGGGAG GCGGCGGAGC GCATGGCCTT
     TAACATGCCC
2251 GTGCAGGGCA CCGCCGCTGA CGTGATGAAG CTCGCCATGG
     TGAGGCTCTT
2301 CCCTAGGCTT CCCGAGGTGG GGGCGAGGAT GCTCCTCCAG
     GTCCACGACG
2351 AGCTCCTCCT GGAGGCGCCC AAGGAGCGGG CGGAGGAGGC
     GGCGGCCCTG
2401 GCCAAGGAGG TCATGGAGGG GGTCTGGCCC CTGGCCGTGC
     CCCTGGAGGT
2451 GGAGGTGGGC ATCGGGGAGG ACTGGCTTTC CGCCAAGGGC
     TAG
```

In another embodiment, the invention provides a derivative nucleic acid related to *Thermus brockianus* strain 2AZN, having SEQ ID NO:6. SEQ ID NO:6 is a derivative nucleic acid having TAC (encoding Tyr) in place of TTC (encoding Phe) at positions 1993-95 and is provided below:

```
   1 ATGCTTCCCC TCTTTGAGCC CAAGGGCCGG GTGCTCCTGG
     TGGACGGCCA
  51 CCACCTGGCC TACCGTAACT TCTTCGCCCT CAAGGGGCTC
     ACCACGAGCC
 101 GGGGCGAGCC CGTGCAAGGG GTCTACGGCT TCGCCAAAAG
     CCTCCTCAAG
 151 GCCCTGAAGG AGGACGGGGA CGTGGTCATC GTGGTCTTTG
     ACGCCAAGGC
 201 CCCCTCTTTT CGCCACGAGG CCTACGGGGC CTACAAGGCG
     GGCCGGGCCC
 251 CTACCCCGGA GGACTTTCCG AGGCAGCTTG CCCTCATGAA
     GGAGCTTGTG
 301 GACCTTTTGG GGCTGGAGCG CCTCGAGGTC CCGGGCTTTG
     AGGCGGACGA
 351 TGTCCTCGCC GCCCTGGCCA AGAAGGCGGA GCGGGAAGGG
     TACGAGGTGC
 401 GCATCCTCAC CGCCGACCGG GACCTCTTCC AGCTTCTTTC
     GGACCGCATC
 451 GCCGTCCTGC ACCCGGAAGG CCACCTCATC ACCCCGGGGT
     GGCTTTGGGA
 501 GAGGTACGGC CTGAGACCGG AGCAGTGGGT GGACTTCCGC
     GCCCTGGCCG
 551 GCGACCCTTC CGACAACATC CCCGGGGTGA AGGGGATCGG
     CGAGAAGACG
 601 GCCCTGAAGC TCCTAAAGGA GTGGGGTAGT CTGGAAAATA
     TCCAAAAAAA
```

-continued

```
 651  CCTGGACCAG GTCAGTCCCC CTTCCGTGCG CGAGAAGATC
      CAGGCCCACC

701  TGGACGACCT CAGGCTCTCC CAGGAGCTTT CCCGGGTGCG
      CACGGACCTT

751  CCCTTGGAGG TGGACTTTAG AAGGCGGCGG GAGCCCGATA
      GGGAAGGCCT

801  TAGGGCCTTC TTAGAGCGGC TTGAGTTCGG GAGCCTCCTC
      CACGAGTTCG

851  GCCTCCTGGA AAGCCCCAG GCGGCGGAGG AGGCCCCTTG
      GCCGCCGCCG

901  GAAGGGGCCT TCTTGGGCTT CCGCCTCTCC GGGCCCGAGC
      CCATGTGGGC

951  GGAACTCCTT TCCTTGGCGG CAAGCGCCAA GGGCCGGGTC
      TACCGGGCGG

1001  AGGCGCCCCA TAAGGCCCTT TCGGACCTGA AGGAGATCCG
      GGGGCTTCTC

1051  GCCAAGGACC TCGCCGTCTT GGCCCTGAGG GAGGGGCTCG
      GCCTTCCCCC

1101  CACGGACGAT CCCATGCTCC TCGCCTACCT CCTGGACCCC
      TCCAACACCA

1151  CCCCCGAGGG CGTGGCCCGG CGCTACGGGG GGGAGTGGAC
      GGAGGAGGCG

1201  GGGGAGAGGG CCTTGCTTGC CGAAAGGCTT TACGAGAACC
      TCCTAAGCCG

1251  CCTGAAAGGG GAAGAAAAGC TCCTTTGGCT GTACGAGGAG
      GTGGAAAAGC

1301  CCCTTTCCCG GGTCCTCGCC CACATGGAGG CCACGGGGGT
      GAGGCTGGAC

1351  GTACCCTACC TAAGGGCCCT TTCCCTGGAG GTGGCGGCGG
      AGATGGGCCG

1401  CCTGGAGGAG GAGGTTTTCC GCCTGGCGGG CCACCCCTTC
      AACCTGAACT

1451  CCCGCGACCA GCTGGAAAGG GTGCTCTTTG ACGAGCTCGG
      GCTTCCCCCC

1501  ATCGGCAAGA CGGAAAAAAC CGGGAAGCGC TCCACCAGCG
      CCGCCGTCCT

1551  CGAGGCCCTG CGGGAGGCCC AGCCCATCGT GGAGAAGATC
      CTCCAGTACC

1601  GGGAGCTCGC CAAGCTCAAG GGCACCTACA TTGACCCCCT
      TCCCGCCCTG

1651  GTCCACCCCA GGACGGGCAG GCTCCACACC CGCTTCAACC
      AGACGGCCAC

1701  GGCCACGGGC CGCCTTTCCA GGTCCGACCC CAACCTGCAG
      AACATTCCCG

1751  TGCGCACCCC CTTGGGCCAA AGGATCCGCC GGGCCTTCGT
      GGCCGAGGAG

1801  GGGTACCTTC TCGTGGCCCT GGACTATAGC CAGATTGAGC
      TGAGGGTCCT

1851  GGCCCACCTC TCGGGGACG AAAACCTCAT CCGGGTCTTC
      CAGGAGGGCC

1901  GGGACATCCA CACCCAGACG GCGAGCTGGA TGTTCGGCCT
      GCCGGCGGAG

1951  GCCATAGACC CCCTCAGGCG CCGGGCGGCC AAGACCATCA
      ACTACGGCGT

2001  CCTCTACGGC ATGTCCGCCC ACCGGCTTTC CCAGGAGCTG
      GGCATCCCCT

2051  ACGAGGAGGC GGTGGCCTTC ATTGACCGCT ATTTCCAGAG
      CTACCCCAAG

2101  GTGAAGGCCT GGATTGAAAG GACCCTGGAG GAGGGGCGGC
      AAAGGGGGTA

2151  CGTGGAGACC CTCTTCGGCC GCAGGCGCTA CGTGCCCGAC
      CTCAACGCCC

2201  GGGTAAAGAG CGTGCGGGAG GCGGCGGAGC GCATGGCCTT
      TAACATGCCC

2251  GTGCAGGGCA CCGCCGCTGA CCTGATGAAG CTCGCCATGG
      TGAGGCTCTT

2301  CCCTAGGCTT CCCGAGGTGG GGGCGAGGAT GCTCCTCCAG
      GTCCACGACG

2351  AGCTCCTCCT GGAGGCGCCC AAGGAGCGGG CGGAGGAGGC
      GGCGGCCCTG

2401  GCCAAGGAGG TCATGGAGGG AGTCTGGCCC CTGGCCGTGC
      CCCTGGAGGT

2451  GGAGGTGGGC ATCGGGGAGG ACTGGCTTTC CGCCAAGGGC
      TAGTCGAC
```

In another embodiment, the invention provides a derivative nucleic acid related to *Thermus brockianus* strain YS38 having SEQ ID NO:7. A nucleic acid having SEQ ID NO:7 has GAC (encoding Asp) in place of GGC (encoding Gly) at positions 127-129 and TAC (encoding Tyr) in place of TTC (encoding Phe) at positions 1993-95.

```
   1  ATGCTTCCCC TCTTTGAGCC CAAGGGCCGG GTGCTCCTGG
      TGGACGGCCA

51  CCACCTGGCC TACCGTAACT TCTTCGCCCT CAAGGGGCTC
      ACCACGAGCC

101  GGGGCGAGCC CGTGCAAGGG GTCTACGACT TCGCCAAAAG
      CCTCCTCAAG

151  GCCCTGAAGG AGGACGGGGA CGTGGTCATC GTGGTCTTTG
      ACGCCAAGGC

201  CCCCTCTTTT CGCCACGAGG CCTACGGGGC CTACAAGGCG
      GGCCGGGCCC

251  CTACCCCGGA GGACTTTCCG AGGCAGCTTG CCCTCATGAA
      GGAGCTTGTG

301  GACCTTTTGG GGCTGGAGCG CCTCGAGGTC CCGGGCTTTG
      AGGCGGACGA

351  TGTCCTCGCC GCCCTGGCCA AGAAGGCGGA GCGGGAAGGG
      TACGAGGTGC

401  GCATCCTCAC CGCCGACCGG GACCTCTTCC AGCTTCTTTC
      GGACCGCATC

451  GCCGTCCTGC ACCCGGAAGG CCACCTCATC ACCCCGGGGT
      GGCTTTGGGA

501  GAGGTACGGC CTGAGACCGG AGCAGTGGGT GGACTTCCGC
      GCCCTGGCCG

551  GCGACCCTTC CGACAACATC CCCGGGGTGA AGGGGATCGG
      CGAGAAGACG

601  GCCCTGAAGC TCCTAAAGGA GTGGGGTAGT CTGGAAAATA
      TCCAAAAAAA

651  CCTGGACCAG GTCAGTCCCC CTTCCGTGCG CGAGAAGATC
      CAGGCCCACC
```

-continued

```
 701 TGGACGACCT CAGGCTCTCC CAGGAGCTTT CCCGGGTGCG
     CACGGACCTT
 751 CCCTTGGAGG TGGACTTTAG AAGGCGGCGG GAGCCCGATA
     GGGAAGGCCT
 801 TAGGGCCTTC TTAGAGCGGC TTGAGTTCGG GAGCCTCCTC
     CACGAGTTCG
 851 GCCTCCTGGA AAGCCCCCAG GCGGCGGAGG AGGCCCCTTG
     GCCGCCGCCG
 901 GAAGGGGCCT TCTTGGGCTT CCGCCTCTCC CGGCCCGAGC
     CCATGTGGGC
 951 GGAACTCCTT TCCTTGGCGG CAAGCGCCAA GGGCCGGGTC
     TACCGGGCGG
1001 AGGCGCCCCA TAAGGCCCTT TCGGACCTGA AGGAGATCCG
     GGGGCTTCTC
1051 GCCAAGGACC TCGCCGTCTT GGCCCTGAGG GAGGGGCTCG
     GCCTTCCCCC
1101 CACGGACGAT CCCATGCTCC TCGCCTACCT CCTGGACCCC
     TCCAACACCA
1151 CCCCCGAGGG CGTGGCCCGG CGCTACGGGG GGGAGTGGAC
     GGAGGAGGCG
1201 GGGGAGAGGG CCTTGCTTGC CGAAAGGCTT TACGAGAACC
     TCCTAAGCCG
1251 CCTGAAAGGG GAAGAAAAGC TCCTTTGGCT CTACGAGGAG
     GTGGAAAAGC
1301 CCCTTTCCCG GGTCCTCGCC CACATGGAGG CCACGGGGGT
     GAGGCTGGAC
1351 GTACCCTACC TAAGGGCCCT TTCCCTGGAG GTGGCGGCGG
     AGATGGGCCG
1401 CCTGGAGGAG GAGGTTTTCC GCCTGGCGGG CCACCCCTTC
     AACCTGAACT
1451 GCCGCGACCA GCTGGAAAGG GTGCTCTTTG ACGAGCTCGG
     GCTTCCCCCC
1501 ATCGGCAAGA CGGAAAAAAC CGGGAAGCGC TCCACCAGCG
     CCGCCGTCCT
1551 CGAGGCCCTG CGGGAGGCCC ACCCCATCGT GGAGAAGATC
     CTCCAGTACC
1601 GCGAGCTCGC CAAGCTCAAG GGCACCTACA TTGACCTCCT
     TCCCGCCCTG
1651 GTCCACCCCA GGACGGGCAG GCTCCACACC CGCTTCAACC
     AGACGGCCAC
1701 GGCCACGGGC CGCCTTTCCA GCTCCGACCC CAACCTGCAG
     AACATTCCCG
1751 TGCGCACCCC CTTGGGCCAA AGGATCCGCC GGGCCTTCGT
     GGCCGAGGAG
1801 GGGTACCTTC TCGTGGCCCT GGACTATAGC CAGATTGAGC
     TGAGGGTCCT
1851 GGCCCACCTC TCGGGGGACG AAAACCTCAT CCGGGTCTTC
     CAGGAGGGCC
1901 GGGACATCCA CACCCAGACG GCGAGCTGGA TGTTCGGCCT
     GCCGGCGGAG
1951 GCCATAGACC CCCTCAGGCG CCGGGCGGCC AAGACCATCA
     ACTACGGCGT
2001 CCTCTACGGC ATGTCCGCCC ACCGGCTTTC CCAGGAGCTG
     GGCATCCCCT
2051 ACGAGGAGGC GGTGGCCTTC ATTGACCGCT ATTTCCAGAG
     CTACCCCAAG
2101 GTGAAGGCCT GGATTGAAAG GACCCTGGAG GAGGGGCGGC
     AAAGGGGGTA
2151 CGTGGAGACC CTCTTCGGCC GCAGGCGCTA CGTGCCCGAC
     CTCAACGCCC
2201 GGGTAAAGAG CGTGCGGGAG GCGGCGGAGC GCATGGCCTT
     TAACATGCCC
2251 GTGCAGGGCA CCGCCGCTGA CCTGATGAAG CTCGCCATGG
     TGAGGCTCTT
2301 CCCTAGGCTT CCCGAGGTGG GGGCGAGGAT GCTCCTCCAG
     GTCCACGACG
2351 AGCTCCTCCT GGAGGCGCCC AAGGAGCGGG CGGAGGAGGC
     GGCGGCCCTG
2401 GCCAAGGAGG TCATGGAGGG GGTCTGGCCC CTGGCCGTGC
     CCCTGGAGGT
2451 GGAGGTGGGC ATCGGGGAGG ACTGGCTTTC CGCCAAGGGC
     TAG
```

In another embodiment, the invention provides a derivative nucleic acid related to *Thermus brockianus* strain 2AZN having SEQ ID NO:8. A nucleic acid having SEQ ID NO:8 has GAC (encoding Asp) in place of GGC (encoding Gly) at positions 127-129 and TAC (encoding Tyr) in place of TTC (encoding Phe) at positions 1993-95.

```
   1 ATGCTTCCCC TCTTTGAGCC CAAGGGCCGG GTGCTCCTGG
     TGGACGGCCA
  51 CCACCTGGCC TACCGTAACT TCTTCGCCCT CAAGGGGCTC
     ACCACGAGCC
 101 GGGGCGAGCC CGTGCAAGGG GTCTACGACT TCGCCAAAAG
     CCTCCTCAAG
 151 GCCCTGAAGG AGGACGGGGA CGTGGTCATC GTGGTCTTTG
     ACGCCAAGGC
 201 CCCCTCTTTT CGCCACGAGG CCTACGGGGC CTACAAGGCG
     GGCCGGGCCC
 251 CTACCCCGGA GGACTTTCCG AGGCAGCTTG CCCTCATGAA
     GGAGCTTGTG
 301 GACCTTTTGG GGCTGGAGCG CCTCGAGGTC CCGGGCTTTG
     AGGCGGACGA
 351 TGTCCTCGCC GCCCTGGCCA AGAAGGCGGA GCGGGAAGGG
     TACGAGGTGC
 401 GCATCCTCAC CGCCGACCGG GACCTCTTCC AGCTTCTTTC
     GGACCGCATC
 451 GCCGTCCTGC ACCCGGAAGG CCACCTCATC ACCCCGGGGT
     GGCTTTGGGA
 501 GAGGTACGGC CTGAGACCGG AGCAGTGGGT GGACTTCCGC
     GCCCTGGCCG
 551 GCGACCCTTC CGACAACATC CCCGGGGTGA AGGGGATCGG
     CGAGAAGACG
 601 GCCCTGAAGC TCCTAAAGGA GTGGGGTAGT CTGGAAAATA
     TCCAAAAAAA
 651 CCTGGACCAG GTCAGTCCCC CTTCCGTGCG CGAGAAGATC
     CAGGCCCACC
```

```
701  TGGACGACCT CAGGCTCTCC CAGGAGCTTT CCCGGGTGCG
     CACGGACCTT

751  CCCTTGGAGG TGGACTTTAG AAGGCGGCGG GAGCCCGATA
     GGGAAGGCCT

801  TAGGGCCTTC TTAGAGCGGC TTGAGTTCGG GAGGCTCCTC
     CACGAGTTCG

851  GCCTCCTGGA AAGCCCCCAG GCGGCGGAGG AGGCCCCTTG
     GCCGCCGCCG

901  GAAGGGGCCT TCTTGGGCTT CCGCCTCTCC CGGCCCGAGC
     CCATGTGGGC

951  GGAACTCCTT TCCTTGGCGG CAAGGGCCAA GGGCCGGGTC
     TACCGGGCGG

1001 AGGCGCCCCA TAAGGCCCTT TCGGACCTGA AGGAGATCCG
     GGGGCTTCTC

1051 GCCAAGGACC TCGCCGTCTT GGCCCTGAGG GAGGGGCTCG
     GCCTTCCCCC

1101 CACGGACGAT CCCATGCTCC TCGCCTACCT CCTGGACCCC
     TCCAACACCA

1151 CCCCCGAGGG CGTGGCCCGG CGCTACGGGG GGGAGTGGAC
     GGAGGAGGCG

1201 GGGGAGAGGG CCTTGCTTGC CGAAAGGCTT TACGAGAACC
     TCCTAAGCCG

1251 CCTGAAAGGG GAAGAAAAGC TCCTTTGGCT CTACGAGGAG
     GTGGAAAAGC

1301 CCCTTTCCCG GGTCCTCGCC CACATGGAGG CCACGGGGGT
     GAGGCTGGAC

1351 GTACCCTACC TAAGGGCCCT TTCCCTGGAG GTGGCGGCGG
     AGATGGGCCG

1401 CCTGGAGGAG GAGGTTTTCC GCCTGGCGGG CCACCGCTTC
     AACCTGAACT

1451 CCCGCGACCA GCTGGAAAGG GTGCTCTTTG ACGAGCTCGG
     GCTTCCCCCC

1501 ATCGGCAAGA CGGAAAAAAC CGGGAAGCGC TCCACCAGCG
     CGGCCGTCCT

1551 CGAGGCCCTG CGGGAGGCCC ACCCCATCGT GGAGAAGATC
     CTCCAGTACC

1601 GGGAGCTCGC CAAGCTCAAG GGCACCTACA TTGACCCCCT
     TCCCGCCCTG

1651 GTCCACCCCA GGACGGGCAG GCTCCACACC CGCTTCAACC
     AGACGGCCAC

1701 GGCCACGGGC CGCCTTTCCA GCTCCGACCC CAACCTGCAG
     AACATTCCCG

1751 TGCGCACCCC CTTGGGCCAA AGGATCCGCC GGGCCTTCGT
     GGCCGAGGAG

1801 GGGTACCTTC TCGTGGCCCT GGACTATAGC CAGATTGAGC
     TGAGGGTCCT

1851 GGCCCACCTC TCGGGGACG AAAACCTCAT CCGGGTCTTC
     CAGGAGGGCC

1901 GGGACATCCA CACCCAGACG GCGAGCTGGA TGTTCGGCCT
     GCCGGCGGAG

1951 GCCATAGACC CCCTCAGGCG CCGGGCGGCC AAGACCATCA
     ACTACGGCGT

2001 CCTCTACGGC ATGTCCGCCC ACCGGCTTTC CCAGGAGCTG
     GGCATCCCCT

2051 ACGAGGAGGC GGTGGCCTTC ATTGACCGCT ATTTCCAGAG
     CTACCCCAAG

2101 GTGAAGGCCT GGATTGAAAG GACCCTGGAG GAGGGCGGC
     AAAGGGGGTA

2151 CGTGGAGACC CTCTTCGGCC GCAGGCGCTA CGTGCCCGAC
     CTCAACGCCC

2201 GGGTAAAGAG CGTGCGGGAG GCGGCGGAGC GCATGGCCTT
     TAACATGCCC

2251 GTGCAGGGCA CCGCCGCTGA CCTGATGAAG CTCGCCATGG
     TGAGGCTCTT

2301 CCCTAGGCTT CCCGAGGTGG GGGCGAGGAT GCTGCTCCAG
     GTCCACGACG

2351 AGCTCCTCCT GGAGGCGCCC AAGGAGCGGG CGGAGGAGGC
     GGCGGCCCTG

2401 GCCAAGGAGG TCATGGAGGG AGTCTGGCCC CTGGCCGTGC
     CCCTGGAGGT

2451 GGAGGTGGGC ATCGGGAGG ACTGGCTTTC CGCCAAGGGC
     TAGTCGAC
```

The substitution of TAC (encoding Tyr) for TTC (encoding Phe) at the indicated positions can reduce discrimination against ddNTP incorporation by DNA polymerase I. See, e.g., U.S. Pat. No. 5,614,365, which is incorporated herein by reference. The substitution of GAC (encoding Asp) for GGG (encoding Gly) at the indicated positions removes the 5'-3' exonuclease activity.

The nucleic acids of the invention have homology to portions of the DNA sequences encoding the thermostable DNA polymerases of *Thermus aquaticus* and *Thermus thermophilus* (see FIG. 1). However, significant portions of the nucleic acid sequences of the present invention are distinct.

The invention also encompasses fragment and variant nucleic acids of SEQ ID NO:1-8. Nucleic acid "fragments" encompassed by the invention are of two general types. First, fragment nucleic acids that do not encode a full length DNA polymerase but do encode a thermally stable polypeptide with DNA polymerase activity are encompassed within the invention. Second, fragment nucleic acids useful as hybridization probes but that generally do not encode polymerases retaining biological activity are also encompassed within the invention. Thus, fragments of nucleotide sequences such as SEQ ID NO:1-8 may be as small as about 9 nucleotides, about 12 nucleotides, about 15 nucleotides, about 17 nucleotides, about 18 nucleotides, about 20 nucleotides, about 50 nucleotides, about 100 nucleotides or more. In general, a fragment nucleic acid of the invention can have any upper size limit so long as it is related in sequence to the nucleic acids of the invention but is not full length.

As indicated above, "variants" are substantially similar or substantially homologous sequences. For nucleotide sequences, variants include those sequences that, because of the degeneracy of the genetic code, encode the identical amino acid sequence of the native DNA polymerase I protein. Variant nucleic acids also include those that encode polypeptides that do not have amino acid sequences identical to that of a native DNA polymerase I protein, but that encode an active, thermally stable DNA polymerase I with conservative changes in the amino acid sequence.

As is known by one of skill in the art, the genetic code is "degenerate," meaning that several trinucleotide codons can encode the same amino acid. This degeneracy is apparent from Table 1.

TABLE 1

| 1st Position | Second Position | | | | 3rd Position |
| --- | --- | --- | --- | --- | --- |
| | T | C | A | G | |
| T | TTT = Phe | TCT = Ser | TAT = Tyr | TGT = Cys | T |
| T | TTC = Phe | TCC = Ser | TAC = Tyr | TGC = Cys | C |
| T | TTA = Leu | TCA = Ser | TAA = Stop | TGA = Stop | A |
| T | TTG = Leu | TCG = Ser | TAG = Stop | TGG = Trp | G |
| C | CTT = Leu | CCT = Pro | CAT = His | CGT = Arg | T |
| C | CTC = Leu | CCC = Pro | CAC = His | CGC = Arg | C |
| C | CTA = Leu | CCA = Pro | CAA = Gln | CGA = Arg | A |
| C | CTG = Leu | CCG = Pro | CAG = Gln | CGG = Arg | G |
| A | ATT = Ile | ACT = Thr | AAT = Asn | AGT = Ser | T |
| A | ATC = Ile | ACC = Thr | AAC = Asn | AGC = Ser | C |
| A | ATA = Ile | ACA = Thr | AAA = Lys | AGA = Arg | A |
| A | ATG = Met | ACG = Thr | AAG = Lys | AGG = Arg | G |
| G | GTT = Val | GCT = Ala | GAT = Asp | GGT = Gly | T |
| G | GTC = Val | GCC = Ala | GAC = Asp | GGC = Gly | C |
| G | GTA = Val | GCA = Ala | GAA = Gln | GGA = Gly | A |
| G | GTG = Val | GCG = Ala | GAG = Gln | GGG = Gly | G |

Hence, many changes in the nucleotide sequence of the variant may be silent and may not alter the amino acid sequence encoded by the nucleic acid. Where nucleic acid sequence alterations are silent, a variant nucleic acid will encode a polypeptide with the same amino acid sequence as the reference nucleic acid. Therefore, a particular nucleic acid sequence of the invention also encompasses variants with degenerate codon substitutions, and complementary sequences thereof, as well as the sequence explicitly specified by a SEQ ID NO. Specifically, degenerate codon substitutions may be achieved by generating sequences in which the reference codon is replaced by any of the codons for the amino acid specified by the reference codon. In general, the third position of one or more selected codons can be substituted with mixed-base and/or deoxyinosine residues as disclosed by Batzer et al., Nucleic Acid Res., 19, 5081 (1991) and/or Ohtsuka et al., J. Biol. Chem., 260, 2605 (1985); Rossolini et al., Mol. Cell. Probes, 8, 91 (1994).

However, the invention is not limited to silent changes in the present nucleotide sequences but also includes variant nucleic acid sequences that conservatively alter the amino acid sequence of a polypeptide of the invention. According to the present invention, variant and reference nucleic acids of the invention may differ in the encoded amino acid sequence by one or more substitutions, additions, insertions, deletions, fusions and truncations, which may be present in any combination, so long as an active, thermally stable DNA polymerase is encoded by the variant nucleic acid. Such variant nucleic acids will not encode exactly the same amino acid sequence as the reference nucleic acid, but have conservative sequence changes.

Variant nucleic acids with silent and conservative changes can be defined and characterized by the degree of homology to the reference nucleic acid. Preferred variant nucleic acids are "substantially homologous" to the reference nucleic acids of the invention. As recognized by one of skill in the art, such substantially similar nucleic acids can hybridize under stringent conditions with the reference nucleic acids identified by SEQ ID NOs herein. These types of substantially homologous nucleic acids are encompassed by this invention.

Generally, nucleic acid derivatives and variants of the invention will have at least 90%, 91%, 92%, 93% or 94% sequence identity to the reference nucleotide sequence defined herein. Preferably, nucleic acids of the invention will have at least at least 95%, 96%, 97%, 98%, or 99% sequence identity to the reference nucleotide sequence defined herein.

Variant nucleic acids can be detected and isolated by standard hybridization procedures.

Hybridization to detect or isolate such sequences is generally carried out under stringent conditions. "Stringent hybridization conditions" and "stringent hybridization wash conditions" in the context of nucleic acid hybridization experiments such as Southern and Northern hybridization are sequence dependent, and are different under different environmental parameters. Longer sequences hybridize specifically at higher temperatures. An extensive guide to the hybridization of nucleic acids is found in Tijssen, Laboratory Techniques in Biochemistry and Molecular biology-Hybridization with Nucleic Acid Probes, page 1, chapter 2 "Overview of principles of hybridization and the strategy of nucleic acid probe assays" Elsevier, N.Y. (1993). See also, J. Sambrook et al., Molecular Cloning: A Laboratory Manual, Cold Spring Harbor Press, N.Y., pp 9.31-9.58 (1989); J. Sambrook et al., Molecular Cloning: A Laboratory Manual, Cold Spring Harbor Press, N.Y. (3rd ed. 2001).

The invention also provides methods for detection and isolation of derivative or variant nucleic acids encoding DNA polymerase I activity. The methods involve hybridizing at least a portion of a nucleic acid comprising SEQ ID NO:1, 2, 3, 4, 5, 6, 7 or 8 to a sample nucleic acid, thereby forming a hybridization complex; and detecting the hybridization complex. The presence of the complex correlates with the presence of a derivative or variant nucleic acid encoding at least a segment of DNA polymerase I. In general, the portion of a nucleic acid comprising SEQ ID NO: 1, 2, 3, 4, 5, 6, 7 or 8 used for hybridization is at least fifteen nucleotides, and hybridization is under hybridization conditions that are sufficiently stringent to permit detection and isolation of substantially homologous nucleic acids. In an alternative embodiment, a nucleic acid sample is amplified by the polymerase chain reaction using primer oligonucleotides selected from SEQ ID NO: 1, 2, 3, 4, 5, 6, 7 or 8.

Generally, highly stringent hybridization and wash conditions are selected to be about 5° C. lower than the thermal melting point ($T_m$) for the specific double-stranded sequence at a defined ionic strength and pH. For example, under "highly stringent conditions" or "highly stringent hybridization conditions" a nucleic acid will hybridize to its complement to a detectably greater degree than to other sequences (e.g., at least 2-fold over background). By controlling the stringency of the hybridization and/or washing conditions, nucleic acids that are 100% complementary can be identified.

Alternatively, stringency conditions can be adjusted to allow some mismatching in sequences so that lower degrees of similarity are detected (heterologous probing). Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide.

Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl and 0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

The degree of complementarity or homology of hybrids obtained during hybridization is typically a function of post-hybridization washes, the critical factors being the ionic strength and temperature of the final wash solution. The type and length of hybridizing nucleic acids also affects whether hybridization will occur and whether any hybrids formed will be stable under a given set of hybridization and wash conditions. For DNA-DNA hybrids, the $T_m$ can be approximated from the equation of Meinkoth and Wahl Anal. Biochem. 138:267-284 (1984); $T_m$ 81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe.

Very stringent conditions are selected to be equal to the $T_m$ for a particular probe.

An example of stringent hybridization conditions for hybridization of complementary nucleic acids that have more than 100 complementary residues on a filter in a Southern or Northern blot is 50% formamide with 1 mg of heparin at 42° C., with the hybridization being carried out overnight. An example of highly stringent conditions is 0.15 M NaCl at 72° C. for about 15 minutes. An example of stringent wash conditions is a 0.2×SSC wash at 65° C. for 15 minutes (see also, Sambrook, infra). Often, a high stringency wash is preceded by a low stringency wash to remove background probe signal. An example of medium stringency for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0M Na ion, typically about 0.01 to 1.0 M Na ion concentration (or other salts) at pH 7.0 to 8.3, and the temperature is typically at least about 30° C.

Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

The following are examples of sets of hybridization/wash conditions that may be used to detect and isolate homologous nucleic acids that are substantially identical to reference nucleic acids of the present invention: a reference nucleotide sequence preferably hybridizes to the reference nucleotide sequence in 7% sodium dodecyl sulfate (SDS), 0.5 M NaPO$_4$, 1 mM EDTA at 50° C. with washing in 2×SSC, 0.1% SDS at 50° C., more desirably in 7% sodium dodecyl sulfate (SDS), 0.5 M NaPO$_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1×SSC, 0.1% SDS at 65° C.

In general, $T_m$ is reduced by about 1° C. for each 1% of mismatching. Thus, $T_m$, hybridization, and/or wash conditions can be adjusted to hybridize to sequences of the desired sequence identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$).

If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) Laboratory Techniques in Biochemistry and Molecular Biology-Hybridization with Nucleic Acid Probes, Part 1, Chapter 2 (Elsevier, N.Y.); and Ausubel et al., eds. (1995) Current Protocols in Molecular Biology, Chapter 2 (Greene Publishing and Wiley-Interscience, New York). See Sambrook et al. (1989) Molecular Cloning: A Laboratory Manual (2d ed., Cold Spring Harbor Laboratory Press, Plainview, N.Y.). Using these references and the teachings herein on the relationship between $T_m$, mismatch, and hybridization and wash conditions, those of ordinary skill can generate variants of the present DNA polymerase I nucleic acids.

Computer analyses can also be utilized for comparison of sequences to determine sequence identity. Such analyses include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. Gene 73:237 244 (1988); Higgins et al. CABIOS 5:151-153 (1989); Corpet et al. Nucleic Acids Res. 16:10881-90 (1988); Huang et al. CABIOS 8:155-65 (1992); and Pearson et al. Meth. Mol. Biol. 24:307-331 (1994). The ALIGN program is based on the algorithm of Myers and Miller, supra. The BLAST programs of Altschul et al., J. Mol. Biol. 215:403 (1990), are based on the algorithm of Karlin and Altschul supra. To obtain gapped alignments for comparison purposes, Gapped BLAST (in BLAST 2.0) can be utilized as described in Altschul et al. Nucleic Acids Res. 25:3389 (1997). Alternatively, PSI-BLAST (in BLAST 2.0) can be used to perform an iterated search that detects distant relationships between molecules. See Altschul et al., supra. When utilizing BLAST, Gapped BLAST, PSI-BLAST, the default parameters of the respective programs (e.g. BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, Proc. Natl. Acad. Sci. USA, 89, 10915 (1989)). See http://www.ncbi.nlm.nih.gov. Alignment may also be performed manually by inspection.

For purposes of the present invention, comparison of nucleotide sequences for determination of percent sequence identity to the DNA polymerase sequences disclosed herein is preferably made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

Expression of Polymerase Nucleic Acids

Nucleic acids of the invention may be used for the recombinant expression of the polymerase polypeptides of the invention. Generally, recombinant expression of a polymerase polypeptide of the invention is effected by introducing a nucleic acid encoding that polypeptide into an expression vector adapted for use in particular type of host cell. The nucleic acids of the invention can be introduced and expressed in any host organism, for example, in both prokaryotic or eukaryotic host cells. Examples of host cells include bacterial cells, yeast cells, cultured insect cell lines, and cultured mammalian cells lines. Preferably, the recombinant host cell system is selected that processes and post-translationally modifies nascent polypeptides in a manner similar to that of the organism from which the polymerase was derived. For purposes of expressing and isolating polymerase polypeptides of the invention, prokaryotic organisms are preferred, for example, *Escherichia coli*. Accordingly, the invention provides host cells comprising the expression vectors of the invention.

The nucleic acids to be introduced can be conveniently placed in expression cassettes for expression in an organism of interest. Such expression cassettes will comprise a transcriptional initiation region linked to a nucleic acid of the invention. Expression cassettes preferably also have a plurality of restriction sites for insertion of the nucleic acid to be under the transcriptional regulation of various control elements. The expression cassette additionally may contain selectable marker genes. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc., or a combination of both endogenous and exogenous control elements.

Preferably the nucleic acid in the vector is under the control of, and operably linked to, an appropriate promoter or other regulatory elements for transcription in a host cell. The vector may be a bi-functional expression vector that functions in multiple hosts. The transcriptional cassette generally includes in the 5'-3' direction of transcription, a promoter, a transcriptional and translational initiation region, a DNA sequence of interest, and a transcriptional and translational termination region functional in the organism. The termination region may be native with the transcriptional initiation region, may be native with the DNA sequence of interest, or may be derived from another source.

Efficient expression of recombinant DNA sequences in prokaryotic and eukaryotic cells generally requires regulatory control elements directing the efficient termination and polyadenylation of the resulting transcript. Transcription termination signals are generally found downstream of the polyadenylation signal and are a few hundred nucleotides in length. The term "poly A site" or "poly A sequence" as used herein denotes a DNA sequence that directs both the termination and polyadenylation of the nascent RNA transcript. Efficient polyadenylation of the recombinant transcript is desirable as transcripts lacking a poly A tail are unstable and are rapidly degraded.

Nucleic acids encoding DNA polymerase I may be introduced into bacterial host cells by a method known to one of skill in the art. For example, nucleic acids encoding a thermophilic DNA polymerase I can be introduced into bacterial cells by commonly used transformation procedures such as by treatment with calcium chloride or by electroporation. If the thermophilic DNA polymerase I is to be expressed in eukaryotic host cells, nucleic acids encoding the thermophilic DNA polymerase I may be introduced into eukaryotic host cells by a number of means including calcium phosphate co-precipitation, spheroplast fusion, electroporation and the like. When the eukaryotic host cell is a yeast cell, transformation may be affected by treatment of the host cells with lithium acetate or by electroporation.

Thus, one aspect of the invention is to provide expression vectors and host cells comprising a nucleic acid encoding a DNA polymerase polypeptide of the invention. A range of expression vectors are available in the art. Description of various expression vectors and how to use them can be found among other places in U.S. Pat. Nos. 5,604,118; 5,583,023; 5,432,082; 5,266,490; 5,063,158; 4,966,841; 4,806,472; 4,801,537; and Goedel et al., Gene Expression Technology, Methods of Enzymology, Vol. 185, Academic Press, San Diego (1989). The expression of polymerases in recombinant cell systems is an established technique. Examples of the recombinant expression of DNA polymerase can be found in U.S. Pat. Nos. 5,602,756; 5,545,552; 5,541,311; 5,500,363; 5,489,523; 5,455,170; 5,352,778; 5,322,785; and 4,935,361.

Recombinant DNA and molecular cloning techniques that can be used to help make and use aspects of the invention are described by Sambrook et al., Molecular Cloning: A Laboratory Manual Vol. 1-3, Cold Spring Harbor laboratory, Cold Spring Harbor, N.Y. (2001); Ausubel (ed.), Current Protocols in Molecular Biology, John Wiley and Sons, Inc. (1994); T. Maniatis, E. F. Fritsch and J. Sambrook, Molecular Cloning: A Laboratory Manual, Cold Spring Harbor laboratory, Cold Spring Harbor, N.Y. (1989); and by T. J. Silhavy, M. L. Berman, and L. W. Enquist, Experiments with Gene Fusions, Cold Spring Harbor Laboratory, Cold Spring Harbor, N.Y. (1984).

Nucleic Acid Polymerases

The invention provides *Thermus brockianus* polymerase polypeptides, as well as fragments thereof and variant polymerase polypeptides that are active and thermally stable. Any polypeptide containing amino acid sequence SEQ ID NO:9, SEQ ID NO:10, SEQ ID NO:11, SEQ ID NO:12, SEQ ID NO:13, SEQ ID NO:14, SEQ ID NO:15 and SEQ ID NO:16, which are the amino acid sequences for wild type and derivative *Thermus brockianus* polymerases, are contemplated by the present invention. The polypeptides of the invention are isolated or substantially purified polypeptides. In particular, the isolated polypeptides of the invention are substantially free of proteins normally present in *Thermus brockianus* bacteria.

In one embodiment, the invention provides a wild type *Thermus brockianus* polymerase from strain YS38 having SEQ ID NO:9.

```
  1 MLPLFEPKGR VLLVDGHHLA YRNFFALKGL TTSRGEPVQG    50
    VYGFAKSLLK

51 ALKEDGDVVI VVFDAKAPSF RHEAYGAYKA GRAPTPEDFP   100
    RQLALMKELV

101 DLLGLERLEV PGFEADDVLA ALAKKAEREG YEVRILTADR   150
    DLFQLLSDRI

151 AVLHPEGHLI TPGWLWERYG LRPEQWVDFR ALAGDPSDNI   200
    PGVKGIGEKT

201 ALKLLKEWGS LENIQKNLDQ VSPPSVREKI QAHLDDLRLS   250
    QELSRVRTDL

251 PLEVDFRRRR EPDREGLRAF LERLEFGSLL HEFGLLESPQ   300
    AAEEAPWPPP

301 EGAFLGFRLS RPEPMWAELL SLAASAKGRV YRAEAPHKAL   350
    SDLKEIRGLL

351 AKDLAVLALR EGLGLPPTDD PMLLAYLLDP SNTTPEGVAR   400
    RYGGEWTEEA

401 GERALLAERL YENLLSRLKG EEKLLWLYEE VEKPLSRVLA   450
    HMEATGVRLD

451 VPYLRALSLE VAAEMGRLEE EVFRLAGHPF NLNSRDQLER   500
    VLFDELGLPP

501 IGKTEKTGKR STSAAVLEAL REARPIVEKI LQYRELAKLK   550
    GTYIDLLPAL

551 VHPRTGRLHT RFNQTATATG RLSSSDPNLQ NIPVRTPLGQ   600
    RIRRAFVAEE

601 GYLLVALDYS QIELRVLAHL SGDENLIRVF QEGRDIHTQT   650
    ASWMFGLPAE

651 AIDPLRRRAA KTINFGVLYG MSAHRLSQEL GIPYEEAVAF   700
    IDRYFQSYPK

701 VKAWIERTLE EGRQRGYVET LFGRRRYVPD LNARVKSVRE   750
    AAERMAFNMP

751 VQGTAADLMK LAMVRLFPRL PEVGARMLLQ VHDELLLEAP   800
    KERAEEAAAL

801 AKEVMEGVWP LAVPLEVEVG IGEDWLSAKG               829
```

In another embodiment, the invention provides a wild type *Thermus brockianus* polymerase from strain 2AZN having SEQ ID NO:10. The 2AZN amino acid sequence differs from the YS38 sequence by one amino acid—the 2AZN strain has proline instead of leucine at position 546.

```
  1 MLPLFEPKGR VLLVDGHHLA YRNFFALKGL TTSRGEPVQG    50
    VYGFAKSLLK

51 ALKEDGDVVI VVFDAKAPSF RHEAYGAYKA GRAPTPEDFP   100
    RQLALMKELV

101 DLLGLERLEV PGFEADDVLA ALAKKAEREG YEVRILTADR   150
    DLFQLLSDRI

151 AVLHPEGHLI TPGWLWERYG LRPEQWVDFR ALAGDPSDNI   200
    PGVKGIGEKT

201 ALKLLKEWGS LENIQKNLDQ VSPPSVREKI QAHLDDLRLS   250
    QELSRVRTDL

251 PLEVDFRRRR EPDREGLRAF LERLEFGSLL HEFGLLESPQ   300
    AAEEAPWPPP

301 EGAFLGFRLS RPEPMWAELL SLAASAKGRV YRAEAPHKAL   350
    SDLKEIRGLL

351 AKDLAVLALR EGLGLPPTDD PMLLAYLLDP SNTTPEGVAR   400
    RYGGEWTEEA

401 GERALLAERL YENLLSRLKG EEKLLWLYEE VEKPLSRVLA   450
    HMEATGVRLD

451 VPYLRALSLE VAAEMGRLEE EVFRLAGHPF NLNSRDQLER   500
    VLFDELGLPP

501 IGKTEKTGKR STSAAVLEAL REAHPIVEKI LQYRELAKLK   550
    GTYIDPLPAL

551 VHPRTGRLHT RFNQTATATG RLSSSDPNLQ NIPVRTPLGQ   600
    RIRRAFVAEE

601 GYLLVALDYS QIELRVLAHL SGDENLIRVF QEGRDIHTQT   650
    ASWMFGLPAE

651 AIDPLRRRAA KTINFGVLYG MSAHRLSQEL GIPYEEAVAF   700
    IDRYFQSYPK

701 VKAWIERTLE EGRQRGYVET LFGRRRYVPD LNARVKSVRE   750
    AAERMAFNMP

751 VQGTAADLMK LAMVRLFPRL PEVGARMLLQ VHDELLLEAP   800
    KERAEEAAAL

801 AKEVMEGVWP LAVPLEVEVG IGEDWLSAKG               829
```

Significant portions of the *Thermus brockianus* polymerase sequences are distinct from other polymerases, including, for example, a peptide at positions 22-25 (RNFF, SEQ ID NO:50, a peptide at positions 39-42 (QGVY, SEQ ID NO:17), a peptide at positions 76-79 (GAYK, SEQ ID NO:18), a peptide at positions 95-98 (LMKE, SEQ ID NO:19), a peptide at positions 111-114 (PGFE, SEQ ID NO:20), a peptide at positions 106-121 (ERLEVPGFEADD VLAA, SEQ ID NO:21), a peptide at positions 161-164 (TPGW, SEQ ID NO:22), a peptide at positions 182-186 (LAGDP, SEQ ID NO:23), a peptide at positions 213-216 (NIQK, SEQ ID NO:24), a peptide at positions 220-224 (QVSPP, SEQ ID NO:25), a peptide at positions 228-231 (EKIQ, SEQ ID NO:26), a peptide at positions 238-242 (RLSQE, SEQ ID NO:27), a peptide at positions 256-261 (FRRRRE, SEQ ID NO:28), a peptide at positions 288-292 (SPQAA, SEQ ID NO:29), a peptide at positions 305-308 (LGFR, SEQ ID NO:30), a peptide at positions 318-321 (ELLS, SEQ ID NO:31), a peptide at positions 325-331 (SAKGRVY, SEQ ID NO:32), a peptide at positions 334-337 (EAPH, SEQ ID NO:33), a peptide at positions 334-341 (EAPHKALS, SEQ ID NO:34), a peptide at positions 407-412 (AERLYE, SEQ ID NO:35), a peptide at positions 415-419 (LSRLK, SEQ ID NO:36), a peptide at positions 428-431 (YEEV, SEQ ID NO:37), a peptide at positions 465-468 (MGRL, SEQ ID NO:38), a peptide at positions 537-541

(AKLKG, SEQ ID NO:39), a peptide at positions 545-549 (LPAL, SEQ ID NO:40), a peptide at positions 600-603 (EGYL, SEQ ID NO:41), a peptide at positions 647-650 (LPAE, SEQ ID NO:42), a peptide at positions 648-652 (PAEAI, SEQ ID NO:43), a peptide at positions 655-658 (LRRR, SEQ ID NO:44), a peptide at positions 690-693 (IDRY, SEQ ID NO:45), a peptide at positions 698-702 (YP-KVK, SEQ ID NO:46), a peptide at positions 712-715 (GRQR, SEQ ID NO:47), a peptide at positions 765-773 (RLFPRLPEV, SEQ ID NO:48) and a peptide at positions 807-810 (GVWP, SEQ ID NO:49).

Many DNA polymerases possess activities in addition to a DNA polymerase activity. Such activities include, for example, a 5'-3' exonuclease activity and/or a 3'-5' exonuclease activity. The 3'-5' exonuclease activity improves the accuracy of the newly-synthesized strand by removing incorrect bases that may have been incorporated. DNA polymerases in which such activity is low or absent are prone to errors in the incorporation of nucleotide residues into the primer extension strand. Taq DNA polymerase has been reported to have low 3'-5' exonuclease activity. See Lawyer et al., J. Biol. Chem. 264:6427-6437. In applications such as nucleic acid amplification procedures in which the replication of DNA is often geometric in relation to the number of primer extension cycles, such errors can lead to serious artifactual problems such as sequence heterogeneity of the nucleic acid amplification product (amplicon). Thus, a 3'-5' exonuclease activity is a desired characteristic of a thermostable DNA polymerase used for such purposes.

By contrast, the 5'-3' exonuclease activity of DNA polymerase enzymes is often undesirable because this activity may digest nucleic acids, including primers, which have an unprotected 5' end. Thus, a thermostable polymerase with an attenuated 5'-3' exonuclease activity, or in which such activity is absent, is a desired characteristic of an enzyme for biochemical applications. Various DNA polymerase enzymes have been described where a modification has been introduced in a DNA polymerase that accomplishes this object. For example, the Klenow fragment of *E. coli* DNA polymerase I can be produced as a proteolytic fragment of the holoenzyme in which the domain of the protein controlling the 5'-3' exonuclease activity has been removed. The Klenow fragment still retains the polymerase activity and the 3'-5' exonuclease activity. Barnes, PCT Publication No. WO92/06188 (1992) and Gelfand et al., U.S. Pat. No. 5,446,591 have produced 5'-3' exonuclease-deficient recombinant *Thermus aquaticus* DNA polymerases. Ishino et al., EPO Publication No. 0517418A2, have produced a 5'-3' exonuclease-deficient DNA polymerase derived from *Bacillus caldotenax*.

In another embodiment, the invention provides a polypeptide that is a derivative *Thermus brockianus* polypeptide with reduced or eliminated 5'-3' exonuclease activity. Several methods exist for reducing this activity, and the invention contemplates any polypeptide derived from the *Thermus brockianus* polypeptides of the invention that has reduced or eliminated such 5'-3' exonuclease activity. Xu et al., *Biochemical and mutational studies of the 5'-3' exonuclease of DNA polymerase I of Escherichia coli*, J. Mol. Biol. 1997 May 2; 268(2):284-302. In one embodiment, Asp is used in place of Gly at position 43 to produce a polypeptide with reduced 5'-3' exonuclease activity.

Hence, the invention provides a derivative polypeptide having SEQ ID NO:11 that is related to a *Thermus brockianus* polypeptide polypeptide from strain YS38, wherein Asp is used in place of Gly at position 43.

```
  1 MLPLFEPKGR VLLVDGHHLA YRNFFALKGL TTSRGEPVQG    50
    VYDFAKSLLK

51 ALKEDGDVVI VVFDAKAPSF RHEAYGAYKA GRAPTPEDFP   100
    RQLALMKELV

101 DLLGLERLEV PGFEADDVLA ALAKKAEREG YEVRILTADR   150
    DLFQLLSDRI

151 AVLHPEGHLI TPGWLWERYG LRPEQWVDFR ALAGDPSDNI   200
    PGVKGIGEKT

201 ALKLLKEWGS LENIQKNLDQ VSPPSVREKI QAHLDDLRLS   250
    QELSRVRTDL

251 PLEVDFRRRR EPDREGLRAF LERLEFGSLL HEFGLLESPQ   300
    AAEEAPWPPP

301 EGAFLGFRLS RPEPMWAELL SLAASAKGRV YRAEAPHKAL   350
    SDLKEIRGLL

351 AKDLAVLALR EGLGLPPTDD PMLLAYLLDP SNTTPEGVAR   400
    RYGGEWTEEA

401 GERALLAERL YENLLSRLKG EEKLLWLYEE VEKPLSRVLA   450
    HMEATGVRLD

451 VPYLRALSLE VAAEMGRLEE EVFRLAGHPF NLNSRDQLER   500
    VLFDELGLPP

501 IGKTEKTGKR STSAAVLEAL REAHPIVEKI LQYRELAKLK   550
    GTYIDLLPAL

501 VHPRTGRLHT RFNQTATATG RLSSSDPNLQ NIPVRTPLGQ   600
    RIRRAFVAEE

601 GYLLVALDYS QIELRVLAHL SGDENLIRVF QEGRDIHTQT   650
    ASWMFGLPAE

651 AIDPLRRRAA KTINFGVLYG MSAHRLSQEL GIPYEEAVAF   700
    IDRYFQSYPK

701 VKAWIERTLE EGRQRGYVET LFGRRRYVPD LNARVKSVRE   750
    AAERMAFNMP

751 VQGTAADLMK LAMVRLFPRL PEVGARMLLQ VHDELLLEAP   800
    KERAEEAAAL

801 AKEVMEGVWP LAVPLEVEVG IGEDWLSAKG              829
```

The invention also provides a derivative polypeptide having SEQ ID NO:12 that is related to a *Thermus brockianus* polymerase polypeptide from strain 2AZN, wherein Asp is used in place of Gly at position 43.

```
  1 MLPLFEPKGR VLLVDGHHLA YRNFFALKGL TTSRGEPVQG    50
    VYDFAKSLLK

51 ALKEDGDVVI VVFDAKAPSF RHEAYGAYKA GRAPTPEDFP   100
    RQLALMKELV

101 DLLGLERLEV PGFEADDVLA ALAKKAEREG YEVRILTADR   150
    DLFQLLSDRI

151 AVLHPEGHLI TPGWLWERYG LRPEQWVDFR ALAGDPSDNI   200
    PGVKGIGEKT

201 ALKLLKEWGS LENIQKNLDQ VSPPSVREKI QAHLDDLRLS   250
    QELSRVRTDL

251 PLEVDFRRRR EPDREGLRAF LERLEFGSLL HEFGLLESPQ   300
    AAEEAPWPPP

301 EGAFLGFRLS RPEPMWAELL SLAASAKGRV YRAEAPHKAL   350
    SDLKEIRGLL

351 AKDLAVLALR EGLGLPPTDD PMLLAYLLDP SNTTPEGVAR   400
    RYGGEWTEEA
```

```
401 GERALLAERL YENLLSRLKG EEKLLWLYEE VEKPLSRVLA    450
    HMEATGVRLD
451 VPYLRALSLE VAAEMGRLEE EVFRLAGHPF NLNSRDQLER    500
    VLFDELGLPP
501 TGKTEKTGKR STSAAVLEAL REAHPIVEKI LQYRELAKLK    550
    GTYIDPLPAL
551 VHPRTGRLHT RFNQTATATG RLSSSDPNLQ NIPVRTPLGQ    600
    RIRRAFVAEE
601 GYLLVALDYS QTELRVLAHL SGDENLIRVF QEGRDIHTQT    650
    ASWMFGLPAE
651 AIDPLRRRAA KTTNFGVLYG MSAHRLSQEL GIPYEEAVAF    700
    IDRYFQSYPK
701 VKAWIERTLE EGRQRGYVET LFGRRRYVPD LNARVKSVRE    750
    AAERMAFNMP
751 VQGTAADLMK LAMVRLFPRL PEVGARMLLQ VHDELLLEAP    800
    KERAEEAAAL
801 AKEVMEGVWP LAVPLEVEVG IGEDWLSAKG               829
```

In another embodiment, the invention provides a derivative polypeptide having SEQ ID NO:13 that is related to the *Thermus brockianus* polymerase polypeptide from strain YS38, and that has Tyr in place of Phe at position 665. This derivative polypeptide has reduced bias against ddNTP incorporation. The sequence of SEQ ID NO:13 is below.

```
  1 MLPLFEPKGR VLLVDGHHLA YRNFFALKGL TTSRGEPVQG     30
    VYGFAKSLLK
 51 ALKEDGDVVI VVFDAKAPSF RHEAYGAYKA GRAPTPEDFP    100
    RQLALMKELV
101 DLLGLERLEV PGFEADDVLA ALAKKAEREG YEVRILTADR    150
    DLFQLLSDRI
151 AVLHPEGHLI TPGWLWERYG LRPEQWVDFR ALAGDPSDNI    200
    PGVKGIGEKT
201 ALKLLKEWGS LENIQKNLDQ VSPPSVREKI QAHLDDLRLS    250
    QELSRVRTDL
251 PLEVDFRRRR EPDREGLRAF LERLEFGSLL HEFGLLESPQ    300
    AAEEAPWPPP
301 EGAFLGFRLS RPEPMWAELL SLAASAKGRV YRAEAPHKAL    350
    SDLKEIRGLL
351 AKDLAVLALR EGLGLPPTDD PMLLAYLLDP SNTTPEGVAR    400
    RYGGEWTEEA
401 GERALLAERL YENLLSRLKG EEKLLWLYEE VEKPLSRVLA    450
    HMEATGVRLD
451 VPYLRALSLE VAAEMGRLEE EVFRLAGHPF NLNSRDQLER    500
    VLFDELGLPP
501 IGKTEKTGKR STSAAVLEAL REAHPIVEKI LQYRELAKLK    550
    GTYIDLLPAL
501 VHPRTGRLHT RFNQTATATG RLSSSDPNLQ NIPVRTPLGQ    600
    RIRRAFVAEE
601 GYLLVALDYS QIELRVLAHL SGDENLIRVF QEGRDIHTQT    650
    ASWMFGLPAE
651 AIDPLRRRAA KTINYGVLYG MSAHRLSQEL GIPYEEAVAF    700
    IDRYFQSYPK
701 VKAWIERTLE EGRQRGYVET LFGRRRYVPD LNARVKSVRE    750
    AAERMAFNMP
751 VQGTAADLMK LAMVRLFPRL PEVGARMLLQ VHDELLLEAP    800
    KERAEEAAAL
801 AKEVMEGVWP LAVPLEVEVG IGEDWLSAKG               829
```

In another embodiment, the invention provides a derivative polypeptide having SEQ ID NO:14 that is related to the *Thermus brockianus* polymerase polypeptide from strain 2AZN and that has Tyr in place of Phe at position 665. This derivative polypeptide has reduced bias against ddNTP incorporation. The sequence of SEQ ID NO:14 is below.

```
  1 MLPLFEPKGR VLLVDGHHLA YRNFEALKGL TTSRGEPVQG     50
    VYGFAKSLLK
 51 ALKEDGDVVI VVFDAKAPSF RHEAYGAYKA GRAPTPEDFP    100
    RQLALMKELV
101 DLLGLERLEV PGFEADDVLA ALAKKAEREG YEVRILTADR    150
    DLFQLLSDRI
151 AVLHPEGHLI TPGWLWERYG LRPEQWVDFR ALAGDPSDNI    200
    PGVKGIGEKT
201 ALKLLKEWGS LENIQKNLDQ VSPPSVREKI QAHLDDLRLS    250
    QELSRVRTDL
251 PLEVDFRRRR EPDREGLRAF LERLEFGSLL HEFGLLESPQ    300
    AAEEAPWPPP
301 EGAFLGFRLS RPEPMWAELL SLAASAKGRV YRAEAPHKAL    350
    SDLKEIRGLL
351 AKDLAVLALR EGLGLPPTDD PMLLAYLLDP SNTTPEGVAR    400
    RYGGEWTEEA
401 GERALLAERL YENLLSRLKG EEKLLWLYEE VEKPLSRVLA    450
    HMEATGVRLD
451 VPYLRALSLE VAAEMGRLEE EVFRLAGHPF NLNSRDQLER    500
    VLFDELGLPP
501 IGKTEKTGKR STSAAVLEAL REAHPIVEKI LQYRELAKLK    550
    GTYIDLPLAL
551 VHPRTGRLHT RFNQTATATG RLSSSDPNLQ NIPVRTPLGQ    600
    RIRRAFVAEE
601 GYLLVALDYS QIELRVLAHL SGDENLIRVF QEGRDIHTQT    650
    ASWMFGLPAE
651 AIDPLRRRAA KTINYGVLYG MSAHRLSQEL GIPYEEAVAF    700
    IDRYFQSYPK
701 VKAWIERTLE EGRQRGYVET LFGRRRYVPD LNARVKSVRE    750
    AAERMAFNMP
751 VQGTAADLMK LAMVRLFPRL PEVGARMLLQ VHDELLLEAP    800
    KERAEEAAAL
801 AKEVMEGVWP LAVPLEVEVG IGEDWLSAKG               829
```

In another embodiment, the invention provides a derivative polypeptide having SEQ ID NO:15, related to a *Thermus brockianus* polypeptide from strain YS38 with reduced 5'-3' exonuclease activity and reduced bias against ddNTP incorporation. SEQ ID NO:15 has Asp in place of Gly at position 43 and Tyr in place of Phe at position 665. The sequence of SEQ ID NO:15 is below.

```
  1 MLPLFEPKGR VLLVDGHHLA YRNFFALKGL TTSRGEPVQG     50
    VYDFAKSLLK
 51 ALKEDGDVVI VVFDAKAPSF RHEAYGAYKA GRAPTPEDFP    100
    RQLALMKELV
```

```
101 DLLGLERLEV PGFEADDVLA ALAKKAEREG YEVRILTADR    150
    DLFQLLSDRI

151 AVLHPEGHLI TPGWLWERYG LRPEQWVDFR ALAGDPSDNI    200
    PGVKGIGEKT

201 ALKLLLKEWGS LENIQKNLDQ VSPPSVREKI QAHLDDLRLS   250
    QELSRVRTDL

251 PLEVDFRRRR EPDREGLRAF LERLEFGSLL HEFGLLESPQ    300
    AAEEAPWPPP

301 EGAFLGFRLS RPEPMWAELL SLAASAKGRV YRAEAPHKAL    350
    SDLKEIRGLL

351 AKDLAVLALR EGLGLPPTDD PMLLAYLLDP SNTTPEGVAR    400
    RYGGEWTEEA

401 GERALLAERL YENLLSRLKG EEKLLWLYEE VEKPLSRVLA    450
    HMEATGVRLD

451 VPYLRALSLE VAAEMGRLEE EVFRLAGHPF NLNSRDQLER    500
    VLFDELGLPP

501 IGKTEKTGKR STSAAVLEAL REAHPIVEKI LQYRELAKLK    550
    GTYIDLLPAL

501 VHPRTGRLHT RFNQTATATG RLSSSDPNLQ NIPVRTPLGQ    600
    RIRRAFVAEE

601 GYLLVALDYS QIELRVLAHL SGDENLIRVF QEGRDIHTQT    650
    ASWMFGLPAE

651 AIDPLRRRAA KTIN Y GVLYG MSAHRLSQEL GIPYEEAVAF  700
    IDRYFQSYPK

701 VKAWIERTLE EGRQRGYVET LFGRRRYVPD LNARVKSVRE    750
    AAERMAFNMP

751 VQGTAADLMK LAMVRLFPRL PEVGARMLLQ VHDELLLEAP    800
    KERAEEAAAL

801 AKEVMEGVWP LAVPLEVEVG IGEDWLSAKG               829
```

In another embodiment, the invention provides a derivative polypeptide having SEQ ID NO:16, related to a *Thermus brockianus* polypeptide from strain 2AZN with reduced 5'-3' exonuclease activity and reduced bias against ddNTP incorporation. SEQ ID NO:16 has Asp in place of Gly at position 43 and Tyr in place of Phe at position 665. The sequence of SEQ ID NO:16 is below.

```
  1 MLPLFEPKGR VLLVDGHHLA YRNFFALKGL TTSRGEPVQG     50
    VY D FAKSLLK

51 ALKEDGDVVI VVFDAKAPSF RHEAYGAYKA GRAPTPEDFP    100
    RQLALMKELV

101 DLLGLERLEV PGFEADDVLA ALAKKAEREG YEVRILTADR    150
    DLFQLLSDRI

151 AVLHPEGHLI TPGWLWERYG LRPEQWVDFR ALAGDPSDNI    200
    PGVKGIGEKT

201 ALKLLLKEWGS LENIQKNLDQ VSPPSVREKI QAHLDDLRLS   250
    QELSRVRTDL

251 PLEVDFRRRR EPDREGLRAF LERLEFGSLL HEFGLLESPQ    300
    AAEEAPWPPP

301 EGAFLGFRLS RPEPMWAELL SLAASAKGRV YRAEAPHKAL    350
    SDLKEIRGLL

351 AKDLAVLALR EGLGLPPTDD PMLLAYLLDP SNTTPEGVAR    400
    RYGGEWTEEA

401 GERALLAERL YENLLSRLKG EEKLLWLYEE VEKPLSRVLA    450
    HMEATGVRLD

451 VPYLRALSLE VAAEMGRLEE EVFRLAGHPF NLNSRDQLER    500
    VLFDELGLPP

501 IGKTEKTGKR STSAAVLEAL REAHPIVEKI LQYRELAKLK    550
    GTYIDPLPAL

551 VHPRTGRLHT RFNQTATATG RLSSSDPNLQ NIPVRTPLGQ    600
    RIRRAFVAEE

601 GYLLVALDYS QIELRVLAHL SGDENLIRVF QEGRDIHTQT    650
    ASWMFGLPAE

651 AIDPLRRRAA KTIN Y GVLYG MSAHRLSQEL GIPYEEAVAF  700
    IDRYFQSYPK

701 VKAWIERTLE EGRQRGYVET LFGRRRYVPD LNARVKSVRE    750
    AAERMAFNMP

751 VQGTAADLMK LAMVRLFPRL PEVGARMLLQ VHDELLLEAP    800
    KERAEEAAAL

801 AKEVMEGVWP LAVPLEVEVG IGEDWLSAKG               829
```

The DNA polymerase polypeptides of the invention have homology to portions of the amino acid sequences of the thermostable DNA polymerases of *Thermus aquaticus* and *Thermus thermophilus* (see FIG. 1). However, significant portions of the amino acid sequences of the present invention are distinct, including SEQ ID NO:17-50.

As indicated above, derivative and variant polypeptides of the invention are derived from the wild type *Thermus brockianus* polymerases by deletion or addition of one or more amino acids to the N-terminal and/or C-terminal end of the wild type polypeptide; deletion or addition of one or more amino acids at one or more sites within the wild type polypeptide; or substitution of one or more amino acids at one or more sites within the wild type polypeptide. Thus, the polypeptides of the invention may be altered in various ways including amino acid substitutions, deletions, truncations, and insertions.

Such variant and derivative polypeptides may result, for example, from genetic polymorphism or from human manipulation. Methods for such manipulations are generally known in the art. For example, amino acid sequence variants of the polypeptides can be prepared by mutations in the DNA. Methods for mutagenesis and nucleotide sequence alterations are well known in the art. See, for example, Kunkel, Proc. Natl. Acad. Sci. USA, 82, 488 (1985); Kunkel et al., Methods in Enzymol., 154, 367 (1987); U.S. Pat. No. 4,873,192; Walker and Gaastra, eds., Techniques in Molecular Biology, MacMillan Publishing Company, New York (1983) and the references cited therein. Guidance as to appropriate amino acid substitutions that do not affect biological activity of the protein of interest may be found in the model of Dayhoff et al., Atlas of Protein Sequence and Structure, Natl. Biomed. Res. Found., Washington, C. D. (1978), herein incorporated by reference.

The derivatives and variants of the isolated polypeptides of the invention have identity with at least about 92% of the amino acid positions of SEQ ID NO:5, SEQ ID NO:6, SEQ ID NO:7, or SEQ ID NO:8 and have DNA polymerase I activity and/or are thermally stable. In a preferred embodiment, polypeptide derivatives and variants have identity with at least about 95% of the amino acid positions of SEQ ID NO:5, SEQ ID NO:6, SEQ ID NO:7, or SEQ ID NO:8 and have DNA polymerase I activity and/or are thermally stable.

Amino acid residues of the isolated polypeptides and polypeptide derivatives and variants can be genetically encoded L-amino acids, naturally occurring non-genetically encoded L-amino acids, synthetic L-amino acids or D-enantiomers of any of the above. The amino acid notations used herein for the twenty genetically encoded L-amino acids and common non-encoded amino acids are conventional and are as shown in Table 2.

TABLE 2

| Amino Acid | One-Letter Symbol | Common Abbreviation |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |
| β-Alanine | | bAla |
| 2,3-Diaminopropionic acid | | Dpr |
| α-Aminoisobutyric acid | | Aib |
| N-Methylglycine (sarcosine) | | MeGly |
| Ornithine | | Orn |
| Citrulline | | Cit |
| t-Butylalanine | | t-BuA |
| t-Butylglycine | | t-BuG |
| N-methylisoleucine | | MeIle |
| Phenylglycine | | Phg |
| Cyclohexylalanine | | Cha |
| Norleucine | | Nle |
| Naphthylalanine | | Nal |
| Pyridylalanine | | |
| 3-Benzothienyl alanine | | |
| 4-Chlorophenylalanine | | Phe(4-Cl) |
| 2-Fluorophenylalanine | | Phe(2-F) |
| 3-Fluorophenylalanine | | Phe(3-F) |
| 4-Fluorophenylalanine | | Phe(4-F) |
| Penicillamine | | Pen |
| 1,2,3,4-Tetrahydro-isoquinoline-3-carboxylic acid | | Tic |
| β-2-thienylalanine | | Thi |
| Methionine sulfoxide | | MSO |
| Homoarginine | | hArg |
| N-acetyl lysine | | AcLys |
| 2,4-Diamino butyric acid | | Dbu |
| p-Aminophenylalanine | | Phe(pNH$_2$) |
| N-methylvaline | | MeVal |
| Homocysteine | | hCys |
| Homoserine | | hSer |
| ε-Amino hexanoic acid | | Aha |
| δ-Amino valeric acid | | Ava |
| 2,3-Diaminobutyric acid | | Dab |

Polypeptide variants that are encompassed within the scope of the invention can have one or more amino acids substituted with an amino acid of similar chemical and/or physical properties, so long as these variant polypeptides retain nucleic acid polymerase or DNA polymerase activity and/or remain thermally stable. Derivative polypeptides can have one or more amino acids substituted with an amino acids having different chemical and/or physical properties, so long as these variant polypeptides retain nucleic acid polymerase or DNA polymerase activity and/or remain thermally stable. Amino acids that are substitutable for each other in the present variant polypeptides generally reside within similar classes or subclasses. As known to one of skill in the art, amino acids can be placed into three main classes: hydrophilic amino acids, hydrophobic amino acids and cysteine-like amino acids, depending primarily on the characteristics of the amino acid side chain. These main classes may be further divided into subclasses. Hydrophilic amino acids include amino acids having acidic, basic or polar side chains and hydrophobic amino acids include amino acids having aromatic or apolar side chains. Apolar amino acids may be further subdivided to include, among others, aliphatic amino acids. The definitions of the classes of amino acids as used herein are as follows:

"Hydrophobic Amino Acid" refers to an amino acid having a side chain that is uncharged at physiological pH and that is repelled by aqueous solution. Examples of genetically encoded hydrophobic amino acids include Ile, Leu and Val. Examples of non-genetically encoded hydrophobic amino acids include t-BuA.

"Aromatic Amino Acid" refers to a hydrophobic amino acid having a side chain containing at least one ring having a conjugated π-electron system (aromatic group). The aromatic group may be further substituted with substituent groups such as alkyl, alkenyl, alkynyl, hydroxyl, sulfonyl, nitro and amino groups, as well as others. Examples of genetically encoded aromatic amino acids include phenylalanine, tyrosine and tryptophan. Commonly encountered non-genetically encoded aromatic amino acids include phenylglycine, 2-naphthylalanine, β-2-thienylalanine, 1,2,3,4-tetrahydroisoquinoline-3-carboxylic acid, 4-chlorophenylalanine, 2-fluorophenylalanine, 3-fluorophenylalanine and 4-fluorophenylalanine.

"Apolar Amino Acid" refers to a hydrophobic amino acid having a side chain that is generally uncharged at physiological pH and that is not polar. Examples of genetically encoded apolar amino acids include glycine, proline and methionine. Examples of non-encoded apolar amino acids include Cha.

"Aliphatic Amino Acid" refers to an apolar amino acid having a saturated or unsaturated straight chain, branched or cyclic hydrocarbon side chain. Examples of genetically encoded aliphatic amino acids include Ala, Leu, Val and Ile. Examples of non-encoded aliphatic amino acids include Nle.

"Hydrophilic Amino Acid" refers to an amino acid having a side chain that is attracted by aqueous solution. Examples of genetically encoded hydrophilic amino acids include Ser and Lys. Examples of non-encoded hydrophilic amino acids include Cit and hCys.

"Acidic Amino Acid" refers to a hydrophilic amino acid having a side chain pK value of less than 7. Acidic amino acids typically have negatively charged side chains at physiological pH due to loss of a hydrogen ion. Examples of genetically encoded acidic amino acids include aspartic acid (aspartate) and glutamic acid (glutamate).

"Basic Amino Acid" refers to a hydrophilic amino acid having a side chain pK value of greater than 7. Basic amino acids typically have positively charged side chains at physiological pH due to association with hydronium ion. Examples of genetically encoded basic amino acids include arginine, lysine and histidine. Examples of non-genetically encoded basic amino acids include the non-cyclic amino acids ornithine, 2,3-diaminopropionic acid, 2,4-diaminobutyric acid and homoarginine.

"Polar Amino Acid" refers to a hydrophilic amino acid having a side chain that is uncharged at physiological pH, but which has a bond in which the pair of electrons shared in common by two atoms is held more closely by one of the atoms. Examples of genetically encoded polar amino acids include asparagine and glutamine. Examples of non-genetically encoded polar amino acids include citrulline, N-acetyl lysine and methionine sulfoxide.

"Cysteine-Like Amino Acid" refers to an amino acid having a side chain capable of forming a covalent linkage with a side chain of another amino acid residue, such as a disulfide linkage. Typically, cysteine-like amino acids generally have a side chain containing at least one thiol (SH) group. Examples of genetically encoded cysteine-like amino acids include cysteine. Examples of non-genetically encoded cysteine-like amino acids include homocysteine and penicillamine.

As will be appreciated by those having skill in the art, the above classification are not absolute. Several amino acids exhibit more than one characteristic property, and can therefore be included in more than one category. For example, tyrosine has both an aromatic ring and a polar hydroxyl group. Thus, tyrosine has dual properties and can be included in both the aromatic and polar categories. Similarly, in addition to being able to form disulfide linkages, cysteine also has apolar character. Thus, while not strictly classified as a hydrophobic or apolar amino acid, in many instances cysteine can be used to confer hydrophobicity to a polypeptide.

Certain commonly encountered amino acids that are not genetically encoded and that can be present, or substituted for an amino acid, in the variant polypeptides of the invention include, but are not limited to, β-alanine (b-Ala) and other omega-amino acids such as 3-aminopropionic acid (Dap), 2,3-diaminopropionic acid (Dpr), 4-aminobutyric acid and so forth; α-aminoisobutyric acid (Aib); ε-aminohexanoic acid (Aha); δ-aminovaleric acid (Ava); N-methylglycine (MeGly); ornithine (Orn); citrulline (Cit); t-butylalanine (t-BuA); t-butylglycine (t-BuG); N-methylisoleucine (MeIle); phenylglycine (Phg); cyclohexylalanine (Cha); norleucine (Nle); 2-naphthylalanine (2-Nal); 4-chlorophenylalanine (Phe(4-Cl)); 2-fluorophenylalanine (Phe(2-F)); 3-fluorophenylalanine (Phe(3-F)); 4-fluorophenylalanine (Phe(4-F)); penicillamine (Pen); 1,2,3,4-tetrahydroisoquinoline-3-carboxylic acid (Tic); .beta.-2-thienylalanine (Thi); methionine sulfoxide (MSO); homoarginine (hArg); N-acetyl lysine (AcLys); 2,3-diaminobutyric acid (Dab); 2,3-diaminobutyric acid (Dbu); p-aminophenylalanine (Phe (pNH$_2$)); N-methyl valine (MeVal); homocysteine (hCys) and homoserine (hSer). These amino acids also fall into the categories defined above.

The classifications of the above-described genetically encoded and non-encoded amino acids are summarized in Table 3, below. It is to be understood that Table 3 is for illustrative purposes only and does not purport to be an exhaustive list of amino acid residues that may comprise the variant and derivative polypeptides described herein. Other amino acid residues that are useful for making the variant and derivative polypeptides described herein can be found, e.g., in Fasman, 1989, CRC Practical Handbook of Biochemistry and Molecular Biology, CRC Press, Inc., and the references cited therein. Amino acids not specifically mentioned herein can be conveniently classified into the above-described categories on the basis of known behavior and/or their characteristic chemical and/or physical properties as compared with amino acids specifically identified.

TABLE 3

| Classification | Genetically Encoded | Genetically Non-Encoded |
| --- | --- | --- |
| Hydrophobic | F, L, I, V | |
| Aromatic | F, Y, W | Phg, Nal, Thi, Tic, Phe(4-Cl), Phe(2-F), Phe(3-F), Phe(4-F), Pyridyl Ala, Benzothienyl Ala |

TABLE 3-continued

| Classification | Genetically Encoded | Genetically Non-Encoded |
| --- | --- | --- |
| Apolar | M, G, P | |
| Aliphatic | A, V, L, I | t-BuA, t-BuG, MeIle, Nle, MeVal, Cha, bAla, MeGly, Aib |
| Hydrophilic | S, K | Cit, hCys |
| Acidic | D, E | |
| Basic | H, K, R | Dpr, Orn, hArg, Phe(p-NH$_2$), DBU, A$_2$ BU |
| Polar | Q, N, S, T, Y | Cit, AcLys, MSO, hSer |
| Cysteine-Like | C | Pen, hCys, β-methyl Cys |

Polypeptides of the invention can have any amino acid substituted by any similarly classified amino acid to create a variant peptide, so long as the peptide variant is thermally stable and/or retains nucleic acid polymerase or DNA polymerase activity.

"Domain shuffling" or construction of "thermostable chimeric DNA polymerases" may be used to provide thermostable DNA polymerases containing novel properties. For example, placement of codons 289-422 from the *Thermus brockianus* polymerase coding sequence after codons 1-288 of the *Thermus aquaticus* DNA polymerase would yield a novel thermostable polymerase containing the 5'-3' exonuclease domain of *Thermus aquaticus* DNA polymerase (1-288), the 3'-5' exonuclease domain of *Thermus brockianus* polymerase (289-422), and the DNA polymerase domain of *Thermus aquaticus* DNA polymerase (423-832). Alternatively, the 5'-3' exonuclease domain and the 3'-5' exonuclease domain of *Thermus brockianus* polymerase may be fused to the DNA polymerase (dNTP binding and primer/template binding domains) portions of *Thermus aquaticus* DNA polymerase (about codons 423-832). The donors and recipients need not be limited to *Thermus aquaticus* and *Thermus brockianus* polymerases. *Thermus thermophilus* DNA polymerase 3'-5' exonuclease, 5'-3' exonuclease and DNA polymerase domains can similarly be exchanged for those in the *Thermus brockianus* polymerases of the invention.

For example, it has been demonstrated that the exonuclease domain of *Thermus aquaticus* Polymerase I can be removed from the amino terminus of the protein with out a significant loss of thermostability or polymerase activity (Erlich et al., (1991) Science 252: 1643-1651, Barnes, W. M., (1992) Gene 112:29-35., Lawyer et al., (1989) JBC 264:6427-6437). Other N-terminal deletions similarly have been shown to maintain thermostability and activity (Vainshtein et al., (1996) Protein Science 5:1785-1792 and references therein.) Therefore this invention also includes similarly truncated forms of any of the wild type or variant polymerases provided herein. For example, the invention is also directed to an active truncated variant of any of the polymerases provided by the invention in which the first 330 amino acids are removed. Moreover, the invention provides SEQ ID NO:56, a truncated form of a polymerase in which the N-terminal 289 amino acids have been removed from the wild type *Thermus brockianus* polymerase from strain YS38.

```
290                                                        Q   300
    AAEEAPWPPP

301 EGAFLGFRLS RPEPMWAELL SLAASAKGRV YRAEAPHKAL       350
    SDLKEIRGLL

351 AKDLAVLALR EGLGLPPTDD PMLLAYLLDP SNTTPEGVAR       400
    RYGGEWTEEA
```

-continued

```
401 GERALLAERL YENLLSRLKG EEKLLWLYEE VEKPLSRVLA  450
    HMEATGVRLD

451 VPYLRALSLE VAAEMGRLEE EVFRLAGHPF NLNSRDQLER  500
    VLFDELGLPP

501 IGKTEKTGKR STSAAVLEAL REARPIVEKI LQYRELAKLK  550
    GTYIDLLPAL

551 VHPRTGRLHT RFNQTATATG RLSSSDPNLQ NIPVRTPLGQ  600
    RIRRAFVAEE

601 GYLLVALDYS QIELRVLAHL SGDENLIRVF QEGRDIHTQT  650
    ASWMFGLPAE

651 AIDPLRRRAA KTINFGVLYG MSAHRLSQEL GIPYEEAVAF  700
    IDRYFQSYPK

701 VKAWIERTLE EGRQRGYVET LFGRRRYVPD LNARVKSVRE  750
    AAERMAFNMP

751 VQGTAADLMK LAMVRLFPRL PEVGARMLLQ VHDELLLEAP  800
    KERAEEAAAL

801 AKEVMEGVWP LAVPLEVEVG IGEDWLSAKG              829
```

In another embodiment, the invention provides SEQ ID NO:57, a truncated form of a polymerase in which the N-terminal 289 amino acids have been removed from the *Thermus brockianus* polymerase from strain 2AZN.

```
290                                       Q    300
    AAEEAPWPPP

301 EGAFLGFRLS RPEPMWAELL SLAASAKGRV YRAEAPHKAL  350
    SDLKEIRGLL

351 AKDLAVLALR EGLGLPPTDD PMLLAYLLDP SNTTPEGVAR  400
    RYGGEWTEEA

401 GERALLAERL YENLLSRLKG EEKLLWLYEE VEKPLSRVLA  450
    HMEATGVRLD

451 VPYLRALSLE VAAEMGRLEE EVFRLAGHPF NLNSRDQLER  500
    VLFDELGLPP

501 IGKTEKTGKR STSAAVLEAL REAHPIVEKI LQYRELAKLK  550
    GTYID P LPAL

551 VHPRTGRLHT RFNQTATATG RLSSSDPNLQ NIPVRTPLGQ  600
    RIRRAFVAEE

601 GYLLVALDYS QIELRVLAHL SGDENLIRVF QEGRDIHTQT  650
    ASWMFGLPAE

651 AIDPLRRRAA KTINFGVLYG MSAHRLSQEL GIPYEEAVAF  700
    IDRYFQSYPK

701 VKAWIERTLE EGRQRGYVET LFGRRRYVPD LNARVKSVRE  750
    AAERMAFNMP

751 VQGTAADLMK LAMVRLFPRL PEVGARMLLQ VHDELLLEAP  800
    KERAEEAAAL

801 AKEVMEGVWP LAVPLEVEVG IGEDWLSAKG              829
```

Thus, the polypeptides of the invention encompass both naturally occurring proteins as well as variations, truncations and modified forms thereof. Such variants will continue to possess the desired activity. The deletions, insertions, and substitutions of the polypeptide sequence encompassed herein are not expected to produce radical changes in the characteristics of the polypeptide. One skilled in the art can readily evaluate the thermal stability, nucleic acid polymerase or DNA polymerase activity of the polypeptides and variant polypeptides of the invention by routine screening assays.

Kits and compositions containing the present polypeptides are substantially free of cellular material. Such preparations and compositions have less than about 30%, 20%, 10%, 5%, (by dry weight) of contaminating bacterial cellular protein.

The activity of polymerase polypeptides and variant polypeptides can be assessed by any procedure known to one of skill in the art. For example, the DNA synthetic activity of the variant and non-variant polymerase polypeptides of the invention can be tested in standard DNA sequencing or DNA primer extension reaction. One such assay can be performed in a 100 μl (final volume) reaction mixture, containing, for example, 0.1 mM dCTP, dTTP, dGTP, α-$^{32}$P-dATP, 0.3 mg/ml activated calf thymus DNA and 0.5 mg/ml BSA in a buffer containing: 50 mM KCl, 1 mM DTT, 10 mM MgCl$_2$ and 50 mM of a buffering compound such as PIPES, Tris or Triethylamine. A dilution to 0.1 units/μl of each polymerase enzyme is prepared, and 5 μl of such a dilution is added to the reaction mixture, followed by incubation at 60° C. for 10 minutes. Reaction products can be detected by determining the amount of $^{32}$P incorporated into DNA or by observing the products after separation on a polyacrylamide gel.

Uses for Nucleic Acid Polymerases

The thermostable enzyme of this invention may be used for any purpose in which DNA or RNA polymerase enzyme activity is necessary or desired. For example, the present polymerases can be used in one or more of the following procedures: DNA sequencing, DNA amplification, RNA amplification, reverse transcription, DNA synthesis and/or primer extension. The polymerases of the invention can be used to amplify DNA by polymerase chain reaction (PCR). The polymerases of the invention can be used to sequence DNA by Sanger sequencing procedures. The polymerases of the invention can also be used in primer extension reactions. The polymerases of the invention can be used test for single nucleotide polymorphisms (SNPs) by single nucleotide primer extension using terminator nucleotides. Any such procedures and related procedures, for example, polynucleotide or primer labeling, minisequencing and the like are contemplated for use with the present polymerases.

Methods of the invention comprise the step of extending a primed polynucleotide template with at least one labeled nucleotide, wherein the extension is catalyzed by a polymerase of the invention. DNA polymerases used for Sanger sequencing can produce fluorescently labeled products that are analyzed on an automated fluorescence-based sequencing apparatus such as an Applied Biosystems 310 or 377 (Applied Biosystems, Foster City, Calif.). Detailed protocols for Sanger sequencing are known to those skilled in the art and may be found, for example in Sambrook et al, Molecular Cloning, A Laboratory Manual, Second Edition, Cold Spring Harbor Press, Cold Spring Harbor, N.Y. (1989).

In one embodiment, the polymerases of the invention are used for DNA amplification. Any DNA procedure that employs a DNA polymerase can be used, for example, in polymerase chain reaction (PCR) assays, strand displacement amplification and other amplification procedures. Strand displacement amplification can be used as described in Walker et al (1992) Nucl. Acids Res. 20, 1691-1696. The term "polymerase chain reaction" ("PCR") refers to the method of K. B. Mullis U.S. Pat. Nos. 4,683,195; 4,683,202; and 4,965,188, hereby incorporated by reference, which describe a method for increasing the concentration of a segment of a target sequence in a mixture of genomic or other DNA without cloning or purification.

The PCR process for amplifying a target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To do amplification, the mixture is denatured and the primers are annealed to complementary sequences within the target molecule. Following annealing, the primers are extended with a polymerase so as to form a new pair of complementary strands. The steps of denaturation, primer annealing and polymerase extension are termed a "cycle." There can be numerous cycles, and the amount of amplified DNA produced increases with each cycle. Hence, to obtain a high concentration of an amplified target nucleic acid, many cycles are performed.

The steps involve in PCR nucleic acid amplification method are described in more detail below. For ease of discussion, the nucleic acid to be amplified is described as being double-stranded. However, the process is equally useful for amplifying a single-stranded nucleic acid, such as an mRNA, although the ultimate product is generally double-stranded DNA. In the amplification of a single-stranded nucleic acid, the first step involves the synthesis of a complementary strand using, for example, one of the two amplification primers. The succeeding steps generally proceed as follows:

(a) Each nucleic acid strand is contacted with four different nucleoside triphosphates and one oligonucleotide primer for each nucleic acid strand to be amplified, wherein each primer is selected to be substantially complementary to a portion the nucleic acid strand to be amplified, such that the extension product synthesized from one primer, when it is separated from its complement, can serve as a template for synthesis of the extension product of the other primer. To promote the proper annealing of primer(s) and the nucleic acid strands to be amplified, a temperature that allows hybridization of each primer to a complementary nucleic acid strand is used.

(b) After primer annealing, a polymerase is used for primer extension that incorporates the nucleoside triphosphates into a growing nucleic acid strand that is complementary to the strand hybridized by the primer. In general, this primer extension reaction is performed at a temperature and for a time effective to promote the activity of the enzyme and to synthesize a "full length" complementary nucleic acid strand, that extends into a through a complete second primer binding. However, the temperature is not so high as to separate each extension product from its nucleic acid template strand.

(c) The mixture from step (b) is then heated for a time and at a temperature sufficient to separate the primer extension products from their complementary templates. The temperature chosen is not so high as to irreversibly denature the polymerase present in the mixture.

(d) The mixture from (c) is cooled for a time and at a temperature effective to promote hybridization of a primer to each of the single-stranded molecules produced in step (b).

(e) The mixture from step (d) is maintained at a temperature and for a time sufficient to promote primer extension by polymerase to produce a "full length" extension product. The temperature used is not so high as to separate each extension product from the complementary strand template. Steps (c)-(e) are repeated until the desired level of amplification is obtained.

The amplification method is useful not only for producing large amounts of a specific nucleic acid sequence of known sequence but also for producing nucleic acid sequences that are known to exist but are not completely specified. One need know only the identity of a sufficient number of bases at both ends of the sequence in sufficient detail so that two oligonucleotide primers can be prepared that will hybridize to different strands of the desired sequence at those positions. An extension product is synthesized from one primer. When that extension product is separated from the template the extension product can serve as a template for extension of the other primer. The greater the knowledge about the bases at both ends of the sequence, the greater can be the specificity of the primers for the target nucleic acid sequence.

Thermally stable DNA polymerases are therefore generally used for PCR because they can function at the high temperatures used for melting double stranded target DNA and annealing the primers during each cycle of the PCR reaction. High temperature results in thermodynamic conditions that favor primer hybridization with the target sequences and not hybridization with non-target sequences (H. A. Erlich (ed.), PCR Technology, Stockton Press [1989]).

The thermostable polymerases of the present invention satisfy the requirements for effective use in amplification reactions such as PCR. The present polymerases do not become irreversibly denatured (inactivated) when subjected to the required elevated temperatures for the time necessary to melt double-stranded nucleic acids during the amplification process. Irreversible denaturation for purposes herein refers to permanent and complete loss of enzymatic activity. The heating conditions necessary for nucleic acid denaturation will depend, e.g., on the buffer salt concentration and the composition and length of the nucleic acids being denatured, but typically range from about 90° C. to about 105° C. for a time depending mainly on the temperature and the nucleic acid length, typically from a few seconds up to four minutes. Higher temperatures may be required as the buffer salt concentration and/or GC composition of the nucleic acid is increased. The polymerases of the invention do not become irreversibly denatured for relatively short exposures to temperatures of about 90° C. to 100° C.

The thermostable polymerases of the invention have an optimum temperature at which they function that is higher than about 45° C. Temperatures below 45° C. facilitate hybridization of primer to template, but depending on salt composition and concentration and primer composition and length, hybridization of primer to template can occur at higher temperatures (e.g., 45° C. to 70° C.), which may promote specificity of the primer hybridization reaction. The DNA polymerase polypeptides of the invention exhibit activity over a broad temperature range from about 37° C. to about 90° C.

The present polymerases have particular utility for PCR not only because of their thermal stability but also because of their fidelity in replicating the target nucleic acid. With PCR, it is possible to amplify a single copy of a specific target nucleic acid to a level detectable by several different methodologies. However, if the sequence of the target nucleic acid is not replicated with fidelity, then the amplified product can comprise a pool of nucleic acids with diverse sequences. Hence, a polymerase that can accurately replicate the sequence of the target is highly desirable.

Any nucleic acid can act as a "target nucleic acid" for the PCR methods of the invention. The term "target," when used in reference to the polymerase chain reaction, refers to the region of nucleic acid bounded by the primers used for polymerase chain reaction. In addition to genomic DNA, any cDNA, oligonucleotide or polynucleotide can be amplified with the appropriate set of primer molecules. In particular, the amplified segments created by the PCR process itself are, themselves, efficient templates for subsequent PCR amplifications. The length of the amplified segment of the desired target sequence is determined by the relative positions of the primers with respect to each other, and therefore, this length is a controllable parameter.

The amplified target nucleic acid can be detected by any method known to one of skill in the art. For example, target nucleic acids are often amplified to such an extent that they form a band visible on a size separation gel. Target nucleic acids can also be detected by hybridization with a labeled probe; by incorporation of biotinylated primers during PCR followed by avidin-enzyme conjugate detection; by incorporation of $^{32}$P-labeled deoxynucleotide triphosphates during PCR, and the like.

The amount of amplification can also be monitored, for example, by use of a reporter-quencher oligonucleotide as described in U.S. Pat. No. 5,723,591, and a polymerase of the invention that has 5'-3' nuclease activity. The reporter-quencher oligonucleotide has an attached reporter molecule and an attached quencher molecule that is capable of quenching the fluorescence of the reporter molecule when the two are in proximity. Quenching occurs when the reporter-quencher oligonucleotide is not hybridized to a complementary nucleic acid because the reporter molecule and the quencher molecule tend to be in proximity or at an optimal distance for quenching. When hybridized, the reporter-quencher oligonucleotide emits more fluorescence than when unhybridized because the reporter molecule and the quencher molecule tend to be further apart. To monitor amplification, the reporter-quencher oligonucleotide is designed to hybridize 3' to an amplification primer. During amplification, the 5'-3' nuclease activity of the polymerase digests the reporter oligonucleotide probe, thereby separating the reporter molecule from the quencher molecule. As the amplification is conducted, the fluorescence of the reporter molecule increases. Accordingly, the amount of amplification performed can be quantified based on the increase of fluorescence observed.

Oligonucleotides used for PCR primers are usually about 9 to about 75 nucleotides, preferably about 17 to about 50 nucleotides in length. Preferably, an oligonucleotide for use in PCR reactions is about 40 or fewer nucleotides in length (e.g., 9, 12, 15, 18, 20, 21, 24, 27, 30, 35, 40, or any number between 9 and 40). Generally specific primers are at least about 14 nucleotides in length. For optimum specificity and cost effectiveness, primers of 16-24 nucleotides in length are generally preferred.

Those skilled in the art can readily design primers for use processes such as PCR. For example, potential primers for nucleic acid amplification can be used as probes to determine whether the primer is selective for a single target and what conditions permit hybridization of a primer to a target within a sample or complex mixture of nucleic acids.

The present invention also contemplates use of the present polymerase polypeptides in combination with other procedures or enzymes. For example, the polymerase polypeptides have reverse transcription activity and can be used for reverse transcription of an RNA. In this method, the RNA is converted to cDNA due to the reverse transcriptase activity of the polymerase, and then amplified using a polymerizing activity of one of the thermostable polymerases of the invention. Additional reverse transcriptase enzyme may be added as needed. Such procedures are provided in U.S. Pat. No. 5,322,770, incorporated by reference herein.

In another embodiment, polymerases of the invention with 5'-3' exonuclease activity are used to detect target nucleic acids in an invader-directed cleavage assay. This type of assay is described, for example, in U.S. Pat. No. 5,994,069. It is important to note that the 5'-3' exonuclease of polymerases is not really an exonuclease that progressively cleaves nucleotides from the 5' end of a nucleic acid, but rather a nuclease that can cleave certain types of nucleic acid structures to produce oligonucleotide cleavage products. Such cleavage is sometimes called structure-specific cleavage.

In general, the invader-directed cleavage assay employs at least one pair of oligonucleotides that interact with a target nucleic acid to form a cleavage structure for the 5'-3' nuclease activity of the polymerase. Distinctive cleavage products are released when the cleavage structure is cleaved by the 5'-3' nuclease activity of the DNA polymerase. Formation of such a target-dependent cleavage structure and the resulting cleavage products is indicative of the presence of specific target nucleic acid sequences in the test sample.

Therefore, in the invader-directed cleavage procedure, the 5'-3' nuclease activity of the present polymerases is needed as well at least one pair of oligonucleotides that interact with a target nucleic acid to form a cleavage structure for the 5'-3' nuclease. The first oligonucleotide, sometimes termed the "probe," can hybridize within the target site but downstream of a second oligonucleotide, sometimes termed an "invader" oligonucleotide. The invader oligonucleotide can hybridize adjacent and upstream of the probe oligonucleotide. However, the target sites to which the probe and invader oligonucleotides hybridize overlap such that the 3' segment of the invader oligonucleotide overlaps with the 5' segment of the probe oligonucleotide. The 5'-3' nuclease of the present polymerases can cleave the probe oligonucleotide at an internal site to produce distinctive fragments that are diagnostic of the presence of the target nucleic acid in a sample. Further details and methods for adapting the invader-directed cleavage assay to particular situations can be found in U.S. Pat. No. 5,994,069.

One or more nucleotide analogs can also be used with the present methods, kits and with the polymerases. Such nucleotide analogs can be modified or non-naturally occurring nucleotides such as 7-deaza purines (i.e., 7-deaza-dATP and 7-deaza-dGTP). Nucleotide analogs include base analogs and comprise modified forms of deoxyribonucleotides as well as ribonucleotides. As used herein the term "nucleotide analog" when used in reference to targets present in a PCR mixture refers to the use of nucleotides other than dATP, dGTP, dCTP and dTTP; thus, the use of dUTP (a naturally occurring dNTP) in a PCR would comprise the use of a nucleotide analog in the PCR. A PCR product generated using dUTP, 7-deaza-dATP, 7-deaza-dGTP or any other nucleotide analog in the reaction mixture is said to contain nucleotide analogs.

The invention also provides kits that contain at least one of the polymerases of the invention. Individual kits may be adapted for performing one or more of the following procedures: DNA sequencing, DNA amplification, RNA Amplification and/or primer extension. Kits of the invention comprise a DNA polymerase polypeptide of the invention and at least one nucleotide. A nucleotide provided in the kits of the invention can be labeled or unlabeled. Kits preferably can also contain instructions on how to perform the procedures for which the kits are adapted.

Optionally, the subject kit may further comprise at least one other reagent required for performing the method the kit is adapted to perform. Examples of such additional reagents include: another unlabeled nucleotide, another labeled nucleotide, a balance mixture of nucleotides, one or more chain terminating nucleotides, one or more nucleotide analogs, buffer solution(s), magnesium solution(s), cloning vectors, restriction endonucleases, sequencing primers, reverse transcriptase, and DNA or RNA amplification primers. The reagents included in the kits of the invention may be supplied in premeasured units so as to provide for greater precision and accuracy. Typically, kits reagents and other components are placed and contained in separate vessels. A reaction vessel, test tube, microwell tray, microtiter dish or other container can also be included in the kit. Different labels can be used on different reagents so that each reagent can be distinguished from another.

The following Examples further illustrate the invention and are not intended to limit the scope of the invention.

Example 1

Cloning of *Thermus brockianus* Nucleic Acid Polymerases

Bacteria Growth and Genomic DNA Isolation

The 2AZN strain of *Thermus brockianus* used in this invention was obtained from Dr. R. A. D. Williams, Queen Mary and Westfield College, London, England. Strain YS38 was obtained from the NCIMB collection. Both of these bacterial samples were obtained as lyophilized bacteria and were revived in 4 ml of ATCC Thermus bacteria growth media 461 (Castenholtz TYE medium). The 4 ml overnight cultures were grown at 65° C. in a water bath orbital shaker. The 4-ml cultures were transferred to 200 ml of TYE and grown overnight at 65° C. in a water bath orbital shaker to stationary phase. *Thermus brockianus* genomic DNAs were prepared using a Qiagen genomic DNA preparation kit (Qiagen, Valencia, Calif.).

Cloning of the *Thermus brockianus* Polymerase Genes

The forward and reverse primers were designed by analysis of 5' and 3' terminal homologous conserved regions of the Genebank DNA sequences of the DNA Pol I genes from *Thermus aquaticus* (Taq), *Thermus thermophilus* (Tth), *Thermus filiformis* (Tfi), *Thermus caldophilus*, and *Thermus flavus*. The *Thermus brockianus* polymerase gene from strain YS38 was first cloned as a partial fragment which was amplified using N-terminal primer 5'-ggc cac cac ctg gcc tac-3' (SEQ ID NO:58) and and C-terminal primer 5'-ccc acc tcc acc tcc ag-3' (SEQ ID NO:51). The PCR reaction mixture contained 2.5 ul of 10×cPfu Turbo reaction buffer (Stratagene), 50 ng genomic DNA template, 0.2 mM (each) dNTPs, 20 pmol of each primer, and 10 units of Pfu Turbo DNA polymerase (Stratagene) in a 25 µl total reaction volume. The reaction was started by adding a premix containing enzyme, $MgCl_2$, dNTPs, buffer and water to another premix containing primer and template preheated at 80° C. The entire reaction mixture was then denatured (30 s, 96° C.) followed by 30 PCR cycles (97° C. for 3 sec, 56° C. for 30 sec, 72° C. for 2 min 30 sec) with a finishing step (72° C. for 6 min). This produced an approximate 2.3 kb amplified DNA fragment. This amplified DNA fragment was purified from the PCR reaction mix using a Quiagen PCR cleanup kit (Quiagen). The fragment was then ligated into the inducible expression vector pCR®T7 CT-TOPO® ((Invitrogen, Carlsbad, Calif.).

The sequence of the full-length *Thermus brockianus* strain YS38 open reading frame and flanking regions was obtained by genomic DNA sequencing using primers designed to hybridize to portions of the *Thermus brockianus* strain YS38 Polymerase I gene. The C terminal end was sequenced using the forward primer 5'-cga cct caa cgc ccg ggt aaa ga-3' (SEQ ID NO:52). The N terminal end was sequenced using the reverse primer 5'-gct ttt ggc gaa gcc gta gac ccc t-3' (SEQ ID NO:53). The sequencing reactions were performed using a pre-denaturation step (95° C., 5 min) followed by 60 cycles (97° C. for 5 sec., 60° C. for 4 min). The reaction mixture consisted of 16 ul Big Dye VI Ready Reaction mix, 2.4 µg DNA, 15 pmol primer in a 40 µl reaction volume. The sequence of the 5' (start) and 3' (end) of the *Thermus brockianus* YS38 gene were thus obtained.

Using the sequence information obtained in the genomic DNA sequencing reactions above, two primers were designed to amplify the full-length *Thermus brockianus* YS38 polymerase gene: N-terminal primer 5'-cat atg ctt ccc ctc ttt gag ccc a-3' (SEQ ID NO:54) and C-terminal primer 5'-gtc gac tag ccc ttg gcg gaa agc-3' (SEQ ID NO:55). These primers introduced NdeI and Sal I restriction sites that facilitated subcloning. The PCR reaction mixture used to amplify *Thermus brockianus* strain YS38 contained 2.5 µl of 10× Amplitaq reaction buffer (Applied Biosystems), 2 mM $MgCl_2$, 120 ng genomic DNA template, 0.2 mM (each) dNTPs, 20 pmol of each primer, and 1.25 units of Amplitaq in a 25 µl total reaction volume. The reaction was started by adding a premix containing enzyme, $MgCl_2$, dNTPs, buffer and water to another premix containing primer and template preheated at 80° C. The entire reaction mixture was then denatured (30 sec at 96° C.) followed by 30 PCR cycles (97° C. for 3 sec, 62° C. for 30 sec, 72° C. for 3 min) with a finishing step (72° C. for 7 min).

The same primers used to amplify the polymerase gene from *Thermus brockianus* strain YS38 were used to amplify the polymerase gene from *Thermus brockianus* strain 2AZN. The 2AZN PCR reaction contained 5 µl of 10× cPfu Turbo reaction buffer (Stratagene), 200 ng genomic DNA template, 0.2 mM (each) dNTPs, 20 pmol of each primer, and 2.5 units of Pfu Turbo DNA polymerase (Stratagene) in a 50 µl total reaction volume. The reaction was started by adding a premix containing enzyme, dNTPs, buffer and water to another premix containing primer and template preheated at 80° C. The entire reaction mixture was then denatured (2 min, 96° C.) followed by PCR cycling for 25 cycles (96° C. for 5 sec, 64° C. for 30 sec, 72° C. for 3 min) with a finishing step (72° C. for 5 min).

Both PCR reactions produced approximate 2.5 kb amplified DNA fragments. The amplified DNA fragments were purified from the PCR reaction mix using a Qiagen PCR cleanup kit (Qiagen Inc., Valencia, Calif.). The *Thermus brockianus* strain YS38 fragment was ligated into the inducible expression vector pCR®T7 CT-TOPO® (Invitrogen, Carlsbad, Calif.). The *Thermus brockianus* strain 2AZN fragment was then ligated into the vector pCR4®TOPO®TA (Invitrogen, Carlsbad, Calif.). Three different clones were sequenced in order to rule out PCR errors. The sequence of the *Thermus brockianus* 2AZN polymerase gene is provided as SEQ ID NO:2. The consensus sequence of *Thermus brockianus* strain YS39 is provided as SEQ ID NO:1. The two sequences are compared in an alignment provided in FIG. 1. The sequences of both polymerase genes were reconfirmed by sequencing PCR fragments produced by reamplifying both full-length genes from the their respective genomic DNAs.

Figure 2B:
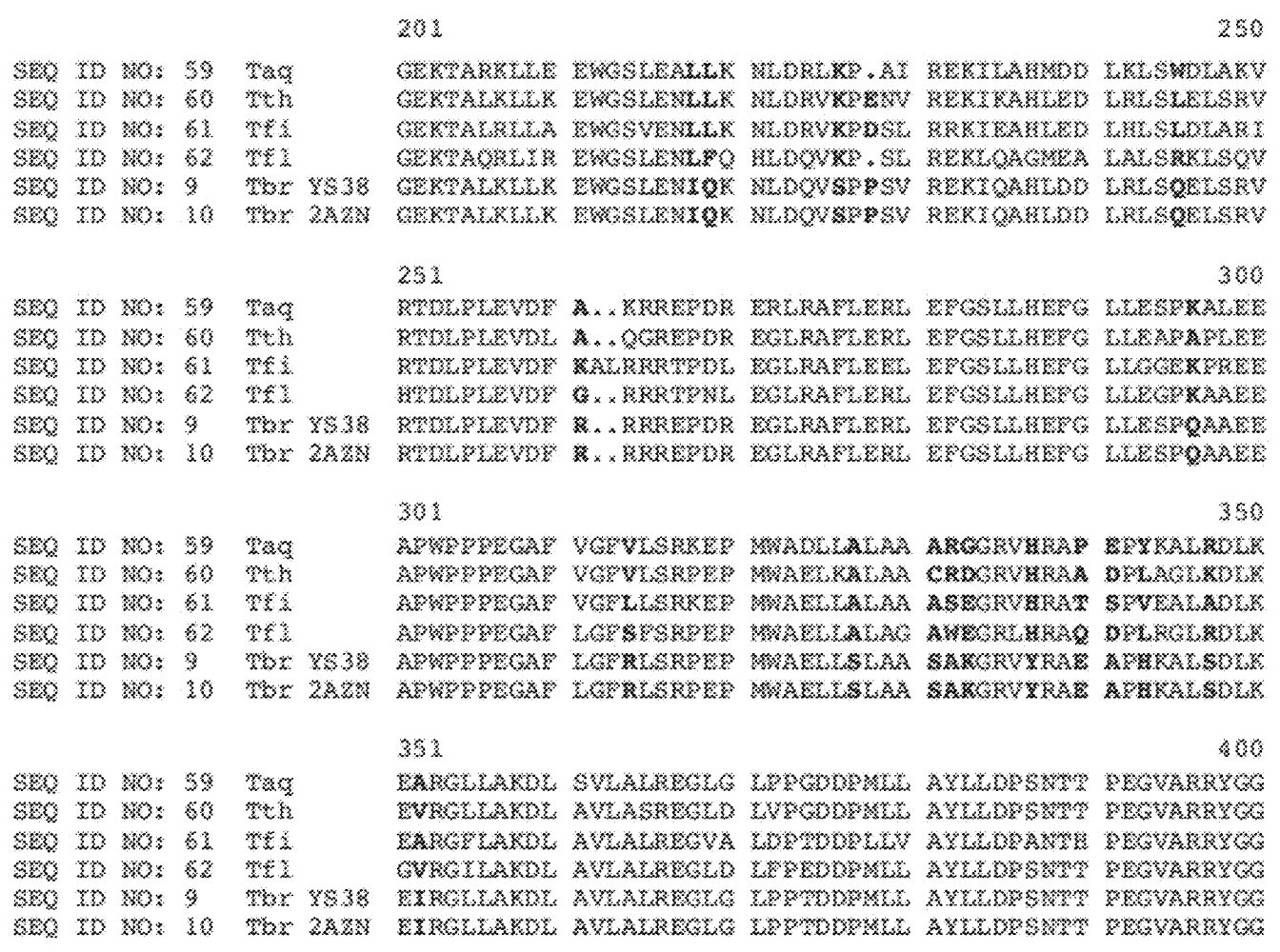

The deduced amino acid sequences of *Thermus brockianus* YS38 and *Thermus brockianus* 2AZN were aligned with the polymerase enzymes from *Thermus aquaticus* (Taq) *Thermus thermophilus* (Tth), *Thermus filiformis* (Tfi) and *Thermus flavus* using the program Vector NTI (Informax, Inc.). The alignment is shown in FIG. 2. There are 44 amino acid positions where *Thermus brockianus* YS38 and/or *Thermus brockianus* 2AZN are different from the published sequences of other known Thermus polymerases. For example, the *Thermus brockianus* polymerases have a different start site from the others, which accounts for the different amino acid numbering.

Modification of *Thermus brockianus* Polymerase Coding Regions

To produce *Thermus brockianus* polymerase from strains YS39 and 2AZN in a form better suited for dye-terminator DNA sequencing, two amino acid substitutions were separately made in the nucleic acid coding these polymerases. These are the FS (Tabor and Richardson, 1995 PNAS 92: 6339-6343; U.S. Pat. No. 5,614,365) and exo-minus mutations (see U.S. Pat. No. 5,466,591; Xu Y., Derbyshire V., Ng K., Sun X-C., Grindley N. D., Joyce C. M. (1997) J. Mol. Biol. 268, 284-302). To reduce the exonuclease activity to very low levels, the mutation G43D was introduced. To reduce the discrimination between ddNTP's and dNTP's, the mutation F665Y was introduced.

Mutagenesis of the *Thermus brockianus* polymerase genes was carried out using the modified QuickChange™ (Stratagene) PCR mutagenesis protocol described in Sawano & Miyawaki (2000). The mutagenized gene was resequenced completely to confirm the introduction of the mutations and to ensure that no PCR errors were introduced.

Example 2

Protein Expression and Purification

Nucleic acids encoding both *Thermus brockianus* open reading frames were separately subcloned into the expression vector pET24a (Novagen, Madison, Wis.) using the Nde I and Sal I restriction sites. These plasmids were then used to transform BL21 *E. coli* cells. The cells were grown in one liter of Terrific Broth (Maniatis) to an optical density of 1.2 OD and the protein was overproduced by four-hour induction with 1.0 mM IPTG. The cells were harvested by centrifugation, washed in 50 mM Tris (pH 7.5), 5 mM EDTA, 5% glycerol, 10 mM EDTA to remove growth media, and the cell pellet frozen at –80° C.

To isolate *Thermus brockianus* polymerase enzymes, the cells were thawed and resuspended in 2.5 volumes (wet weight) of 50 mM Tris (pH 7.2), 400 mM NaCl, 1 mM EDTA. The cell walls were disrupted by sonication. The resulting *E. coli* cell debris was removed by centrifugation. The cleared lysate was pasteurized in a water bath (75° C., 45 min), denaturing and precipitating the majority of the non-thermostable *E. coli* proteins and leaving the thermostable *Thermus brockianus* polymerase in solution. *E. coli* genomic DNA was removed by coprecipitation with 0.3% Polyethyleneimine (PEI). The cleared lysate was then applied to two columns in series: (1) a Biorex 70 cation exchange resin (BioRad, Hercules, Calif.) which chelates excess PEI and (2) a heparin-agarose resin (Sigma, St. Louis, Mo.) which retains the polymerase. The Heparin-agarose column was washed with 5 column volumes of 20 mM Tris (pH 8.5), 5% glycerol, 100 mM NaCl, 0.1 mM EDTA, 0.05% Triton X-100 and 0.05% Tween-20 (KTA buffer). The protein was then eluted with a 0.1 to 1.0M NaCl linear gradient. The polymerase eluted at 0.8M NaCl. The eluted *Thermus brockianus* polymerase enzymes were concentrated and the buffer exchanged using a Millipore concentration filter (30 kD M. wt. cutoff). The concentrated protein was stored at in KTA buffer (no salt) plus 50% glycerol at –20° C. The activity of the polymerases was measured using a nicked salmon sperm DNA radiometric activity assay.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant arts are intended to be within the scope of the following claims.

What is claimed is:

1. An isolated nucleic acid polymerase comprising SEQ ID NO:9.

2. An isolated nucleic acid polymerase comprising SEQ ID NO:9 having a G43D mutation that decreases 5'-3' exonuclease activity relative to the SEQ ID NO:9 nucleic acid polymerase without the G43D mutation.

3. An isolated nucleic acid polymerase comprising SEQ ID NO:9 having a F665Y mutation that reduces discrimination against dideoxynucleotide triphosphates relative to a the SEQ ID NO:9 nucleic acid polymerase without the F665Y mutation.

4. A kit comprising a container containing a nucleic acid polymerase, wherein the nucleic acid polymerase comprises SEQ ID NO:9.

5. The kit of claim 4 further comprising a container containing an unlabeled nucleotide, a labeled nucleotide, a balanced mixture of nucleotides, a chain terminating nucleotide, a nucleotide analog, a buffer solution, a solution containing magnesium, a cloning vector, a restriction endonuclease, a sequencing primer, a solution containing reverse transcriptase, or a DNA or RNA amplification primer.

6. The kit of claim 4, adapted for performing DNA sequencing, DNA amplification, reverse transcription, RNA amplification or primer extension.

* * * * *

UNITED STATES PATENT AND TRADEMARK OFFICE
CERTIFICATE OF CORRECTION

| | | |
|---|---|---|
| PATENT NO. | : 8,318,469 B2 | Page 1 of 1 |
| APPLICATION NO. | : 11/300194 | |
| DATED | : November 27, 2012 | |
| INVENTOR(S) | : Rozzelle et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1394 days.

Signed and Sealed this
Twenty-first Day of October, 2014

Michelle K. Lee
*Deputy Director of the United States Patent and Trademark Office*

SEQUENCE LISTING

<160> NUMBER OF SEQ ID NOS: 62

<210> SEQ ID NO 1
<211> LENGTH: 2493
<212> TYPE: DNA
<213> ORGANISM: Thermus brockianus

<400> SEQUENCE: 1

```
atgcttcccc tctttgagcc caagggccgg gtgctcctgg tggacggcca ccacctggcc      60
taccgtaact tcttcgccct caagggctc accacgagcc ggggcgagcc cgtgcaaggg     120
gtctacggct tcgccaaaag cctcctcaag gccctgaagg aggacgggga cgtggtcatc     180
gtggtctttg acgccaaggc cccctctttt cgccacgagg cctacggggc ctacaaggcg     240
ggccgggccc ctacccggga ggactttccg aggcagcttg ccctcatgaa ggagcttgtg     300
gaccttttgg ggctggagcg cctcgaggtc ccgggctttg aggcggacga tgtcctcgcc     360
gccctggcca agaaggcgga gcgggaaggg tacgaggtgc gcatcctcac cgccgaccgg     420
gacctcttcc agcttctttc ggaccgcatc gccgtcctgc acccggaagg ccacctcatc     480
accccggggt ggctttggga gaggtacggc ctgagaccgg agcagtgggt ggacttccgc     540
gccctggccg gcgacccttc cgacaacatc cccggggtga aggggatcgg cgagaagacg     600
gccctgaagc tcctaaagga gtggggtagt ctggaaaata tccaaaaaaa cctggaccag     660
gtcagtcccc cttccgtgcg cgagaagatc caggcccacc tggacgacct caggctctcc     720
```

-continued

```
caggagcttt cccgggtgcg cacggacctt cccttggagg tggactttag aaggcggcgg      780
gagcccgata gggaaggcct tagggccttc ttagagcggc ttgagttcgg gagcctcctc      840
cacgagttcg gcctcctgga aagccccag gcggcggagg aggcccttg gccgccgccg        900 gaagggcct tcttgggctt ccgcctctcc cggcccgagc ccatgtgggc ggaactcctt       960
tccttggcgg caagcgccaa gggcgggtc taccggcgg aggcgcccca taaggccctt       1020
tcggacctga aggagatccg ggggcttctc gccaaggacc tcgccgtctt ggccctgagg     1080
gaggggctcg gccttccccc cacggacgat cccatgctcc tcgcctacct cctggacccc     1140
tccaacacca ccccgaggg cgtggcccgg cgctacgggg gggagtggac ggaggaggcg      1200
ggggagaggg ccttgcttgc cgaaaggctt tacgagaacc tcctaagccg cctgaaaggg    1260
gaagaaaagc tcctttggct ctacgaggag gtggaaaagc ccctttcccg ggtcctcgcc    1320
cacatggagg ccacggggt gaggctggac gtaccctacc taagggccct ttccctggag     1380
gtggcggcgg agatgggccg cctggaggag gaggttttcc gcctggcggg ccacccctct    1440
aacctgaact cccgcgacca gctggaaagg gtgctctttg acgagctcgg gcttcccccc     1500
atcggcaaga cggaaaaac cgggaagcgc tccaccagcg ccgccgtcct cgaggccctg     1560
cgggaggccc accccatcgt ggagaagatc ctccagtacc gggagctcgc caagctcaag    1620
ggcacctaca ttgacctcct tcccgccctg gtccacccca ggacgggcag gctccacacc    1680
cgcttcaacc agacggccac ggcacgggc cgccttttca gctccgacccc caacctgcag    1740 aacattcccg tgcgcacccc cttgggccaa aggatccgcc gggccttcgt ggccgaggag    1800
gggtaccttc tcgtggccct ggactatagc cagattgagc tgagggtcct ggcccacctc    1860
tcgggggacg aaaacctcat ccgggtcttc caggagggcc gggacatcca cacccagacg    1920
gcgagctgga tgttcggcct gccggcggag gccatagacc ccctcaggcg ccgggcggcc    1980
aagaccatca acttcggcgt cctctacggc atgtccgccc accggctttc ccaggagctg    2040
ggcatcccct acgaggaggc ggtggccttc attgaccgct atttccagag ctaccccaag    2100
gtgaaggcct ggattgaaag gaccctggag gaggggcgg aaaggggta cgtggagacc      2160 ctcttcggcc gcaggcgcta cgtgcccgac ctcaacgccc gggtaaagag cgtgcgggag    2220
gcggcggagc gcatggcctt taacatgccc gtgcagggca ccgccgctga cctgatgaag    2280
ctcgccatgg tgaggctctt ccctaggctt cccgaggtgg gggcgaggat gctcctccag    2340
gtccacgacg agctcctcct ggaggcgccc aaggagcggg cggaggaggc ggcggccctg    2400
gccaaggagg tcatggaggg ggtctggccc ctggccgtgc ccctggaggt ggaggtgggc    2460
atcggggagg actggctttc cgccaagggc tag                                 2493
```

<210> SEQ ID NO 2
<211> LENGTH: 2498
<212> TYPE: DNA
<213> ORGANISM: Thermus brockianus

<400> SEQUENCE: 2

```
atgcttcccc tctttgagcc caagggccgg gtgctcctgg tggacggcca ccacctggcc      60
taccgtaact tcttcgccct caaggggctc accacgagcc ggggcgagcc cgtgcaaggg     120
gtctacggct tcgccaaaag cctcctcaag gccctgaagg aggacgggga cgtggtcatc     180
gtggtctttg acgccaaggc ccctctcttt cgccacgagg cctacggggc ctacaaggcg    240
ggccgggccc ctacccccgga ggactttccg aggcagcttg ccctcatgaa ggagcttgtg    300
gaccttttgg ggctggagcg cctcgaggtc ccgggctttg aggcggacga tgtcctcgcc    360
```

```
gccctggcca agaaggcgga gcgggaaggg tacgaggtgc gcatcctcac cgccgaccgg    420
gacctcttcc agcttctttc ggaccgcatc gccgtcctgc acccggaagg ccacctcatc    480
accccggggt ggctttggga gaggtacggc ctgagaccgg agcagtgggt ggacttccgc    540
gccctggccg gcgacccttc cgacaacatc cccggggtga aggggatcgg cgagaagacg    600
gccctgaagc tcctaaagga gtggggtagt ctggaaaata tccaaaaaaa cctggaccag    660
gtcagtcccc cttccgtgcg cgagaagatc caggcccacc tggacgacct caggctctcc    720
caggagcttt cccgggtgcg cacggacctt cccttggagg tggactttag aaggcggcgg    780
gagcccgata gggaaggcct tagggccttc ttagagcggc ttgagttcgg gagcctcctc    840
cacgagttcg gcctcctgga aagccccag gcggcggagg aggccccttg gccgccgccg    900 gaagggggcct tcttgggctt ccgcctctcc cggcccgagc ccatgtgggc ggaactcctt    960
tccttggcgg caagcgccaa gggccgggtc taccgggcgg aggcgcccca taaggccctt   1020
tcggacctga aggagatccg ggggcttctc gccaaggacc tcgccgtctt ggccctgagg   1080
gaggggctcg gccttccccc cacggacgat cccatgctcc tcgcctacct cctggacccc   1140
tccaacacca cccccgaggg cgtggcccgg cgctacgggg gggagtggac ggaggaggcg   1200
ggggagaggg ccttgcttgc cgaaaggctt tacgagaacc tcctaagccg cctgaaaggg   1260
gaagaaaagc tcctttggct ctacgaggag gtggaaaagc cccttttcccg ggtcctcgcc   1320 cacatggagg ccacggggt gaggctggac gtaccctacc taagggccct ttccctggag   1380
gtggcggcgg agatgggccg cctggaggag gaggttttcc gcctggcggg ccaccccttc   1440
aacctgaact cccgcgacca gctggaaagg gtgctctttg acgagctcgg gcttccccc   1500 atcggcaaga cggaaaaaac cgggaagcgc tccaccagcg ccgccgtcct cgaggccctg   1560
cgggaggccc accccatcgt ggagaagatc ctccagtacc gggagctcgc caagctcaag   1620
ggcacctaca ttgaccccct tcccgccctg gtccaccccca ggacgggcag gctccacacc   1680
cgcttcaacc agacggccac ggccacgggc cgccttttcca gctccgaccc caacctgcag   1740
aacattcccg tgcgcacccc cttgggccaa aggatccgcc gggccttcgt ggccgaggag   1800
gggtaccttc tcgtggccct ggactatagc cagattgagc tgagggtcct ggcccacctc   1860 tcggggggacaa aaaacctcat ccgggtcttc caggagggcc gggacatcca cacccagacg   1920
gcgagctgga tgttcggcct gccggcggag gccatagacc ccctcaggcg ccgggcggcc   1980
aagaccatca acttcggcgt cctctacggc atgtccgccc accggctttc ccaggagctg   2040
ggcatcccct acgaggaggc ggtggccttc attgaccgct atttccagag ctaccccaag   2100
gtgaaggcct ggattgaaag gaccctggag gaggggcggc aaaggggggta cgtggagacc   2160 ctcttcggcc gcaggcgcta cgtgcccgac ctcaacgccc gggtaaagag cgtgcgggag   2220
gcggcggagc gcatggcctt taacatgccc gtgcagggca ccgccgctga cctgatgaag   2280
ctcgccatgg tgaggctctt ccctaggctt cccgaggtgg gggcgaggat gctcctccag   2340
gtccacgacg agctcctcct ggaggcgccc aaggagcggg cggaggaggc ggcggccctg   2400
gccaaggagg tcatggaggg agtctggccc ctggccgtgc ccctggaggt ggaggtgggc   2460
atcggggagg actggctttc cgccaagggc tagtcgac                          2498
```

<210> SEQ ID NO 3
<211> LENGTH: 2493
<212> TYPE: DNA
<213> ORGANISM: Thermus brockianus

<400> SEQUENCE: 3

```
atgcttcccc tctttgagcc caagggccgg gtgctcctgg tggacggcca ccacctggcc    60
taccgtaact tcttcgccct caaggggctc accacgagcc ggggcgagcc cgtgcaaggg   120
gtctacgact tcgccaaaag cctcctcaag gccctgaagg aggacgggga cgtggtcatc   180
gtggtctttg acgccaaggc cccctctttt cgccacgagg cctacggggc ctacaaggcg   240
ggccgggccc ctaccccgga ggactttccg aggcagcttg ccctcatgaa ggagcttgtg   300
gacctttgg ggctggagcg cctcgaggtc ccgggctttg aggcggacga tgtcctcgcc   360
gccctggcca agaaggcgga gcggaagggt acgaggtgc gcatcctcac cgccgaccgg   420
gacctcttcc agcttctttc ggaccgcatc gccgtcctgc acccggaagg ccacctcatc   480
accccggggt ggctttggga gaggtacggc ctgagaccgg agcagtgggt ggacttccgc   540
gccctggccg gcgacccttc cgacaacatc cccggggtga aggggatcgg cgagaagacg   600
gccctgaagc tcctaaagga gtggggtagt ctggaaaata ccaaaaaaa cctggaccag   660
gtcagtcccc cttccgtgcg cgagaagatc caggcccacc tggacgacct caggctctcc   720
caggagcttt cccgggtgcg cacggacctt cccttggagg tggactttag aaggcggcgg   780
gagcccgata gggaaggcct tagggccttc ttagagcggc ttgagttcgg gagcctcctc   840
cacgagttcg gcctcctgga aagccccag gcggcggagg aggccccttg gccgccgccg   900
gaagggcct tcttgggctt ccgcctctcc cggcccgagc catgtgggc ggaactcctt   960
tccttggcgg caagcgccaa gggccgggtc taccgggcgg aggcgcccca taaggccctt  1020
tcggacctga aggagatccg ggggcttctc gccaaggacc tcgccgtctt ggccctgagg  1080
gagggctcg gccttccccc cacggacgat cccatgctcc tcgcctacct cctggacccc  1140
tccaacacca ccccgaggg cgtggcccgg cgctacgggg gggagtggac ggaggaggcg  1200
ggggagaggg ccttgcttgc cgaaaggctt tacgagaacc tcctaagccg cctgaaaggg  1260
gaagaaaagc tcctttggct ctacgaggag gtggaaaagc cccttttccg ggtcctcgcc  1320
cacatggagg ccacggggt gaggctggac gtaccctacc taagggccct ttccctggag  1380
gtggcggcgg agatgggccg cctggaggag gaggttttcc gcctggcggg ccacccttc  1440
aacctgaact cccgcgacca gctggaaagg gtgctctttg acgagctcgg gcttcccccc  1500
atcggcaaga cggaaaaaac cgggaagcgc tccaccagcg ccgccgtcct cgaggccctg  1560
cgggaggccc accccatcgt ggagaagatc ctccagtacc gggagctcgc caagctcaag  1620
ggcacctaca ttgacctcct tcccgccctg gtccacccca ggacgggcag gctccacacc  1680
cgcttcaacc agacggccac ggccacgggc cgccttttcca gctccgaccc caacctgcag  1740
aacattcccg tgcgcacccc cttgggccaa aggatccgcc gggccttcgt ggccgaggag  1800
gggtaccttc tcgtggccct ggactatagc cagattgagc tgagggtcct ggcccacctc  1860
tcggggacg aaaacctcat ccgggtcttc caggagggcc gggacatcca cacccagacg  1920
gcgagctgga tgttcggcct gccggcggag gccatagacc ccctcaggcg ccgggcggcc  1980
aagaccatca acttcggcgt cctctacggc atgtccgccc accggctttc ccaggagctg  2040
ggcatcccct acgaggaggc ggtggccttc attgaccgcg atttccagag ctaccccaag  2100
gtgaaggcct ggattgaaag gaccctggag gagggcggc aaaggggta cgtggagacc  2160
ctcttcggcc gcaggcgcta cgtgcccgac ctcaacgccc gggtaaagag cgtgcggag  2220
gcggcggagc gcatggcctt taacatgccc gtgcagggca ccgccgctga cctgatgaag  2280
ctcgccatgt gaggctctt ccctaggctt cccgaggtgg gggcgaggat gctcctccag  2340
gtccacgacg agctcctcct ggaggcgccc aaggagcggg cggaggaggc ggcggccctg  2400
```

```
gccaaggagg tcatggaggg ggtctggccc ctggccgtgc ccctggaggt ggaggtgggc      2460
atcggggagg actggctttc cgccaagggc tag                                  2493

<210> SEQ ID NO 4
<211> LENGTH: 2498
<212> TYPE: DNA
<213> ORGANISM: Thermus brockianus

<400> SEQUENCE: 4
atgcttcccc tctttgagcc caagggccgg gtgctcctgg tggacggcca ccacctggcc       60
taccgtaact tcttcgccct caaggggctc accacgagcc gggcgagcc cgtgcaaggg      120 gtctacgact tcgccaaaag cctcctcaag gccctgaagg aggacgggga cgtggtcatc      180
gtggtctttg acgccaaggc ccctctcttt cgccacgagg cctacgggg ctacaaggcg      240 ggccgggccc ctaccccgga ggactttccg aggcagcttg ccctcatgaa ggagcttgtg      300
gacctttggg gctggagcg cctcgaggtc ccgggctttg aggcggacga tgtcctcgcc      360
gccctggcca agaaggcgga gcggaaggg tacgaggtgc gcatcctcac cgccgaccgg      420
gacctcttcc agcttctttc ggaccgcatc gccgtcctgc accggaagg ccacctcatc      480 accccggggt ggctttggga gaggtacggc ctgagaccgg agcagtgggt ggacttccgc      540
gccctggccg cgaccccttc cgacaacatc cccggggtga aggggatcgg cgagaagacg      600
gccctgaagc tcctaaagga gtggggtagt ctggaaaata tccaaaaaaa cctggaccag      660
gtcagtcccc cttccgtgcg cgagaagatc caggcccacc tggacgacct caggctctcc      720
caggagcttt cccgggtgcg cacggacctt cccttggagg tggactttag aaggcggcgg      780
gagcccgata gggaaggcct tagggcctcc ttagagcggc ttgagttcgg gagcctcctc      840
cacgagttcg gcctcctgga aagcccccag gcggcggagg aggcccttg gccgccgccg      900 gaagggcct tcttgggctt ccgctctctcc cggcccgagc ccatgtgggc ggaactcctt      960
tccttggcgg caagcgccaa gggccgggtc taccggcgg aggcgcccca taaggccctt     1020
tcggacctga aggagatccg ggggcttctc gccaaggacc tcgccgtctt ggccctgagg     1080
gaggggctcg gccttccccc cacggacgat cccatgctcc tcgcctacct cctggacccc     1140
tccaacacca ccccgaggg cgtggcccgg cgctacgggg gggagtggac ggaggaggcg     1200
ggggagaggg ccttgcttgc cgaaaggctt tacgagaacc tcctaagccg cctgaaaggg     1260
gaagaaaagc tcctttggct ctacgaggag gtggaaaagc ccctttccg ggtcctcgcc     1320 cacatggagg ccacggggg gaggctggac gtaccctacc taagggccct ttccctggag     1380
gtggcggcgg agatgggccg cctggaggag gaggttttcc gcctggcggg ccacccttc     1440 aacctgaact cccgcgacca gctggaaagg gtgctctttg acgagctcgg gcttcccccc     1500
atcggcaaga cggaaaaaac cgggaagcgc tccaccagcg ccgccgtcct cgaggccctg     1560
cgggaggccc accccatcgt ggagaagatc ctccagtacc gggagctcgc caagctcaag     1620
ggcacctaca ttgacccct tcccgccctg gtccacccca ggacgggcag gctccacacc     1680
cgcttcaacc agacggccac ggccacgggc cgccttttcca gctccgaccc caacctgcag     1740
aacattcccg tgcgcaccc cttgggccaa aggatccgcc gggccttcgt ggccgaggag     1800
gggtaccttc tcgtggccct ggactatagc cagattgagc tgagggtcct ggcccacctc     1860
tcgggggacg aaaaccctcat ccgggtcttc caggagggcc gggacatcca cacccagacg     1920
gcgagctgga tgttcggcct gccggcgag gccatagacc ccctcaggcg ccgggcggcc     1980
aagaccatca acttcggcgt cctctacggc atgtccgccc accggctttc ccaggagctg     2040
```

```
ggcatcccct acgaggaggc ggtggccttc attgaccgct atttccagag ctaccccaag    2100
gtgaaggcct ggattgaaag gaccctggag gaggggcggc aaaggggta cgtggagacc    2160 ctcttcggcc gcaggcgcta cgtgcccgac ctcaacgccc gggtaaagag cgtgcgggag    2220
gcggcggagc gcatggcctt taacatgccc gtgcaggca ccgccgctga cctgatgaag    2280
ctcgccatgg tgaggctctt ccctaggctt cccgaggtgg gggcgaggat gctcctccag    2340
gtccacgacg agctcctcct ggaggcgccc aaggagcggg cggaggaggc ggcggccctg    2400
gccaaggagg tcatggaggg agtctggccc ctggccgtgc ccctggaggt ggaggtgggc    2460
atcggggagg actggctttc cgccaagggc tagtcgac                           2498

<210> SEQ ID NO 5
<211> LENGTH: 2493
<212> TYPE: DNA
<213> ORGANISM: Thermus brockianus

<400> SEQUENCE: 5
atgcttcccc tctttgagcc caagggccgg gtgctcctgg tggacggcca ccacctggcc     60
taccgtaact tcttcgccct caaggggctc accacgagcc ggggcgagcc cgtgcaaggg    120
gtctacggct cgccaaaaag cctcctcaag gccctgaagg aggacgggga cgtggtcatc    180
gtggtctttg acgccaaggc cccctctttt cgccacgagg cctacggggc ctacaaggcg    240
ggccgggccc ctaccccgga ggactttccg aggcagcttg ccctcatgaa ggagcttgtg    300
gaccttttgg gctgagagcg cctcgaggtc cgggctttg aggcggacga tgtcctcgcc    360
gccctggcca agaaggcgga gcgggaaggg tacgaggtgc gcatcctcac cgccgaccgg    420
gacctcttcc agcttctttc ggaccgcatc gccgtcctgc accggaagg ccacctcatc    480 acccccgggt ggctttggga gaggtacggc ctgagaccgg agcagtgggt ggacttccgc    540
gccctggccg cgacccctc cgacaacatc ccggggtga aggggatcgg cgagaagacg    600
gccctgaagc tcctaaagga gtggggtagt ctggaaaata ccaaaaaaa cctggaccag    660 gtcagtcccc cttccgtgcg cgagaagatc caggcccacc tggacgacct caggctctcc    720
caggagcttt cccgggtgcg cacggacctt cccttggagg tggactttag aaggcggcgg    780
gagcccgata gggaaggcct tagggccttc ttagagcggc ttgagttcgg gagcctcctc    840
cacgagttcg gcctcctgga aagccccag gcggcggagg aggccccttg gccgccgccg    900 gaagggggcct tctttgggctt ccgctctctc cggcccgagc ccatgtgggc ggaactcctt    960
tccttggcgg caagcgccaa gggccgggtc taccgggcgg aggcgcccca taaggccctt   1020
tcggacctga aggagatccg ggggcttctc gccaaggacc tcgccgtctt ggccctgagg   1080 gagggggctcg gccttcccc cacggacgat cccatgctcc tcgcctacct cctggacccc   1140
tccaacacca ccccgaggg cgtgggccgg cgctacgggg gggagtggac ggaggaggcg   1200
ggggagaggg ccttgcttgc cgaaaggctt tacgagaacc tcctaagccg cctgaaaggg   1260
gaagaaaagc tccttttggct ctacgaggag gtgaaaagc ccctttcccg ggtcctcgcc   1320
cacatggagg ccacgggggt gaggctggac gtaccctacc taagggccct ttccctggag   1380
gtggcggcgg agatgggccg cctggaggag gaggttttcc gcctggcggg ccaccccttc   1440
aacctgaact cccgcgacca gctggaaagg gtgctctttg acgagctcgg gcttccccc   1500 atcggcaaga cggaaaaaac cgggaagcgc tccaccagcg ccgccgtcct cgaggccctg   1560
cgggaggccc accccatcgt ggagaagatc ctccagtacc gggagctcgc caagctcaag   1620
ggcacctaca ttgacctcct tcccgccctg gtccacccca ggacgggcag gctccacacc   1680
```

```
cgcttcaacc agacggccac ggccacgggc cgccttccca gctccgaccc caacctgcag    1740
aacattcccg tgcgcacccc cttgggccaa aggatccgcc gggccttcgt ggccgaggag    1800
gggtaccttc tcgtggccct ggactatagc cagattgagc tgagggtcct ggcccacctc    1860 tcggggacg aaaacctcat ccgggtcttc caggagggcc gggacatcca cacccagacg     1920
gcgagctgga tgttcggcct gccggcgag gccatagacc ccctcaggcg ccgggcggcc     1980
aagaccatca actacggcgt cctctacggc atgtccgccc accggctttc ccaggagctg    2040
ggcatcccct acgaggaggc ggtggccttc attgaccgct atttccagag ctaccccaag    2100
gtgaaggcct ggattgaaag gaccctggag gaggggcggc aaagggggta cgtggagacc    2160
ctcttcggcc gcaggcgcta cgtgcccgac ctcaacgccc gggtaaagag cgtgcgggag    2220
gcggcggagc gcatggcctt taacatgccc gtgcagggca ccgccgctga cctgatgaag    2280
ctcgccatgg tgaggctctt ccctaggctt cccgaggtgg gggcgaggat gctcctccag    2340
gtccacgacg agctcctcct ggaggcgccc aaggagcggg cggaggaggc ggcggccctg    2400
gccaaggagg tcatggaggg ggtctggccc ctggccgtgc ccctggaggt ggaggtgggc    2460
atcggggagg actggctttc cgccaagggc tag                                  2493

<210> SEQ ID NO 6
<211> LENGTH: 2498
<212> TYPE: DNA
<213> ORGANISM: Thermus brockianus

<400> SEQUENCE: 6
atgcttcccc tctttgagcc caagggccgg gtgctcctgg tggacggcca ccacctggcc     60
taccgtaact tcttcgccct caaggggctc accacgagcc ggggcgagcc cgtgcaaggg    120
gtctacggct tcgccaaaag cctcctcaag gccctgaagg aggacgggga cgtggtcatc    180
gtggtctttg acgccaaggc cccctctttt cgccacgagg cctacgggg ctacaaggcg     240 ggccgggccc ctaccccgga ggactttccg aggcagcttg ccctcatgaa ggagcttgtg    300
gaccttttgg ggctggagcg cctcgaggtc ccgggctttg aggcggacga tgtcctcgcc    360
gccctggcca agaaggcgga gcgggaaggg tacgaggtgc gcatcctcac cgccgaccgg    420
gacctcttcc agcttctttc ggaccgcatc gccgtcctgc acccggaagg ccacctcatc    480
accccggggt ggctttggga gaggtacggc ctgagaccgg agcagtgggt ggacttccgc    540
gccctggccg gcgaccccttc cgacaacatc cccggggtga aggggatcgg cgagaagacg    600
gccctgaagc tcctaaagga gtgggtagt ctggaaaata ccaaaaaaaa cctggaccag    660
gtcagtcccc cttccgtgcg cgagaagatc caggcccacc tggacgacct caggctctcc    720
caggagcttt cccgggtgcg cacggacctt cccttggagg tggactttag aaggcggcgg    780
gagcccgata gggaaggcct tagggccttc ttagagcggc ttgagttcgg gagcctcctc    840
cacgagttcg gcctcctgga aagcccccag gcggcggagg aggcccttg gccgccgccg    900 gaagggccct tcttgggctt ccgcctctcc cggcccgagc ccatgtgggc ggaactcctt    960
tccttggcgg caagcgccaa gggccgggtc taccgggcgg aggcgcccca taaggccctt   1020
tcggacctga aggagatccg ggggcttctc gccaaggacc tcgccgtctt ggccctgagg   1080
gaggggctcg gccttccccc cacggacgat cccatgctcc tcgcctacct cctggacccc   1140
tccaacacca cccccgaggg cgtggcccgg cgctacgggg gggagtggac ggaggaggcg    1200
ggggagaggg ccttgcttgc cgaaaggctt tacgagaacc tcctaagccg cctgaaaggg   1260
gaagaaaagc tcctttggct ctacgaggag gtggaaaagc cccttttcccg ggtcctcgcc   1320
```

```
cacatggagg ccacggggt gaggctggac gtaccctacc taagggccct ttccctggag    1380
gtggcggcgg agatgggccg cctggaggag gaggttttcc gcctggcggg ccaccccttc    1440
aacctgaact cccgcgacca gctggaaagg gtgctctttg acgagctcgg gcttccccc    1500
atcggcaaga cggaaaaaac cgggaagcgc tccaccagcg ccgccgtcct cgaggccctg    1560
cgggaggccc accccatcgt ggagaagatc ctccagtacc gggagctcgc caagctcaag    1620
ggcacctaca ttgacccct tcccgccctg gtccaccca ggacgggcag gctccacacc    1680
cgcttcaacc agacgccac ggccacgggc cgcctttcca gctccgaccc caacctgcag    1740
aacattcccg tgcgcacccc cttgggccaa aggatccgcc gggccttcgt ggccgaggag    1800
gggtaccttc tcgtggccct ggactatagc cagattgagc tgagggtcct ggcccacctc    1860
tcggggacg aaaacctcat ccgggtcttc caggagggcc gggacatcca cacccagacg    1920
gcgagctgga tgttcggcct gccggcggag gccatagacc ccctcaggcg ccgggcggcc    1980
aagaccatca actacggcgt cctctacggc atgtccgccc accggctttc ccaggagctg    2040
ggcatcccct acgaggaggc ggtggccttc attgaccgct atttccagag ctaccccaag    2100
gtgaaggcct ggattgaaag gaccctggag gaggggcgg aaaggggta cgtggagacc    2160
ctcttcggcc gcaggcgcta cgtgcccgac ctcaacgccc gggtaaagag cgtgcgggag    2220
gcggcggagc gcatggcctt taacatgccc gtgcagggca ccgccgctga cctgatgaag    2280
ctcgccatgg tgaggctctt ccctaggctt cccgaggtgg gggcgaggat gctcctccag    2340
gtccacgacg agctcctcct ggaggcgccc aaggagcggg cggaggaggc ggcggccctg    2400
gccaaggagg tcatggaggg agtctggccc ctggccgtgc ccctggaggt ggaggtgggc    2460
atcggggagg actggctttc cgccaagggc tagtcgac                          2498

<210> SEQ ID NO 7
<211> LENGTH: 2493
<212> TYPE: DNA
<213> ORGANISM: Thermus brockianus

<400> SEQUENCE: 7
atgcttcccc tcttttgagcc caagggccgg gtgctcctgg tggacggcca ccacctggcc      60
taccgtaact tcttcgccct caaggggctc accacgagcc gggcgagcc cgtgcaaggg     120
gtctacgact tcgccaaaag cctcctcaag gccctgaagg aggacgggga cgtggtcatc     180
gtggtctttg acgccaaggc ccctctcttt cgccacgagg cctacggggc ctacaaggcg     240
ggccgggccc ctaccccgga ggacttccg aggcagcttg ccctcatgaa ggagcttgtg     300
gaccttttgg ggctggagcg cctcgaggtc ccgggctttg aggcggacga tgtcctcgcc     360
gccctggcca agaaggcgga gcgggaaggg tacgaggtgc gcatcctcac cgccgaccgg     420
gacctcttcc agcttctttc ggaccgcatc gccgtcctgc acccgaagg ccacctcatc     480
acccggggt ggctttggga ggtacggc ctgagaccgg agcagtgggt ggacttccgc     540
gccctggccg cgacccttc cgacaacatc cccggggtga aggggatcgg cgagaagacg     600
gccctgaagc tcctaaagga gtgggtagt ctggaaaata tccaaaaaaa cctggaccag     660
gtcagtcccc cttccgtgcg cgagaagatc caggcccacc tggacgacct caggctctcc     720
caggagcttt cccgggtgcg cacggacctt cccttggagg tggactttag aaggcggcgg     780
gagcccgata gggaaggcct taggccttc ttagagcgcg ttgagttcgg gagcctcctc     840
cacgagttcg gcctcctgga aagcccccag gcggcggagg aggcccctg gccgccgccg     900
gaagggcct tcttgggctt ccgcctctcc cggcccgagc ccatgtgggc ggaactcctt     960
```

-continued

```
tccttggcgg caagcgccaa gggccgggtc taccgggcgg aggcgcccca taaggcccTT    1020
tcggacctga aggagatccg ggggcttctc gccaaggacc tcgccgtctt ggccctgagg    1080
gaggggctcg gccttccccc cacggacgat cccatgctcc tcgcctacct cctggacccc    1140
tccaacacca cccccgaggg cgtggcccgg cgctacgggg gggagtggac ggaggaggcg    1200
ggggagaggg ccttgcttgc cgaaaggctt tacgagaacc tcctaagccg cctgaaaggg    1260
gaagaaaagc tcctttggct ctacgaggag gtggaaaagc ccctttcccg ggtcctcgcc    1320
cacatggagg ccacggggt gaggctggac gtaccctacc taagggccct ttccctggag     1380
gtggcggcgg agatgggccg cctggaggag gaggttttcc gcctggcggg ccacccctcc    1440
aacctgaact cccgcgacca gctggaaagg gtgctctttg acgagctcgg gcttcccccc    1500
atcggcaaga cggaaaaaac cgggaagcgc tccaccagcg ccgccgtcct cgaggccctg    1560
cgggaggccc accccatcgt ggagaagatc ctccagtacc gggagctcgc caagctcaag    1620
ggcacctaca ttgacctcct tcccgccctg gtccacccca ggacgggcag gctccacacc    1680
cgcttcaacc agacggccac ggccacgggc cgccttttcca gctccgaccc caacctgcag    1740
aacattcccg tgcgcacccc cttgggccaa aggatccgcc gggccttcgt ggccgaggag    1800
gggtaccttc tcgtggccct ggactatagc cagattgagc tgagggtcct ggcccacctc    1860
tcgggggacg aaaacctcat ccgggtcttc caggagggcc gggacatcca cacccagacg    1920
gcgagctgga tgttcggcct gccggcggag gccatagacc ccctcaggcg ccgggcggcc    1980
aagaccatca actacggcgt cctctacggc atgtccgccc accggctttc ccaggagctg    2040
ggcatcccct acgaggaggc ggtggccttc attgaccgct atttccagag ctaccccaag    2100
gtgaaggcct ggattgaaag gaccctggag gaggggcggc aaaggggta cgtggagacc     2160 ctcttcggcc gcaggcgcta cgtgcccgac ctcaacgccc gggtaaagag cgtgcgggag    2220
gcggcggagc gcatggcctt taacatgccc gtgcagggca ccgccgctga cctgatgaag    2280
ctcgccatgg tgaggctctt ccctaggctt cccgaggtgg gggcgaggat gctcctccag    2340
gtccacgacg agctcctcct ggaggcgccc aaggagcggg cggaggaggc ggcggccctg    2400
gccaaggagg tcatggaggg ggtctggccc ctggccgtgc ccctggaggt ggaggtgggc    2460
atcggggagg actggctttc cgccaagggc tag                                2493
```

<210> SEQ ID NO 8
<211> LENGTH: 2498
<212> TYPE: DNA
<213> ORGANISM: Thermus brockianus

<400> SEQUENCE: 8

```
atgcttcccc tctttgagcc caagggccgg gtgctcctgg tggacggcca ccacctggcc      60
taccgtaact tcttcgccct caaggggctc accacgagcc ggggcgagcc cgtgcaaggg     120
gtctacgact tcgccaaaag cctcctcaag gccctgaagg aggacgggga cgtggtcatc     180
gtggtctttg acgccaaggc cccctctttt cgccacgagg cctacggggc ctacaaggcg     240
ggccgggccc tacccccgga ggactttccg aggcagcttg ccctcatgaa ggagcttgtg     300
gaccttttgg ggctggagcg cctcgaggtc ccgggctttg aggcggacga tgtcctcgcc    360
gccctggcca agaaggcgga gcgggaaggg tacgaggtgc gcatcctcac cgccgaccgg    420
gacctcttcc agcttctttc ggaccgcatc gccgtcctgc accggaaggg ccacctcatc    480
acccccgggt ggctttggga gaggtacggc ctgagaccgg agcagtgggt ggacttccgc    540
gccctggccg gcgaccccttc cgacaacatc cccggggtga aggggatcgg cgagaagacg    600
```

```
gccctgaagc tcctaaagga gtggggtagt ctggaaaata tccaaaaaaa cctggaccag    660
gtcagtcccc cttccgtgcg cgagaagatc caggcccacc tggacgacct caggctctcc    720
caggagcttt cccgggtgcg cacggacctt cccttggagg tggactttag aaggcggcgg    780
gagcccgata gggaaggcct tagggccttc ttagagcggc ttgagttcgg gagcctcctc    840
cacgagttcg gcctcctgga aagccccag gcggcggagg aggcccttg gccgccgccg    900 gaagggcct tcttgggctt ccgcctctcc cggcccgagc ccatgtgggc ggaactcctt    960
tccttggcgg caagcgccaa gggcggggtc taccgggcgg aggcgcccca taaggccctt   1020
tcggacctga aggagatccg ggggcttctc gccaaggacc tcgccgtctt ggccctgagg   1080
gaggggctcg gccttccccc cacggacgat cccatgctcc tcgcctacct cctggacccc   1140
tccaacacca ccccgaggg cgtggcccgg cgctacgggg gggagtggac ggaggaggcg   1200
ggggagaggg ccttgcttgc cgaaaggctt tacgagaacc tcctaagccg cctgaaaggg   1260
gaagaaaagc tcctttggct ctacgaggag gtggaaaagc cccttttcccg ggtcctcgcc   1320 cacatggagg ccacggggt gaggctggac gtaccctacc taagggcct ttccctggag   1380 gtggcggcg agatgggccg cctggaggag gaggttttcc gcctggcggg ccaccccttc   1440
aacctgaact cccgcgacca gctggaaagg gtgctctttg acgagctcgg gcttccccc   1500 atcggcaaga cggaaaaaac cgggaagcgc tccaccagcg ccgccgtcct cgaggccctg   1560
cgggaggccc accccatcgt ggagaagatc ctccagtacc gggagctcgc caagctcaag   1620
ggcacctaca ttgaccccct tcccgccctg gtccaccca ggacgggcag gctccacacc   1680
cgcttcaacc agacggccac ggccacgggc cgccttttcca gctccgaccc caacctgcag   1740
aacattcccg tgcgcacccc cttgggccaa aggatccgcc gggccttcgt ggccgaggag   1800
gggtaccttc tcgtggccct ggactatagc cagattgagc tgagggtcct ggcccacctc   1860 tcggggggacg aaaacctcat ccgggtcttc caggagggcc gggacatcca cacccagacg   1920
gcgagctgga tgttcggcct gccggcggag gccatagacc ccctcaggcg ccgggcggcc   1980
aagaccatca actacggcgt cctctacggc atgtccgccc ccggctttc ccaggagctg   2040 ggcatcccct acgaggaggc ggtggccttc attgaccgct atttccagag ctaccccaag   2100
gtgaaggcct ggattgaaag gaccctggag gaggggcggc aaaggggggta cgtggagacc   2160 ctcttcggcc gcaggcgcta cgtgcccgac ctcaacgccc gggtaaagag cgtgcgggag   2220
gcggcggagc gcatggcctt taacatgccc gtgcagggca ccgccgctga cctgatgaag   2280
ctcgccatgg tgaggctctt ccctaggctt cccgaggtgg gggcgaggat gctcctccag   2340
gtccacgacg agctcctcct ggaggcgccc aaggagcggg cggaggaggc ggcggccctg   2400
gccaaggagg tcatggaggg agtctggccc ctggccgtgc ccctggaggt ggaggtgggc   2460
atcggggagg actggctttc cgccaagggc tagtcgac                          2498
```

<210> SEQ ID NO 9
<211> LENGTH: 830
<212> TYPE: PRT
<213> ORGANISM: Thermus brockianus

<400> SEQUENCE: 9

Met Leu Pro Leu Phe Glu Pro Lys Gly Arg Val Leu Leu Val Asp Gly
1               5                  10                  15

His His Leu Ala Tyr Arg Asn Phe Phe Ala Leu Lys Gly Leu Thr Thr
            20                  25                  30

Ser Arg Gly Glu Pro Val Gln Gly Val Tyr Gly Phe Ala Lys Ser Leu

-continued

```
                35                  40                  45
Leu Lys Ala Leu Lys Glu Asp Gly Asp Val Val Ile Val Val Phe Asp
 50                  55                  60
Ala Lys Ala Pro Ser Phe Arg His Glu Ala Tyr Gly Ala Tyr Lys Ala
 65                  70                  75                  80
Gly Arg Ala Pro Thr Pro Glu Asp Phe Pro Arg Gln Leu Ala Leu Met
                 85                  90                  95
Lys Glu Leu Val Asp Leu Leu Gly Leu Glu Arg Leu Glu Val Pro Gly
            100                 105                 110
Phe Glu Ala Asp Asp Val Leu Ala Ala Leu Ala Lys Lys Ala Glu Arg
            115                 120                 125
Glu Gly Tyr Glu Val Arg Ile Leu Thr Ala Asp Arg Asp Leu Phe Gln
            130                 135                 140
Leu Leu Ser Asp Arg Ile Ala Val Leu His Pro Glu Gly His Leu Ile
145                 150                 155                 160
Thr Pro Gly Trp Leu Trp Glu Arg Tyr Gly Leu Arg Pro Glu Gln Trp
                165                 170                 175
Val Asp Phe Arg Ala Leu Ala Gly Asp Pro Ser Asp Asn Ile Pro Gly
            180                 185                 190
Val Lys Gly Ile Gly Glu Lys Thr Ala Leu Lys Leu Leu Lys Glu Trp
            195                 200                 205
Gly Ser Leu Glu Asn Ile Gln Lys Asn Leu Asp Gln Val Ser Pro Pro
210                 215                 220
Ser Val Arg Glu Lys Ile Gln Ala His Leu Asp Asp Leu Arg Leu Ser
225                 230                 235                 240
Gln Glu Leu Ser Arg Val Arg Thr Asp Leu Pro Leu Glu Val Asp Phe
                245                 250                 255
Arg Arg Arg Arg Glu Pro Asp Arg Glu Gly Leu Arg Ala Phe Leu Glu
            260                 265                 270
Arg Leu Glu Phe Gly Ser Leu Leu His Glu Phe Gly Leu Leu Glu Ser
            275                 280                 285
Pro Gln Ala Ala Glu Glu Ala Pro Trp Pro Pro Glu Gly Ala Phe
            290                 295                 300
Leu Gly Phe Arg Leu Ser Arg Pro Glu Pro Met Trp Ala Glu Leu Leu
305                 310                 315                 320
Ser Leu Ala Ala Ser Ala Lys Gly Arg Val Tyr Arg Ala Glu Ala Pro
                325                 330                 335
His Lys Ala Leu Ser Asp Leu Lys Glu Ile Arg Gly Leu Leu Ala Lys
            340                 345                 350
Asp Leu Ala Val Leu Ala Leu Arg Glu Gly Leu Gly Leu Pro Pro Thr
            355                 360                 365
Asp Asp Pro Met Leu Leu Ala Tyr Leu Leu Asp Pro Ser Asn Thr Thr
            370                 375                 380
Pro Glu Gly Val Ala Arg Arg Tyr Gly Gly Glu Trp Thr Glu Glu Ala
385                 390                 395                 400
Gly Glu Arg Ala Leu Leu Ala Glu Arg Leu Tyr Glu Asn Leu Leu Ser
            405                 410                 415
Arg Leu Lys Gly Glu Glu Lys Leu Leu Trp Leu Tyr Glu Glu Val Glu
            420                 425                 430
Lys Pro Leu Ser Arg Val Leu Ala His Met Glu Ala Thr Gly Val Arg
            435                 440                 445
Leu Asp Val Pro Tyr Leu Arg Ala Leu Ser Leu Glu Val Ala Ala Glu
450                 455                 460
```

```
Met Gly Arg Leu Glu Glu Val Phe Arg Leu Ala Gly His Pro Phe
465                 470                 475                 480

Asn Leu Asn Ser Arg Asp Gln Leu Glu Arg Val Leu Phe Asp Glu Leu
            485                 490                 495

Gly Leu Pro Pro Ile Gly Lys Thr Glu Lys Thr Gly Lys Arg Ser Thr
        500                 505                 510

Ser Ala Ala Val Leu Glu Ala Leu Arg Glu Ala His Pro Ile Val Glu
        515                 520                 525

Lys Ile Leu Gln Tyr Arg Glu Leu Ala Lys Leu Lys Gly Thr Tyr Ile
530                 535                 540

Asp Leu Leu Pro Ala Leu Val His Pro Arg Thr Gly Arg Leu His Thr
545                 550                 555                 560

Arg Phe Asn Gln Thr Ala Thr Ala Thr Gly Arg Leu Ser Ser Ser Asp
                565                 570                 575

Pro Asn Leu Gln Asn Ile Pro Val Arg Thr Pro Leu Gly Gln Arg Ile
                580                 585                 590

Arg Arg Ala Phe Val Ala Glu Glu Gly Tyr Leu Leu Val Ala Leu Asp
            595                 600                 605

Tyr Ser Gln Ile Glu Leu Arg Val Leu Ala His Leu Ser Gly Asp Glu
610                 615                 620

Asn Leu Ile Arg Val Phe Gln Glu Gly Arg Asp Ile His Thr Gln Thr
625                 630                 635                 640

Ala Ser Trp Met Phe Gly Leu Pro Ala Glu Ala Ile Asp Pro Leu Arg
                645                 650                 655

Arg Arg Ala Ala Lys Thr Ile Asn Phe Gly Val Leu Tyr Gly Met Ser
            660                 665                 670

Ala His Arg Leu Ser Gln Glu Leu Gly Ile Pro Tyr Glu Glu Ala Val
        675                 680                 685

Ala Phe Ile Asp Arg Tyr Phe Gln Ser Tyr Pro Lys Val Lys Ala Trp
        690                 695                 700

Ile Glu Arg Thr Leu Glu Glu Gly Arg Gln Arg Gly Tyr Val Glu Thr
705                 710                 715                 720

Leu Phe Gly Arg Arg Tyr Val Pro Asp Leu Asn Ala Arg Val Lys
                725                 730                 735

Ser Val Arg Glu Ala Ala Glu Arg Met Ala Phe Asn Met Pro Val Gln
            740                 745                 750

Gly Thr Ala Ala Asp Leu Met Lys Leu Ala Met Val Arg Leu Phe Pro
        755                 760                 765

Arg Leu Pro Glu Val Gly Ala Arg Met Leu Leu Gln Val His Asp Glu
770                 775                 780

Leu Leu Leu Glu Ala Pro Lys Glu Arg Ala Glu Glu Ala Ala Ala Leu
785                 790                 795                 800

Ala Lys Glu Val Met Glu Gly Val Trp Pro Leu Ala Val Pro Leu Glu
                805                 810                 815

Val Glu Val Gly Ile Gly Glu Asp Trp Leu Ser Ala Lys Gly
            820                 825                 830

<210> SEQ ID NO 10
<211> LENGTH: 830
<212> TYPE: PRT
<213> ORGANISM: Thermus brockianus

<400> SEQUENCE: 10

Met Leu Pro Leu Phe Glu Pro Lys Gly Arg Val Leu Leu Val Asp Gly
1               5                   10                  15
```

```
His His Leu Ala Tyr Arg Asn Phe Phe Ala Leu Lys Gly Leu Thr Thr
             20                  25                  30

Ser Arg Gly Glu Pro Val Gln Gly Val Tyr Gly Phe Ala Lys Ser Leu
         35                  40                  45

Leu Lys Ala Leu Lys Glu Asp Gly Asp Val Val Ile Val Val Phe Asp
 50                  55                  60

Ala Lys Ala Pro Ser Phe Arg His Glu Ala Tyr Gly Ala Tyr Lys Ala
 65                  70                  75                  80

Gly Arg Ala Pro Thr Pro Glu Asp Phe Pro Arg Gln Leu Ala Leu Met
                 85                  90                  95

Lys Glu Leu Val Asp Leu Leu Gly Leu Glu Arg Leu Glu Val Pro Gly
             100                 105                 110

Phe Glu Ala Asp Asp Val Leu Ala Ala Leu Ala Lys Lys Ala Glu Arg
         115                 120                 125

Glu Gly Tyr Glu Val Arg Ile Leu Thr Ala Asp Arg Asp Leu Phe Gln
     130                 135                 140

Leu Leu Ser Asp Arg Ile Ala Val Leu His Pro Glu Gly His Leu Ile
145                 150                 155                 160

Thr Pro Gly Trp Leu Trp Glu Arg Tyr Gly Leu Arg Pro Glu Gln Trp
                 165                 170                 175

Val Asp Phe Arg Ala Leu Ala Gly Asp Pro Ser Asp Asn Ile Pro Gly
             180                 185                 190

Val Lys Gly Ile Gly Glu Lys Thr Ala Leu Lys Leu Leu Lys Glu Trp
         195                 200                 205

Gly Ser Leu Glu Asn Ile Gln Lys Asn Leu Asp Gln Val Ser Pro Pro
     210                 215                 220

Ser Val Arg Glu Lys Ile Gln Ala His Leu Asp Asp Leu Arg Leu Ser
225                 230                 235                 240

Gln Glu Leu Ser Arg Val Arg Thr Asp Leu Pro Leu Glu Val Asp Phe
                 245                 250                 255

Arg Arg Arg Arg Glu Pro Asp Arg Glu Gly Leu Arg Ala Phe Leu Glu
             260                 265                 270

Arg Leu Glu Phe Gly Ser Leu Leu His Glu Phe Gly Leu Leu Glu Ser
         275                 280                 285

Pro Gln Ala Ala Glu Glu Ala Pro Trp Pro Pro Glu Gly Ala Phe
     290                 295                 300

Leu Gly Phe Arg Leu Ser Arg Pro Glu Pro Met Trp Ala Glu Leu Leu
305                 310                 315                 320

Ser Leu Ala Ala Ser Ala Lys Gly Arg Val Tyr Arg Ala Glu Ala Pro
                 325                 330                 335

His Lys Ala Leu Ser Asp Leu Lys Glu Ile Arg Gly Leu Leu Ala Lys
             340                 345                 350

Asp Leu Ala Val Leu Ala Leu Arg Glu Gly Leu Gly Leu Pro Pro Thr
         355                 360                 365

Asp Asp Pro Met Leu Leu Ala Tyr Leu Leu Asp Pro Ser Asn Thr Thr
     370                 375                 380

Pro Glu Gly Val Ala Arg Arg Tyr Gly Gly Glu Trp Thr Glu Glu Ala
385                 390                 395                 400

Gly Glu Arg Ala Leu Leu Ala Glu Arg Leu Tyr Glu Asn Leu Leu Ser
                 405                 410                 415

Arg Leu Lys Gly Glu Glu Lys Leu Leu Trp Leu Tyr Glu Glu Val Glu
             420                 425                 430

Lys Pro Leu Ser Arg Val Leu Ala His Met Glu Ala Thr Gly Val Arg
         435                 440                 445
```

Leu Asp Val Pro Tyr Leu Arg Ala Leu Ser Leu Glu Val Ala Ala Glu
450                 455                 460

Met Gly Arg Leu Glu Glu Val Phe Arg Leu Ala Gly His Pro Phe
465                 470                 475                 480

Asn Leu Asn Ser Arg Asp Gln Leu Glu Arg Val Leu Phe Asp Glu Leu
                485                 490                 495

Gly Leu Pro Pro Ile Gly Lys Thr Glu Lys Thr Gly Lys Arg Ser Thr
            500                 505                 510

Ser Ala Ala Val Leu Glu Ala Leu Arg Glu Ala His Pro Ile Val Glu
        515                 520                 525

Lys Ile Leu Gln Tyr Arg Glu Leu Ala Lys Leu Lys Gly Thr Tyr Ile
530                 535                 540

Asp Pro Leu Pro Ala Leu Val His Pro Arg Thr Gly Arg Leu His Thr
545                 550                 555                 560

Arg Phe Asn Gln Thr Ala Thr Ala Thr Gly Arg Leu Ser Ser Ser Asp
                565                 570                 575

Pro Asn Leu Gln Asn Ile Pro Val Arg Thr Pro Leu Gly Gln Arg Ile
            580                 585                 590

Arg Arg Ala Phe Val Ala Glu Gly Tyr Leu Leu Val Ala Leu Asp
        595                 600                 605

Tyr Ser Gln Ile Glu Leu Arg Val Leu Ala His Leu Ser Gly Asp Glu
610                 615                 620

Asn Leu Ile Arg Val Phe Gln Glu Gly Arg Asp Ile His Thr Gln Thr
625                 630                 635                 640

Ala Ser Trp Met Phe Gly Leu Pro Ala Glu Ala Ile Asp Pro Leu Arg
                645                 650                 655

Arg Arg Ala Ala Lys Thr Ile Asn Phe Gly Val Leu Tyr Gly Met Ser
            660                 665                 670

Ala His Arg Leu Ser Gln Glu Leu Gly Ile Pro Tyr Glu Glu Ala Val
        675                 680                 685

Ala Phe Ile Asp Arg Tyr Phe Gln Ser Tyr Pro Lys Val Lys Ala Trp
690                 695                 700

Ile Glu Arg Thr Leu Glu Glu Gly Arg Gln Arg Gly Tyr Val Glu Thr
705                 710                 715                 720

Leu Phe Gly Arg Arg Tyr Val Pro Asp Leu Asn Ala Arg Val Lys
                725                 730                 735

Ser Val Arg Glu Ala Ala Glu Arg Met Ala Phe Asn Met Pro Val Gln
            740                 745                 750

Gly Thr Ala Ala Asp Leu Met Lys Leu Ala Met Val Arg Leu Phe Pro
        755                 760                 765

Arg Leu Pro Glu Val Gly Ala Arg Met Leu Leu Gln Val His Asp Glu
770                 775                 780

Leu Leu Leu Glu Ala Pro Lys Glu Arg Ala Glu Ala Ala Ala Leu
                785                 790                 795                 800

Ala Lys Glu Val Met Glu Gly Val Trp Pro Leu Ala Val Pro Leu Glu
            805                 810                 815

Val Glu Val Gly Ile Gly Glu Asp Trp Leu Ser Ala Lys Gly
        820                 825                 830

<210> SEQ ID NO 11
<211> LENGTH: 830
<212> TYPE: PRT
<213> ORGANISM: Thermus brockianus

<400> SEQUENCE: 11

```
Met Leu Pro Leu Phe Glu Pro Lys Gly Arg Val Leu Leu Val Asp Gly
1               5                   10                  15

His His Leu Ala Tyr Arg Asn Phe Phe Ala Leu Lys Gly Leu Thr Thr
            20                  25                  30

Ser Arg Gly Glu Pro Val Gln Gly Val Tyr Asp Phe Ala Lys Ser Leu
            35                  40                  45

Leu Lys Ala Leu Lys Glu Asp Gly Asp Val Val Ile Val Val Phe Asp
50                  55                  60

Ala Lys Ala Pro Ser Phe Arg His Glu Ala Tyr Gly Ala Tyr Lys Ala
65                  70                  75                  80

Gly Arg Ala Pro Thr Pro Glu Asp Phe Pro Arg Gln Leu Ala Leu Met
                85                  90                  95

Lys Glu Leu Val Asp Leu Leu Gly Leu Glu Arg Leu Glu Val Pro Gly
                100                 105                 110

Phe Glu Ala Asp Asp Val Leu Ala Ala Leu Ala Lys Lys Ala Glu Arg
                115                 120                 125

Glu Gly Tyr Glu Val Arg Ile Leu Thr Ala Asp Arg Asp Leu Phe Gln
            130                 135                 140

Leu Leu Ser Asp Arg Ile Ala Val Leu His Pro Glu Gly His Leu Ile
145                 150                 155                 160

Thr Pro Gly Trp Leu Trp Glu Arg Tyr Gly Leu Arg Pro Glu Gln Trp
                165                 170                 175

Val Asp Phe Arg Ala Leu Ala Gly Asp Pro Ser Asp Asn Ile Pro Gly
                180                 185                 190

Val Lys Gly Ile Gly Glu Lys Thr Ala Leu Lys Leu Leu Lys Glu Trp
            195                 200                 205

Gly Ser Leu Glu Asn Ile Gln Lys Asn Leu Asp Gln Val Ser Pro Pro
            210                 215                 220

Ser Val Arg Glu Lys Ile Gln Ala His Leu Asp Asp Leu Arg Leu Ser
225                 230                 235                 240

Gln Glu Leu Ser Arg Val Arg Thr Asp Leu Pro Leu Glu Val Asp Phe
                245                 250                 255

Arg Arg Arg Arg Glu Pro Asp Arg Glu Gly Leu Arg Ala Phe Leu Glu
                260                 265                 270

Arg Leu Glu Phe Gly Ser Leu Leu His Glu Phe Gly Leu Leu Glu Ser
            275                 280                 285

Pro Gln Ala Ala Glu Glu Ala Pro Trp Pro Pro Glu Gly Ala Phe
            290                 295                 300

Leu Gly Phe Arg Leu Ser Arg Pro Glu Pro Met Trp Ala Glu Leu Leu
305                 310                 315                 320

Ser Leu Ala Ala Ser Ala Lys Gly Arg Val Tyr Arg Ala Glu Ala Pro
                325                 330                 335

His Lys Ala Leu Ser Asp Leu Lys Glu Ile Arg Gly Leu Leu Ala Lys
            340                 345                 350

Asp Leu Ala Val Leu Ala Leu Arg Glu Gly Leu Gly Leu Pro Pro Thr
            355                 360                 365

Asp Asp Pro Met Leu Leu Ala Tyr Leu Leu Asp Pro Ser Asn Thr Thr
370                 375                 380

Pro Glu Gly Val Ala Arg Arg Tyr Gly Gly Glu Trp Thr Glu Glu Ala
385                 390                 395                 400

Gly Glu Arg Ala Leu Leu Ala Glu Arg Leu Tyr Glu Asn Leu Leu Ser
                405                 410                 415

Arg Leu Lys Gly Glu Glu Lys Leu Leu Trp Leu Tyr Glu Glu Val Glu
```

```
                    420             425             430
Lys Pro Leu Ser Arg Val Leu Ala His Met Glu Ala Thr Gly Val Arg
        435                 440                 445
Leu Asp Val Pro Tyr Leu Arg Ala Leu Ser Leu Glu Val Ala Ala Glu
        450                 455                 460
Met Gly Arg Leu Glu Glu Val Phe Arg Leu Ala Gly His Pro Phe
465                 470                 475                 480
Asn Leu Asn Ser Arg Asp Gln Leu Glu Arg Val Leu Phe Asp Glu Leu
                485                 490                 495
Gly Leu Pro Pro Ile Gly Lys Thr Glu Lys Thr Gly Lys Arg Ser Thr
                500                 505                 510
Ser Ala Ala Val Leu Glu Ala Leu Arg Glu Ala His Pro Ile Val Glu
                515                 520                 525
Lys Ile Leu Gln Tyr Arg Glu Leu Ala Lys Leu Lys Gly Thr Tyr Ile
                530                 535                 540
Asp Leu Leu Pro Ala Leu Val His Pro Arg Thr Gly Arg Leu His Thr
545                 550                 555                 560
Arg Phe Asn Gln Thr Ala Thr Ala Thr Gly Arg Leu Ser Ser Ser Asp
                565                 570                 575
Pro Asn Leu Gln Asn Ile Pro Val Arg Thr Pro Leu Gly Gln Arg Ile
                580                 585                 590
Arg Arg Ala Phe Val Ala Glu Gly Tyr Leu Leu Val Ala Leu Asp
                595                 600                 605
Tyr Ser Gln Ile Glu Leu Arg Val Leu Ala His Leu Ser Gly Asp Glu
                610                 615                 620
Asn Leu Ile Arg Val Phe Gln Glu Gly Arg Asp Ile His Thr Gln Thr
625                 630                 635                 640
Ala Ser Trp Met Phe Gly Leu Pro Ala Glu Ala Ile Asp Pro Leu Arg
                645                 650                 655
Arg Arg Ala Ala Lys Thr Ile Asn Phe Gly Val Leu Tyr Gly Met Ser
                660                 665                 670
Ala His Arg Leu Ser Gln Glu Leu Gly Ile Pro Tyr Glu Glu Ala Val
                675                 680                 685
Ala Phe Ile Asp Arg Tyr Phe Gln Ser Tyr Pro Lys Val Lys Ala Trp
                690                 695                 700
Ile Glu Arg Thr Leu Glu Glu Gly Arg Gln Arg Gly Tyr Val Glu Thr
705                 710                 715                 720
Leu Phe Gly Arg Arg Arg Tyr Val Pro Asp Leu Asn Ala Arg Val Lys
                725                 730                 735
Ser Val Arg Glu Ala Ala Glu Arg Met Ala Phe Asn Met Pro Val Gln
                740                 745                 750
Gly Thr Ala Ala Asp Leu Met Lys Leu Ala Met Val Arg Leu Phe Pro
                755                 760                 765
Arg Leu Pro Glu Val Gly Ala Arg Met Leu Leu Gln Val His Asp Glu
                770                 775                 780
Leu Leu Leu Glu Ala Pro Lys Glu Arg Ala Glu Glu Ala Ala Ala Leu
785                 790                 795                 800
Ala Lys Glu Val Met Glu Gly Val Trp Pro Leu Ala Val Pro Leu Glu
                805                 810                 815
Val Glu Val Gly Ile Gly Glu Asp Trp Leu Ser Ala Lys Gly
                820                 825                 830

<210> SEQ ID NO 12
<211> LENGTH: 830
```

<212> TYPE: PRT
<213> ORGANISM: Thermus brockianus

<400> SEQUENCE: 12

```
Met Leu Pro Leu Phe Glu Pro Lys Gly Arg Val Leu Val Asp Gly
1               5                   10                  15

His His Leu Ala Tyr Arg Asn Phe Phe Ala Leu Lys Gly Leu Thr Thr
            20                  25                  30

Ser Arg Gly Glu Pro Val Gln Gly Val Tyr Asp Phe Ala Lys Ser Leu
        35                  40                  45

Leu Lys Ala Leu Lys Glu Asp Gly Asp Val Val Ile Val Val Phe Asp
    50                  55                  60

Ala Lys Ala Pro Ser Phe Arg His Glu Ala Tyr Gly Ala Tyr Lys Ala
65              70                  75                  80

Gly Arg Ala Pro Thr Pro Glu Asp Phe Pro Arg Gln Leu Ala Leu Met
                85                  90                  95

Lys Glu Leu Val Asp Leu Leu Gly Leu Glu Arg Leu Glu Val Pro Gly
            100                 105                 110

Phe Glu Ala Asp Asp Val Leu Ala Ala Leu Ala Lys Lys Ala Glu Arg
        115                 120                 125

Glu Gly Tyr Glu Val Arg Ile Leu Thr Ala Asp Arg Asp Leu Phe Gln
    130                 135                 140

Leu Leu Ser Asp Arg Ile Ala Val Leu His Pro Glu Gly His Leu Ile
145                 150                 155                 160

Thr Pro Gly Trp Leu Trp Glu Arg Tyr Gly Leu Arg Pro Glu Gln Trp
                165                 170                 175

Val Asp Phe Arg Ala Leu Ala Gly Asp Pro Ser Asp Asn Ile Pro Gly
            180                 185                 190

Val Lys Gly Ile Gly Glu Lys Thr Ala Leu Lys Leu Leu Lys Glu Trp
        195                 200                 205

Gly Ser Leu Glu Asn Ile Gln Lys Asn Leu Asp Gln Val Ser Pro Pro
    210                 215                 220

Ser Val Arg Glu Lys Ile Gln Ala His Leu Asp Asp Leu Arg Leu Ser
225                 230                 235                 240

Gln Glu Leu Ser Arg Val Arg Thr Asp Leu Pro Leu Glu Val Asp Phe
                245                 250                 255

Arg Arg Arg Arg Glu Pro Asp Arg Glu Gly Leu Arg Ala Phe Leu Glu
            260                 265                 270

Arg Leu Glu Phe Gly Ser Leu Leu His Glu Phe Gly Leu Leu Glu Ser
        275                 280                 285

Pro Gln Ala Ala Glu Glu Ala Pro Trp Pro Pro Glu Gly Ala Phe
    290                 295                 300

Leu Gly Phe Arg Leu Ser Arg Pro Glu Pro Met Trp Ala Glu Leu Leu
305                 310                 315                 320

Ser Leu Ala Ala Ser Ala Lys Gly Arg Val Tyr Arg Ala Glu Ala Pro
                325                 330                 335

His Lys Ala Leu Ser Asp Leu Lys Glu Ile Arg Gly Leu Leu Ala Lys
            340                 345                 350

Asp Leu Ala Val Leu Ala Leu Arg Glu Gly Leu Gly Leu Pro Pro Thr
        355                 360                 365

Asp Asp Pro Met Leu Leu Ala Tyr Leu Leu Asp Pro Ser Asn Thr Thr
    370                 375                 380

Pro Glu Gly Val Ala Arg Arg Tyr Gly Gly Glu Trp Thr Glu Glu Ala
385                 390                 395                 400
```

```
Gly Glu Arg Ala Leu Leu Ala Glu Arg Leu Tyr Glu Asn Leu Leu Ser
            405                 410                 415

Arg Leu Lys Gly Glu Lys Leu Leu Trp Leu Tyr Glu Glu Val Glu
        420                 425                 430

Lys Pro Leu Ser Arg Val Leu Ala His Met Glu Ala Thr Gly Val Arg
            435                 440                 445

Leu Asp Val Pro Tyr Leu Arg Ala Leu Ser Leu Glu Val Ala Ala Glu
        450                 455                 460

Met Gly Arg Leu Glu Glu Val Phe Arg Leu Ala Gly His Pro Phe
465                 470                 475                 480

Asn Leu Asn Ser Arg Asp Gln Leu Glu Arg Val Leu Phe Asp Glu Leu
            485                 490                 495

Gly Leu Pro Pro Ile Gly Lys Thr Glu Lys Thr Gly Lys Arg Ser Thr
        500                 505                 510

Ser Ala Ala Val Leu Glu Ala Leu Arg Glu Ala His Pro Ile Val Glu
        515                 520                 525

Lys Ile Leu Gln Tyr Arg Glu Leu Ala Lys Leu Lys Gly Thr Tyr Ile
        530                 535                 540

Asp Pro Leu Pro Ala Leu Val His Pro Arg Thr Gly Arg Leu His Thr
545                 550                 555                 560

Arg Phe Asn Gln Thr Ala Thr Ala Thr Gly Arg Leu Ser Ser Ser Asp
            565                 570                 575

Pro Asn Leu Gln Asn Ile Pro Val Arg Thr Pro Leu Gly Gln Arg Ile
        580                 585                 590

Arg Arg Ala Phe Val Ala Glu Glu Gly Tyr Leu Leu Val Ala Leu Asp
        595                 600                 605

Tyr Ser Gln Ile Glu Leu Arg Val Leu Ala His Leu Ser Gly Asp Glu
        610                 615                 620

Asn Leu Ile Arg Val Phe Gln Glu Gly Arg Asp Ile His Thr Gln Thr
625                 630                 635                 640

Ala Ser Trp Met Phe Gly Leu Pro Ala Glu Ala Ile Asp Pro Leu Arg
            645                 650                 655

Arg Arg Ala Ala Lys Thr Ile Asn Phe Gly Val Leu Tyr Gly Met Ser
        660                 665                 670

Ala His Arg Leu Ser Gln Glu Leu Gly Ile Pro Tyr Glu Glu Ala Val
        675                 680                 685

Ala Phe Ile Asp Arg Tyr Phe Gln Ser Tyr Pro Lys Val Lys Ala Trp
        690                 695                 700

Ile Glu Arg Thr Leu Glu Glu Gly Arg Gln Arg Gly Tyr Val Glu Thr
705                 710                 715                 720

Leu Phe Gly Arg Arg Arg Tyr Val Pro Asp Leu Asn Ala Arg Val Lys
            725                 730                 735

Ser Val Arg Glu Ala Ala Glu Arg Met Ala Phe Asn Met Pro Val Gln
        740                 745                 750

Gly Thr Ala Ala Asp Leu Met Lys Leu Ala Met Val Arg Leu Phe Pro
        755                 760                 765

Arg Leu Pro Glu Val Gly Ala Arg Met Leu Leu Gln Val His Asp Glu
        770                 775                 780

Leu Leu Leu Glu Ala Pro Lys Glu Arg Ala Glu Glu Ala Ala Ala Leu
785                 790                 795                 800

Ala Lys Glu Val Met Glu Gly Val Trp Pro Leu Ala Val Pro Leu Glu
            805                 810                 815

Val Glu Val Gly Ile Gly Glu Asp Trp Leu Ser Ala Lys Gly
        820                 825                 830
```

<210> SEQ ID NO 13
<211> LENGTH: 830
<212> TYPE: PRT
<213> ORGANISM: Thermus brockianus

<400> SEQUENCE: 13

```
Met Leu Pro Leu Phe Glu Pro Lys Gly Arg Val Leu Val Asp Gly
1               5                   10                  15

His His Leu Ala Tyr Arg Asn Phe Phe Ala Leu Lys Gly Leu Thr Thr
                20                  25                  30

Ser Arg Gly Glu Pro Val Gln Gly Val Tyr Gly Phe Ala Lys Ser Leu
            35                  40                  45

Leu Lys Ala Leu Lys Glu Asp Gly Asp Val Val Ile Val Val Phe Asp
        50                  55                  60

Ala Lys Ala Pro Ser Phe Arg His Glu Ala Tyr Gly Ala Tyr Lys Ala
65                  70                  75                  80

Gly Arg Ala Pro Thr Pro Glu Asp Phe Pro Arg Gln Leu Ala Leu Met
                85                  90                  95

Lys Glu Leu Val Asp Leu Leu Gly Leu Glu Arg Leu Glu Val Pro Gly
            100                 105                 110

Phe Glu Ala Asp Asp Val Leu Ala Ala Leu Ala Lys Lys Ala Glu Arg
        115                 120                 125

Glu Gly Tyr Glu Val Arg Ile Leu Thr Ala Asp Arg Asp Leu Phe Gln
    130                 135                 140

Leu Leu Ser Asp Arg Ile Ala Val Leu His Pro Glu Gly His Leu Ile
145                 150                 155                 160

Thr Pro Gly Trp Leu Trp Glu Arg Tyr Gly Leu Arg Pro Glu Gln Trp
                165                 170                 175

Val Asp Phe Arg Ala Leu Ala Gly Asp Pro Ser Asp Asn Ile Pro Gly
            180                 185                 190

Val Lys Gly Ile Gly Glu Lys Thr Ala Leu Lys Leu Leu Lys Glu Trp
        195                 200                 205

Gly Ser Leu Glu Asn Ile Gln Lys Asn Leu Asp Gln Val Ser Pro Pro
    210                 215                 220

Ser Val Arg Glu Lys Ile Gln Ala His Leu Asp Asp Leu Arg Leu Ser
225                 230                 235                 240

Gln Glu Leu Ser Arg Val Arg Thr Asp Leu Pro Leu Glu Val Asp Phe
                245                 250                 255

Arg Arg Arg Arg Glu Pro Asp Arg Glu Gly Leu Arg Ala Phe Leu Glu
            260                 265                 270

Arg Leu Glu Phe Gly Ser Leu Leu His Glu Phe Gly Leu Leu Glu Ser
        275                 280                 285

Pro Gln Ala Ala Glu Glu Ala Pro Trp Pro Pro Glu Gly Ala Phe
    290                 295                 300

Leu Gly Phe Arg Leu Ser Arg Pro Glu Pro Met Trp Ala Glu Leu Leu
305                 310                 315                 320

Ser Leu Ala Ala Ser Ala Lys Gly Arg Val Tyr Arg Ala Glu Ala Pro
                325                 330                 335

His Lys Ala Leu Ser Asp Leu Lys Glu Ile Arg Gly Leu Leu Ala Lys
            340                 345                 350

Asp Leu Ala Val Leu Ala Leu Arg Glu Gly Leu Gly Leu Pro Pro Thr
        355                 360                 365

Asp Asp Pro Met Leu Leu Ala Tyr Leu Leu Asp Pro Ser Asn Thr Thr
    370                 375                 380
```

-continued

```
Pro Glu Gly Val Ala Arg Arg Tyr Gly Gly Glu Trp Thr Glu Glu Ala
385                 390                 395                 400

Gly Glu Arg Ala Leu Leu Ala Glu Arg Leu Tyr Glu Asn Leu Leu Ser
            405                 410                 415

Arg Leu Lys Gly Glu Glu Lys Leu Leu Trp Leu Tyr Glu Val Glu
        420                 425                 430

Lys Pro Leu Ser Arg Val Leu Ala His Met Glu Ala Thr Gly Val Arg
            435                 440                 445

Leu Asp Val Pro Tyr Leu Arg Ala Leu Ser Leu Glu Val Ala Ala Glu
        450                 455                 460

Met Gly Arg Leu Glu Glu Val Phe Arg Leu Ala Gly His Pro Phe
465                 470                 475                 480

Asn Leu Asn Ser Arg Asp Gln Leu Glu Arg Val Leu Phe Asp Glu Leu
            485                 490                 495

Gly Leu Pro Pro Ile Gly Lys Thr Glu Lys Thr Gly Lys Arg Ser Thr
            500                 505                 510

Ser Ala Ala Val Leu Glu Ala Leu Arg Glu Ala His Pro Ile Val Glu
            515                 520                 525

Lys Ile Leu Gln Tyr Arg Glu Leu Ala Lys Leu Lys Gly Thr Tyr Ile
530                 535                 540

Asp Leu Leu Pro Ala Leu Val His Pro Arg Thr Gly Arg Leu His Thr
545                 550                 555                 560

Arg Phe Asn Gln Thr Ala Thr Ala Thr Gly Arg Leu Ser Ser Ser Asp
                565                 570                 575

Pro Asn Leu Gln Asn Ile Pro Val Arg Thr Pro Leu Gly Gln Arg Ile
            580                 585                 590

Arg Arg Ala Phe Val Ala Glu Glu Gly Tyr Leu Leu Val Ala Leu Asp
        595                 600                 605

Tyr Ser Gln Ile Glu Leu Arg Val Leu Ala His Leu Ser Gly Asp Glu
610                 615                 620

Asn Leu Ile Arg Val Phe Gln Glu Gly Arg Asp Ile His Thr Gln Thr
625                 630                 635                 640

Ala Ser Trp Met Phe Gly Leu Pro Ala Glu Ala Ile Asp Pro Leu Arg
                645                 650                 655

Arg Arg Ala Ala Lys Thr Ile Asn Tyr Gly Val Leu Tyr Gly Met Ser
            660                 665                 670

Ala His Arg Leu Ser Gln Glu Leu Gly Ile Pro Tyr Glu Glu Ala Val
        675                 680                 685

Ala Phe Ile Asp Arg Tyr Phe Gln Ser Tyr Pro Lys Val Lys Ala Trp
690                 695                 700

Ile Glu Arg Thr Leu Glu Glu Gly Arg Gln Arg Gly Tyr Val Glu Thr
705                 710                 715                 720

Leu Phe Gly Arg Arg Arg Tyr Val Pro Asp Leu Asn Ala Arg Val Lys
            725                 730                 735

Ser Val Arg Glu Ala Ala Glu Arg Met Ala Phe Asn Met Pro Val Gln
            740                 745                 750

Gly Thr Ala Ala Asp Leu Met Lys Leu Ala Met Val Arg Leu Phe Pro
            755                 760                 765

Arg Leu Pro Glu Val Gly Ala Arg Met Leu Leu Gln Val His Asp Glu
        770                 775                 780

Leu Leu Leu Glu Ala Pro Lys Glu Arg Ala Glu Glu Ala Ala Ala Leu
785                 790                 795                 800

Ala Lys Glu Val Met Glu Gly Val Trp Pro Leu Ala Val Pro Leu Glu
```

```
                    805                 810                 815
Val Glu Val Gly Ile Gly Glu Asp Trp Leu Ser Ala Lys Gly
            820                 825                 830

<210> SEQ ID NO 14
<211> LENGTH: 830
<212> TYPE: PRT
<213> ORGANISM: Thermus brockianus

<400> SEQUENCE: 14

Met Leu Pro Leu Phe Glu Pro Lys Gly Arg Val Leu Val Asp Gly
1               5                   10                  15

His His Leu Ala Tyr Arg Asn Phe Phe Ala Leu Lys Gly Leu Thr Thr
                20                  25                  30

Ser Arg Gly Glu Pro Val Gln Gly Val Tyr Gly Phe Ala Lys Ser Leu
            35                  40                  45

Leu Lys Ala Leu Lys Glu Asp Gly Asp Val Val Ile Val Val Phe Asp
50                  55                  60

Ala Lys Ala Pro Ser Phe Arg His Glu Ala Tyr Gly Ala Tyr Lys Ala
65                  70                  75                  80

Gly Arg Ala Pro Thr Pro Glu Asp Phe Pro Arg Gln Leu Ala Leu Met
                85                  90                  95

Lys Glu Leu Val Asp Leu Leu Gly Leu Glu Arg Leu Glu Val Pro Gly
            100                 105                 110

Phe Glu Ala Asp Asp Val Leu Ala Ala Leu Ala Lys Lys Ala Glu Arg
        115                 120                 125

Glu Gly Tyr Glu Val Arg Ile Leu Thr Ala Asp Arg Asp Leu Phe Gln
    130                 135                 140

Leu Leu Ser Asp Arg Ile Ala Val Leu His Pro Glu Gly His Leu Ile
145                 150                 155                 160

Thr Pro Gly Trp Leu Trp Glu Arg Tyr Gly Leu Arg Pro Glu Gln Trp
                165                 170                 175

Val Asp Phe Arg Ala Leu Ala Gly Asp Pro Ser Asp Asn Ile Pro Gly
            180                 185                 190

Val Lys Gly Ile Gly Glu Lys Thr Ala Leu Lys Leu Leu Lys Glu Trp
        195                 200                 205

Gly Ser Leu Glu Asn Ile Gln Lys Asn Leu Asp Gln Val Ser Pro Pro
    210                 215                 220

Ser Val Arg Glu Lys Ile Gln Ala His Leu Asp Asp Leu Arg Leu Ser
225                 230                 235                 240

Gln Glu Leu Ser Arg Val Arg Thr Asp Leu Pro Leu Glu Val Asp Phe
                245                 250                 255

Arg Arg Arg Arg Glu Pro Asp Arg Glu Gly Leu Arg Ala Phe Leu Glu
            260                 265                 270

Arg Leu Glu Phe Gly Ser Leu Leu His Glu Phe Gly Leu Leu Glu Ser
        275                 280                 285

Pro Gln Ala Ala Glu Glu Ala Pro Trp Pro Pro Glu Gly Ala Phe
    290                 295                 300

Leu Gly Phe Arg Leu Ser Arg Pro Glu Pro Met Trp Ala Glu Leu Leu
305                 310                 315                 320

Ser Leu Ala Ala Ser Ala Lys Gly Arg Val Tyr Arg Ala Glu Ala Pro
                325                 330                 335

His Lys Ala Leu Ser Asp Leu Lys Glu Ile Arg Gly Leu Leu Ala Lys
            340                 345                 350

Asp Leu Ala Val Leu Ala Leu Arg Glu Gly Leu Gly Leu Pro Pro Thr
```

```
                355                 360                 365
Asp Asp Pro Met Leu Leu Ala Tyr Leu Leu Asp Pro Ser Asn Thr Thr
    370                 375                 380
Pro Glu Gly Val Ala Arg Arg Tyr Gly Gly Glu Trp Thr Glu Glu Ala
385                 390                 395                 400
Gly Glu Arg Ala Leu Leu Ala Glu Arg Leu Tyr Glu Asn Leu Leu Ser
                405                 410                 415
Arg Leu Lys Gly Glu Glu Lys Leu Leu Trp Leu Tyr Glu Glu Val Glu
                420                 425                 430
Lys Pro Leu Ser Arg Val Leu Ala His Met Glu Ala Thr Gly Val Arg
                435                 440                 445
Leu Asp Val Pro Tyr Leu Arg Ala Leu Ser Leu Glu Val Ala Ala Glu
    450                 455                 460
Met Gly Arg Leu Glu Glu Glu Val Phe Arg Leu Ala Gly His Pro Phe
465                 470                 475                 480
Asn Leu Asn Ser Arg Asp Gln Leu Glu Arg Val Leu Phe Asp Glu Leu
                485                 490                 495
Gly Leu Pro Pro Ile Gly Lys Thr Glu Lys Thr Gly Lys Arg Ser Thr
                500                 505                 510
Ser Ala Ala Val Leu Glu Ala Leu Arg Glu Ala His Pro Ile Val Glu
                515                 520                 525
Lys Ile Leu Gln Tyr Arg Glu Leu Ala Lys Leu Lys Gly Thr Tyr Ile
    530                 535                 540
Asp Pro Leu Pro Ala Leu Val His Pro Arg Thr Gly Arg Leu His Thr
545                 550                 555                 560
Arg Phe Asn Gln Thr Ala Thr Ala Thr Gly Arg Leu Ser Ser Ser Asp
                565                 570                 575
Pro Asn Leu Gln Asn Ile Pro Val Arg Thr Pro Leu Gly Gln Arg Ile
                580                 585                 590
Arg Arg Ala Phe Val Ala Glu Glu Gly Tyr Leu Leu Val Ala Leu Asp
                595                 600                 605
Tyr Ser Gln Ile Glu Leu Arg Val Leu Ala His Leu Ser Gly Asp Glu
    610                 615                 620
Asn Leu Ile Arg Val Phe Gln Glu Gly Arg Asp Ile His Thr Gln Thr
625                 630                 635                 640
Ala Ser Trp Met Phe Gly Leu Pro Ala Glu Ala Ile Asp Pro Leu Arg
                645                 650                 655
Arg Arg Ala Ala Lys Thr Ile Asn Tyr Gly Val Leu Tyr Gly Met Ser
                660                 665                 670
Ala His Arg Leu Ser Gln Glu Leu Gly Ile Pro Tyr Glu Glu Ala Val
                675                 680                 685
Ala Phe Ile Asp Arg Tyr Phe Gln Ser Tyr Pro Lys Val Lys Ala Trp
    690                 695                 700
Ile Glu Arg Thr Leu Glu Glu Gly Arg Gln Arg Gly Tyr Val Glu Thr
705                 710                 715                 720
Leu Phe Gly Arg Arg Arg Tyr Val Pro Asp Leu Asn Ala Arg Val Lys
                725                 730                 735
Ser Val Arg Glu Ala Ala Glu Arg Met Ala Phe Asn Met Pro Val Gln
                740                 745                 750
Gly Thr Ala Ala Asp Leu Met Lys Leu Ala Met Val Arg Leu Phe Pro
                755                 760                 765
Arg Leu Pro Glu Val Gly Ala Arg Met Leu Leu Gln Val His Asp Glu
    770                 775                 780
```

```
Leu Leu Leu Glu Ala Pro Lys Glu Arg Ala Glu Ala Ala Ala Leu
785                 790                 795                 800

Ala Lys Glu Val Met Glu Gly Val Trp Pro Leu Ala Val Pro Leu Glu
            805                 810                 815

Val Glu Val Gly Ile Gly Glu Asp Trp Leu Ser Ala Lys Gly
        820                 825                 830

<210> SEQ ID NO 15
<211> LENGTH: 830
<212> TYPE: PRT
<213> ORGANISM: Thermus brockianus

<400> SEQUENCE: 15

Met Leu Pro Leu Phe Glu Pro Lys Gly Arg Val Leu Leu Val Asp Gly
1               5                   10                  15

His His Leu Ala Tyr Arg Asn Phe Phe Ala Leu Lys Gly Leu Thr Thr
            20                  25                  30

Ser Arg Gly Glu Pro Val Gln Gly Val Tyr Asp Phe Ala Lys Ser Leu
        35                  40                  45

Leu Lys Ala Leu Lys Glu Asp Gly Asp Val Val Ile Val Val Phe Asp
    50                  55                  60

Ala Lys Ala Pro Ser Phe Arg His Glu Ala Tyr Gly Ala Tyr Lys Ala
65                  70                  75                  80

Gly Arg Ala Pro Thr Pro Glu Asp Phe Pro Arg Gln Leu Ala Leu Met
                85                  90                  95

Lys Glu Leu Val Asp Leu Leu Gly Leu Glu Arg Leu Glu Val Pro Gly
            100                 105                 110

Phe Glu Ala Asp Asp Val Leu Ala Ala Leu Ala Lys Lys Ala Glu Arg
        115                 120                 125

Glu Gly Tyr Glu Val Arg Ile Leu Thr Ala Asp Arg Asp Leu Phe Gln
    130                 135                 140

Leu Leu Ser Asp Arg Ile Ala Val Leu His Pro Glu Gly His Leu Ile
145                 150                 155                 160

Thr Pro Gly Trp Leu Trp Glu Arg Tyr Gly Leu Arg Pro Glu Gln Trp
                165                 170                 175

Val Asp Phe Arg Ala Leu Ala Gly Asp Pro Ser Asp Asn Ile Pro Gly
            180                 185                 190

Val Lys Gly Ile Gly Glu Lys Thr Ala Leu Lys Leu Leu Lys Glu Trp
        195                 200                 205

Gly Ser Leu Glu Asn Ile Gln Lys Asn Leu Asp Gln Val Ser Pro Pro
    210                 215                 220

Ser Val Arg Glu Lys Ile Gln Ala His Leu Asp Asp Leu Arg Leu Ser
225                 230                 235                 240

Gln Glu Leu Ser Arg Val Arg Thr Asp Leu Pro Leu Glu Val Asp Phe
                245                 250                 255

Arg Arg Arg Arg Glu Pro Asp Arg Glu Gly Leu Arg Ala Phe Leu Glu
            260                 265                 270

Arg Leu Glu Phe Gly Ser Leu Leu His Glu Phe Gly Leu Leu Glu Ser
        275                 280                 285

Pro Gln Ala Ala Glu Glu Ala Pro Trp Pro Pro Glu Gly Ala Phe
    290                 295                 300

Leu Gly Phe Arg Leu Ser Arg Pro Glu Pro Met Trp Ala Glu Leu Leu
305                 310                 315                 320

Ser Leu Ala Ala Ser Ala Lys Gly Arg Val Tyr Arg Ala Glu Ala Pro
                325                 330                 335
```

```
His Lys Ala Leu Ser Asp Leu Lys Glu Ile Arg Gly Leu Leu Ala Lys
            340                 345                 350

Asp Leu Ala Val Leu Ala Leu Arg Glu Gly Leu Gly Leu Pro Pro Thr
            355                 360                 365

Asp Asp Pro Met Leu Leu Ala Tyr Leu Leu Asp Pro Ser Asn Thr Thr
            370                 375                 380

Pro Glu Gly Val Ala Arg Arg Tyr Gly Gly Glu Trp Thr Glu Glu Ala
385                 390                 395                 400

Gly Glu Arg Ala Leu Leu Ala Glu Arg Leu Tyr Glu Asn Leu Leu Ser
                405                 410                 415

Arg Leu Lys Gly Glu Glu Lys Leu Leu Trp Leu Tyr Glu Glu Val Glu
            420                 425                 430

Lys Pro Leu Ser Arg Val Leu Ala His Met Glu Ala Thr Gly Val Arg
            435                 440                 445

Leu Asp Val Pro Tyr Leu Arg Ala Leu Ser Leu Glu Val Ala Ala Glu
            450                 455                 460

Met Gly Arg Leu Glu Glu Val Phe Arg Leu Ala Gly His Pro Phe
465                 470                 475                 480

Asn Leu Asn Ser Arg Asp Gln Leu Glu Arg Val Leu Phe Asp Glu Leu
                485                 490                 495

Gly Leu Pro Pro Ile Gly Lys Thr Glu Lys Thr Gly Lys Arg Ser Thr
            500                 505                 510

Ser Ala Ala Val Leu Glu Ala Leu Arg Glu Ala His Pro Ile Val Glu
            515                 520                 525

Lys Ile Leu Gln Tyr Arg Glu Leu Ala Lys Leu Lys Gly Thr Tyr Ile
530                 535                 540

Asp Leu Leu Pro Ala Leu Val His Pro Arg Thr Gly Arg Leu His Thr
545                 550                 555                 560

Arg Phe Asn Gln Thr Ala Thr Ala Thr Gly Arg Leu Ser Ser Ser Asp
                565                 570                 575

Pro Asn Leu Gln Asn Ile Pro Val Arg Thr Pro Leu Gly Gln Arg Ile
            580                 585                 590

Arg Arg Ala Phe Val Ala Glu Glu Gly Tyr Leu Leu Val Ala Leu Asp
            595                 600                 605

Tyr Ser Gln Ile Glu Leu Arg Val Leu Ala His Leu Ser Gly Asp Glu
            610                 615                 620

Asn Leu Ile Arg Val Phe Gln Glu Gly Arg Asp Ile His Thr Gln Thr
625                 630                 635                 640

Ala Ser Trp Met Phe Gly Leu Pro Ala Glu Ala Ile Asp Pro Leu Arg
                645                 650                 655

Arg Arg Ala Ala Lys Thr Ile Asn Tyr Gly Val Leu Tyr Gly Met Ser
            660                 665                 670

Ala His Arg Leu Ser Gln Glu Leu Gly Ile Pro Tyr Glu Glu Ala Val
            675                 680                 685

Ala Phe Ile Asp Arg Tyr Phe Gln Ser Tyr Pro Lys Val Lys Ala Trp
            690                 695                 700

Ile Glu Arg Thr Leu Glu Glu Gly Arg Gln Arg Gly Tyr Val Glu Thr
705                 710                 715                 720

Leu Phe Gly Arg Arg Arg Tyr Val Pro Asp Leu Asn Ala Arg Val Lys
                725                 730                 735

Ser Val Arg Glu Ala Ala Glu Arg Met Ala Phe Asn Met Pro Val Gln
            740                 745                 750

Gly Thr Ala Ala Asp Leu Met Lys Leu Ala Met Val Arg Leu Phe Pro
            755                 760                 765
```

```
Arg Leu Pro Glu Val Gly Ala Arg Met Leu Leu Gln Val His Asp Glu
    770             775                 780

Leu Leu Leu Glu Ala Pro Lys Glu Arg Ala Glu Ala Ala Ala Leu
785             790                 795                 800

Ala Lys Glu Val Met Glu Val Trp Pro Leu Ala Val Pro Leu Glu
                805             810                 815

Val Glu Val Gly Ile Gly Glu Asp Trp Leu Ser Ala Lys Gly
        820             825                 830

<210> SEQ ID NO 16
<211> LENGTH: 830
<212> TYPE: PRT
<213> ORGANISM: Thermus brockianus

<400> SEQUENCE: 16

Met Leu Pro Leu Phe Glu Pro Lys Gly Arg Val Leu Val Asp Gly
1               5                   10                  15

His His Leu Ala Tyr Arg Asn Phe Ala Leu Lys Gly Leu Thr Thr
                20                  25                  30

Ser Arg Gly Glu Pro Val Gln Gly Val Tyr Asp Phe Ala Lys Ser Leu
            35                  40                  45

Leu Lys Ala Leu Lys Glu Asp Gly Asp Val Val Ile Val Val Phe Asp
50                  55                  60

Ala Lys Ala Pro Ser Phe Arg His Glu Ala Tyr Gly Ala Tyr Lys Ala
65                  70                  75                  80

Gly Arg Ala Pro Thr Pro Glu Asp Phe Pro Arg Gln Leu Ala Leu Met
                85                  90                  95

Lys Glu Leu Val Asp Leu Leu Gly Leu Glu Arg Leu Glu Val Pro Gly
            100                 105                 110

Phe Glu Ala Asp Asp Val Leu Ala Ala Leu Ala Lys Lys Ala Glu Arg
        115                 120                 125

Glu Gly Tyr Glu Val Arg Ile Leu Thr Ala Asp Arg Asp Leu Phe Gln
    130                 135                 140

Leu Leu Ser Asp Arg Ile Ala Val Leu His Pro Glu Gly His Leu Ile
145                 150                 155                 160

Thr Pro Gly Trp Leu Trp Glu Arg Tyr Gly Leu Arg Pro Glu Gln Trp
                165                 170                 175

Val Asp Phe Arg Ala Leu Ala Gly Asp Pro Ser Asp Asn Ile Pro Gly
            180                 185                 190

Val Lys Gly Ile Gly Glu Lys Thr Ala Leu Lys Leu Leu Lys Glu Trp
        195                 200                 205

Gly Ser Leu Glu Asn Ile Gln Lys Asn Leu Asp Gln Val Ser Pro Pro
    210                 215                 220

Ser Val Arg Glu Lys Ile Gln Ala His Leu Asp Asp Leu Arg Leu Ser
225                 230                 235                 240

Gln Glu Leu Ser Arg Val Arg Thr Asp Leu Pro Leu Glu Val Asp Phe
                245                 250                 255

Arg Arg Arg Arg Glu Pro Asp Arg Glu Gly Leu Arg Ala Phe Leu Glu
            260                 265                 270

Arg Leu Glu Phe Gly Ser Leu Leu His Glu Phe Gly Leu Leu Glu Ser
        275                 280                 285

Pro Gln Ala Ala Glu Glu Ala Pro Trp Pro Pro Glu Gly Ala Phe
    290                 295                 300

Leu Gly Phe Arg Leu Ser Arg Pro Glu Pro Met Trp Ala Glu Leu Leu
305                 310                 315                 320
```

```
Ser Leu Ala Ala Ser Ala Lys Gly Arg Val Tyr Arg Ala Glu Ala Pro
            325                 330                 335

His Lys Ala Leu Ser Asp Leu Lys Glu Ile Arg Gly Leu Leu Ala Lys
        340                 345                 350

Asp Leu Ala Val Leu Ala Leu Arg Glu Gly Leu Gly Leu Pro Pro Thr
    355                 360                 365

Asp Asp Pro Met Leu Leu Ala Tyr Leu Leu Asp Pro Ser Asn Thr Thr
370                 375                 380

Pro Glu Gly Val Ala Arg Arg Tyr Gly Gly Glu Trp Thr Glu Glu Ala
385                 390                 395                 400

Gly Glu Arg Ala Leu Leu Ala Glu Arg Leu Tyr Glu Asn Leu Leu Ser
                405                 410                 415

Arg Leu Lys Gly Glu Glu Lys Leu Leu Trp Leu Tyr Glu Glu Val Glu
            420                 425                 430

Lys Pro Leu Ser Arg Val Leu Ala His Met Glu Ala Thr Gly Val Arg
        435                 440                 445

Leu Asp Val Pro Tyr Leu Arg Ala Leu Ser Leu Glu Val Ala Ala Glu
    450                 455                 460

Met Gly Arg Leu Glu Glu Val Phe Arg Leu Ala Gly His Pro Phe
465                 470                 475                 480

Asn Leu Asn Ser Arg Asp Gln Leu Glu Arg Val Leu Phe Asp Glu Leu
                485                 490                 495

Gly Leu Pro Pro Ile Gly Lys Thr Glu Lys Thr Gly Lys Arg Ser Thr
            500                 505                 510

Ser Ala Ala Val Leu Glu Ala Leu Arg Glu Ala His Pro Ile Val Glu
        515                 520                 525

Lys Ile Leu Gln Tyr Arg Glu Leu Ala Lys Leu Lys Gly Thr Tyr Ile
    530                 535                 540

Asp Pro Leu Pro Ala Leu Val His Pro Arg Thr Gly Arg Leu His Thr
545                 550                 555                 560

Arg Phe Asn Gln Thr Ala Thr Ala Thr Gly Arg Leu Ser Ser Ser Asp
                565                 570                 575

Pro Asn Leu Gln Asn Ile Pro Val Arg Thr Pro Leu Gly Gln Arg Ile
            580                 585                 590

Arg Arg Ala Phe Val Ala Glu Glu Gly Tyr Leu Leu Val Ala Leu Asp
        595                 600                 605

Tyr Ser Gln Ile Glu Leu Arg Val Leu Ala His Leu Ser Gly Asp Glu
    610                 615                 620

Asn Leu Ile Arg Val Phe Gln Glu Gly Arg Asp Ile His Thr Gln Thr
625                 630                 635                 640

Ala Ser Trp Met Phe Gly Leu Pro Ala Glu Ala Ile Asp Pro Leu Arg
                645                 650                 655

Arg Arg Ala Ala Lys Thr Ile Asn Tyr Gly Val Leu Tyr Gly Met Ser
            660                 665                 670

Ala His Arg Leu Ser Gln Glu Leu Gly Ile Pro Tyr Glu Glu Ala Val
        675                 680                 685

Ala Phe Ile Asp Arg Tyr Phe Gln Ser Tyr Pro Lys Val Lys Ala Trp
    690                 695                 700

Ile Glu Arg Thr Leu Glu Glu Gly Arg Gln Arg Gly Tyr Val Glu Thr
705                 710                 715                 720

Leu Phe Gly Arg Arg Arg Tyr Val Pro Asp Leu Asn Ala Arg Val Lys
                725                 730                 735

Ser Val Arg Glu Ala Ala Glu Arg Met Ala Phe Asn Met Pro Val Gln
```

```
                    740                 745                 750
Gly Thr Ala Ala Asp Leu Met Lys Leu Ala Met Val Arg Leu Phe Pro
            755                 760                 765

Arg Leu Pro Glu Val Gly Ala Arg Met Leu Leu Gln Val His Asp Glu
        770                 775                 780

Leu Leu Leu Glu Ala Pro Lys Glu Arg Ala Glu Ala Ala Ala Leu
785                 790                 795                 800

Ala Lys Glu Val Met Glu Gly Val Trp Pro Leu Ala Val Pro Leu Glu
                805                 810                 815

Val Glu Val Gly Ile Gly Glu Asp Trp Leu Ser Ala Lys Gly
            820                 825                 830

<210> SEQ ID NO 17
<211> LENGTH: 4
<212> TYPE: PRT
<213> ORGANISM: Thermus brockianus

<400> SEQUENCE: 17

Gln Gly Val Tyr
1

<210> SEQ ID NO 18
<211> LENGTH: 4
<212> TYPE: PRT
<213> ORGANISM: Thermus brockianus

<400> SEQUENCE: 18

Gly Ala Tyr Lys
1

<210> SEQ ID NO 19
<211> LENGTH: 4
<212> TYPE: PRT
<213> ORGANISM: Thermus brockianus

<400> SEQUENCE: 19

Leu Met Lys Glu
1

<210> SEQ ID NO 20
<211> LENGTH: 4
<212> TYPE: PRT
<213> ORGANISM: Thermus brockianus

<400> SEQUENCE: 20

Pro Gly Phe Glu
1

<210> SEQ ID NO 21
<211> LENGTH: 16
<212> TYPE: PRT
<213> ORGANISM: Thermus brockianus

<400> SEQUENCE: 21

Glu Arg Leu Glu Val Pro Gly Phe Glu Ala Asp Asp Val Leu Ala Ala
1               5                   10                  15

<210> SEQ ID NO 22
<211> LENGTH: 4
<212> TYPE: PRT
<213> ORGANISM: Thermus brockianus

<400> SEQUENCE: 22
```

```
Thr Pro Gly Trp
1

<210> SEQ ID NO 23
<211> LENGTH: 5
<212> TYPE: PRT
<213> ORGANISM: Thermus brockianus

<400> SEQUENCE: 23

Leu Ala Gly Asp Pro
1               5

<210> SEQ ID NO 24
<211> LENGTH: 4
<212> TYPE: PRT
<213> ORGANISM: Thermus brockianus

<400> SEQUENCE: 24

Asn Ile Gln Lys
1

<210> SEQ ID NO 25
<211> LENGTH: 5
<212> TYPE: PRT
<213> ORGANISM: Thermus brockianus

<400> SEQUENCE: 25

Gln Val Ser Pro Pro
1               5

<210> SEQ ID NO 26
<211> LENGTH: 4
<212> TYPE: PRT
<213> ORGANISM: Thermus brockianus

<400> SEQUENCE: 26

Glu Lys Ile Gln
1

<210> SEQ ID NO 27
<211> LENGTH: 5
<212> TYPE: PRT
<213> ORGANISM: Thermus brockianus

<400> SEQUENCE: 27

Arg Leu Ser Gln Glu
1               5

<210> SEQ ID NO 28
<211> LENGTH: 6
<212> TYPE: PRT
<213> ORGANISM: Thermus brockianus

<400> SEQUENCE: 28

Phe Arg Arg Arg Arg Glu
1               5

<210> SEQ ID NO 29
<211> LENGTH: 5
<212> TYPE: PRT
<213> ORGANISM: Thermus brockianus

<400> SEQUENCE: 29

Ser Pro Gln Ala Ala
1               5
```

```
<210> SEQ ID NO 30
<211> LENGTH: 4
<212> TYPE: PRT
<213> ORGANISM: Thermus brockianus

<400> SEQUENCE: 30

Leu Gly Phe Arg
1

<210> SEQ ID NO 31
<211> LENGTH: 4
<212> TYPE: PRT
<213> ORGANISM: Thermus brockianus

<400> SEQUENCE: 31

Glu Leu Leu Ser
1

<210> SEQ ID NO 32
<211> LENGTH: 7
<212> TYPE: PRT
<213> ORGANISM: Thermus brockianus

<400> SEQUENCE: 32

Ser Ala Lys Gly Arg Val Tyr
1               5

<210> SEQ ID NO 33
<211> LENGTH: 4
<212> TYPE: PRT
<213> ORGANISM: Thermus brockianus

<400> SEQUENCE: 33

Glu Ala Pro His
1

<210> SEQ ID NO 34
<211> LENGTH: 8
<212> TYPE: PRT
<213> ORGANISM: Thermus brockianus

<400> SEQUENCE: 34

Glu Ala Pro His Lys Ala Leu Ser
1               5

<210> SEQ ID NO 35
<211> LENGTH: 6
<212> TYPE: PRT
<213> ORGANISM: Thermus brockianus

<400> SEQUENCE: 35

Ala Glu Arg Leu Tyr Glu
1               5

<210> SEQ ID NO 36
<211> LENGTH: 5
<212> TYPE: PRT
<213> ORGANISM: Thermus brockianus

<400> SEQUENCE: 36

Leu Ser Arg Leu Lys
1               5

<210> SEQ ID NO 37
<211> LENGTH: 4
```

```
<212> TYPE: PRT
<213> ORGANISM: Thermus brockianus

<400> SEQUENCE: 37

Tyr Glu Glu Val
1

<210> SEQ ID NO 38
<211> LENGTH: 4
<212> TYPE: PRT
<213> ORGANISM: Thermus brockianus

<400> SEQUENCE: 38

Met Gly Arg Leu
1

<210> SEQ ID NO 39
<211> LENGTH: 5
<212> TYPE: PRT
<213> ORGANISM: Thermus brockianus

<400> SEQUENCE: 39

Ala Lys Leu Lys Gly
1               5

<210> SEQ ID NO 40
<211> LENGTH: 4
<212> TYPE: PRT
<213> ORGANISM: Thermus brockianus

<400> SEQUENCE: 40

Leu Pro Ala Leu
1

<210> SEQ ID NO 41
<211> LENGTH: 4
<212> TYPE: PRT
<213> ORGANISM: Thermus brockianus

<400> SEQUENCE: 41

Glu Gly Tyr Leu
1

<210> SEQ ID NO 42
<211> LENGTH: 4
<212> TYPE: PRT
<213> ORGANISM: Thermus brockianus

<400> SEQUENCE: 42

Leu Pro Ala Glu
1

<210> SEQ ID NO 43
<211> LENGTH: 5
<212> TYPE: PRT
<213> ORGANISM: Thermus brockianus

<400> SEQUENCE: 43

Pro Ala Glu Ala Ile
1               5

<210> SEQ ID NO 44
<211> LENGTH: 4
<212> TYPE: PRT
<213> ORGANISM: Thermus brockianus
```

<400> SEQUENCE: 44

Leu Arg Arg Arg
1

<210> SEQ ID NO 45
<211> LENGTH: 4
<212> TYPE: PRT
<213> ORGANISM: Thermus brockianus

<400> SEQUENCE: 45

Ile Asp Arg Tyr
1

<210> SEQ ID NO 46
<211> LENGTH: 5
<212> TYPE: PRT
<213> ORGANISM: Thermus brockianus

<400> SEQUENCE: 46

Tyr Pro Lys Val Lys
1               5

<210> SEQ ID NO 47
<211> LENGTH: 4
<212> TYPE: PRT
<213> ORGANISM: Thermus brockianus

<400> SEQUENCE: 47

Gly Arg Gln Arg
1

<210> SEQ ID NO 48
<211> LENGTH: 9
<212> TYPE: PRT
<213> ORGANISM: Thermus brockianus

<400> SEQUENCE: 48

Arg Leu Phe Pro Arg Leu Pro Glu Val
1               5

<210> SEQ ID NO 49
<211> LENGTH: 4
<212> TYPE: PRT
<213> ORGANISM: Thermus brockianus

<400> SEQUENCE: 49

Gly Val Trp Pro
1

<210> SEQ ID NO 50
<211> LENGTH: 4
<212> TYPE: PRT
<213> ORGANISM: Thermus brockianus

<400> SEQUENCE: 50

Arg Asn Phe Phe
1

<210> SEQ ID NO 51
<211> LENGTH: 17
<212> TYPE: DNA
<213> ORGANISM: Thermus brockianus

<400> SEQUENCE: 51
cccacctcca cctccag                                              17

```
<210> SEQ ID NO 52
<211> LENGTH: 23
<212> TYPE: DNA
<213> ORGANISM: Thermus brockianus

<400> SEQUENCE: 52
cgacctcaac gcccgggtaa aga                                              23

<210> SEQ ID NO 53
<211> LENGTH: 25
<212> TYPE: DNA
<213> ORGANISM: Thermus brockianus

<400> SEQUENCE: 53
gcttttggcg aagccgtaga ccccct                                            25

<210> SEQ ID NO 54
<211> LENGTH: 25
<212> TYPE: DNA
<213> ORGANISM: Thermus brockianus

<400> SEQUENCE: 54
catatgcttc ccctctttga gccca                                             25

<210> SEQ ID NO 55
<211> LENGTH: 24
<212> TYPE: DNA
<213> ORGANISM: Thermus brockianus

<400> SEQUENCE: 55
gtcgactagc ccttggcgga aagc                                              24

<210> SEQ ID NO 56
<211> LENGTH: 541
<212> TYPE: PRT
<213> ORGANISM: Thermus brockianus

<400> SEQUENCE: 56

Gln Ala Ala Glu Glu Ala Pro Trp Pro Pro Glu Gly Ala Phe Leu
1               5                   10                  15

Gly Phe Arg Leu Ser Arg Pro Glu Pro Met Trp Ala Glu Leu Leu Ser
            20                  25                  30

Leu Ala Ala Ser Ala Lys Gly Arg Val Tyr Arg Ala Glu Ala Pro His
        35                  40                  45

Lys Ala Leu Ser Asp Leu Lys Glu Ile Arg Gly Leu Leu Ala Lys Asp
    50                  55                  60

Leu Ala Val Leu Ala Leu Arg Glu Gly Leu Gly Leu Pro Pro Thr Asp
65                  70                  75                  80

Asp Pro Met Leu Leu Ala Tyr Leu Leu Asp Pro Ser Asn Thr Thr Pro
                85                  90                  95

Glu Gly Val Ala Arg Arg Tyr Gly Gly Glu Trp Thr Glu Glu Ala Gly
            100                 105                 110

Glu Arg Ala Leu Leu Ala Glu Arg Leu Tyr Glu Asn Leu Leu Ser Arg
        115                 120                 125

Leu Lys Gly Glu Glu Lys Leu Leu Trp Leu Tyr Glu Glu Val Glu Lys
    130                 135                 140

Pro Leu Ser Arg Val Leu Ala His Met Glu Ala Thr Gly Val Arg Leu
145                 150                 155                 160

Asp Val Pro Tyr Leu Arg Ala Leu Ser Leu Glu Val Ala Ala Glu Met
```

```
                        165                 170                 175
Gly Arg Leu Glu Glu Val Phe Arg Leu Ala Gly His Pro Phe Asn
            180                 185                 190

Leu Asn Ser Arg Asp Gln Leu Glu Arg Val Leu Phe Asp Glu Leu Gly
            195                 200                 205

Leu Pro Pro Ile Gly Lys Thr Glu Lys Thr Gly Lys Arg Ser Thr Ser
            210                 215                 220

Ala Ala Val Leu Glu Ala Leu Arg Glu Ala His Pro Ile Val Glu Lys
225                 230                 235                 240

Ile Leu Gln Tyr Arg Glu Leu Ala Lys Leu Lys Gly Thr Tyr Ile Asp
                245                 250                 255

Leu Leu Pro Ala Leu Val His Pro Arg Thr Gly Arg Leu His Thr Arg
            260                 265                 270

Phe Asn Gln Thr Ala Thr Ala Thr Gly Arg Leu Ser Ser Ser Asp Pro
            275                 280                 285

Asn Leu Gln Asn Ile Pro Val Arg Thr Pro Leu Gly Gln Arg Ile Arg
            290                 295                 300

Arg Ala Phe Val Ala Glu Glu Gly Tyr Leu Leu Val Ala Leu Asp Tyr
305                 310                 315                 320

Ser Gln Ile Glu Leu Arg Val Leu Ala His Leu Ser Gly Asp Glu Asn
                325                 330                 335

Leu Ile Arg Val Phe Gln Glu Gly Arg Asp Ile His Thr Gln Thr Ala
            340                 345                 350

Ser Trp Met Phe Gly Leu Pro Ala Glu Ala Ile Asp Pro Leu Arg Arg
            355                 360                 365

Arg Ala Ala Lys Thr Ile Asn Phe Gly Val Leu Tyr Gly Met Ser Ala
370                 375                 380

His Arg Leu Ser Gln Glu Leu Gly Ile Pro Tyr Glu Glu Ala Val Ala
385                 390                 395                 400

Phe Ile Asp Arg Tyr Phe Gln Ser Tyr Pro Lys Val Lys Ala Trp Ile
                405                 410                 415

Glu Arg Thr Leu Glu Glu Gly Arg Gln Arg Gly Tyr Val Glu Thr Leu
            420                 425                 430

Phe Gly Arg Arg Arg Tyr Val Pro Asp Leu Asn Ala Arg Val Lys Ser
            435                 440                 445

Val Arg Glu Ala Ala Glu Arg Met Ala Phe Asn Met Pro Val Gln Gly
450                 455                 460

Thr Ala Ala Asp Leu Met Lys Leu Ala Met Val Arg Leu Phe Pro Arg
465                 470                 475                 480

Leu Pro Glu Val Gly Ala Arg Met Leu Leu Gln Val His Asp Glu Leu
                485                 490                 495

Leu Leu Glu Ala Pro Lys Glu Arg Ala Glu Glu Ala Ala Ala Leu Ala
            500                 505                 510

Lys Glu Val Met Glu Gly Val Trp Pro Leu Ala Val Pro Leu Glu Val
            515                 520                 525

Glu Val Gly Ile Gly Glu Asp Trp Leu Ser Ala Lys Gly
530                 535                 540

<210> SEQ ID NO 57
<211> LENGTH: 541
<212> TYPE: PRT
<213> ORGANISM: Thermus brockianus

<400> SEQUENCE: 57

Gln Ala Ala Glu Glu Ala Pro Trp Pro Pro Pro Glu Gly Ala Phe Leu
```

-continued

```
  1               5              10             15
Gly Phe Arg Leu Ser Arg Pro Glu Pro Met Trp Ala Glu Leu Leu Ser
             20              25              30

Leu Ala Ala Ser Ala Lys Gly Arg Val Tyr Arg Ala Glu Ala Pro His
             35              40              45

Lys Ala Leu Ser Asp Leu Lys Glu Ile Arg Gly Leu Leu Ala Lys Asp
 50              55              60

Leu Ala Val Leu Ala Leu Arg Glu Gly Leu Gly Leu Pro Pro Thr Asp
 65              70              75              80

Asp Pro Met Leu Leu Ala Tyr Leu Leu Asp Pro Ser Asn Thr Thr Pro
             85              90              95

Glu Gly Val Ala Arg Arg Tyr Gly Gly Glu Trp Thr Glu Glu Ala Gly
            100             105             110

Glu Arg Ala Leu Leu Ala Glu Arg Leu Tyr Glu Asn Leu Leu Ser Arg
            115             120             125

Leu Lys Gly Glu Glu Lys Leu Leu Trp Leu Tyr Glu Glu Val Glu Lys
            130             135             140

Pro Leu Ser Arg Val Leu Ala His Met Glu Ala Thr Gly Val Arg Leu
145             150             155             160

Asp Val Pro Tyr Leu Arg Ala Leu Ser Leu Glu Val Ala Ala Glu Met
            165             170             175

Gly Arg Leu Glu Glu Val Phe Arg Leu Ala Gly His Pro Phe Asn
            180             185             190

Leu Asn Ser Arg Asp Gln Leu Glu Arg Val Leu Phe Asp Glu Leu Gly
            195             200             205

Leu Pro Pro Ile Gly Lys Thr Glu Lys Thr Gly Lys Arg Ser Thr Ser
            210             215             220

Ala Ala Val Leu Glu Ala Leu Arg Glu Ala His Pro Ile Val Glu Lys
225             230             235             240

Ile Leu Gln Tyr Arg Glu Leu Ala Lys Leu Lys Gly Thr Tyr Ile Asp
            245             250             255

Pro Leu Pro Ala Leu Val His Pro Arg Thr Gly Arg Leu His Thr Arg
            260             265             270

Phe Asn Gln Thr Ala Thr Ala Thr Gly Arg Leu Ser Ser Ser Asp Pro
            275             280             285

Asn Leu Gln Asn Ile Pro Val Arg Thr Pro Leu Gly Gln Arg Ile Arg
            290             295             300

Arg Ala Phe Val Ala Glu Glu Gly Tyr Leu Leu Val Ala Leu Asp Tyr
305             310             315             320

Ser Gln Ile Glu Leu Arg Val Leu Ala His Leu Ser Gly Asp Glu Asn
            325             330             335

Leu Ile Arg Val Phe Gln Glu Gly Arg Asp Ile His Thr Gln Thr Ala
            340             345             350

Ser Trp Met Phe Gly Leu Pro Ala Glu Ala Ile Asp Pro Leu Arg Arg
            355             360             365

Arg Ala Ala Lys Thr Ile Asn Phe Gly Val Leu Tyr Gly Met Ser Ala
            370             375             380

His Arg Leu Ser Gln Glu Leu Gly Ile Pro Tyr Glu Glu Ala Val Ala
385             390             395             400

Phe Ile Asp Arg Tyr Phe Gln Ser Tyr Pro Lys Val Lys Ala Trp Ile
            405             410             415

Glu Arg Thr Leu Glu Glu Gly Arg Gln Arg Gly Tyr Val Glu Thr Leu
            420             425             430
```

```
Phe Gly Arg Arg Arg Tyr Val Pro Asp Leu Asn Ala Arg Val Lys Ser
        435                 440                 445

Val Arg Glu Ala Ala Glu Arg Met Ala Phe Asn Met Pro Val Gln Gly
450                 455                 460

Thr Ala Ala Asp Leu Met Lys Leu Ala Met Val Arg Leu Phe Pro Arg
465                 470                 475                 480

Leu Pro Glu Val Gly Ala Arg Met Leu Leu Gln Val His Asp Glu Leu
                485                 490                 495

Leu Leu Glu Ala Pro Lys Glu Arg Ala Glu Ala Ala Ala Leu Ala
                500                 505                 510

Lys Glu Val Met Glu Gly Val Trp Pro Leu Ala Val Pro Leu Glu Val
                515                 520                 525

Glu Val Gly Ile Gly Glu Asp Trp Leu Ser Ala Lys Gly
530                 535                 540

<210> SEQ ID NO 58
<211> LENGTH: 18
<212> TYPE: DNA
<213> ORGANISM: Thermus brockianus

<400> SEQUENCE: 58
ggccaccacc tggcctac                                                        18

<210> SEQ ID NO 59
<211> LENGTH: 782
<212> TYPE: PRT
<213> ORGANISM: Thermus aquaticus

<400> SEQUENCE: 59

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
                20                  25                  30

Leu Thr Thr Ser Arg Gly Glu Pro Val Gln Ala Val Tyr Gly Phe Ala
            35                  40                  45

Lys Ser Leu Leu Lys Ala Leu Lys Glu Asp Gly Asp Ala Val Ile Val
50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
                100                 105                 110

Val Pro Gly Tyr Glu Ala Asp Asp Val Leu Ala Ser Leu Ala Lys Lys
            115                 120                 125

Ala Glu Lys Glu Gly Tyr Glu Val Arg Ile Leu Thr Ala Asp Lys Asp
130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
                180                 185                 190

Leu Pro Gly Val Lys Gly Ile Gly Glu Lys Thr Ala Arg Lys Leu Leu
            195                 200                 205

Glu Glu Trp Gly Ser Leu Glu Ala Leu Leu Lys Asn Leu Asp Arg Leu
210                 215                 220
```

-continued

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
            245                 250                 255

Asp Phe Ala Lys Arg Arg Glu Pro Asp Arg Glu Arg Leu Arg Ala Phe
        260                 265                 270

Leu Glu Arg Leu Glu Phe Gly Ser Leu Leu His Glu Phe Gly Leu Leu
    275                 280                 285

Glu Ser Pro Lys Ala Leu Glu Glu Ala Pro Trp Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Arg Gly Gly Arg Val His Arg Ala Pro
            325                 330                 335

Glu Pro Tyr Lys Ala Leu Arg Asp Leu Lys Glu Ala Arg Gly Leu Leu
        340                 345                 350

Ala Lys Asp Leu Ser Val Leu Ala Leu Arg Glu Gly Leu Gly Leu Pro
        355                 360                 365

Pro Gly Asp Asp Pro Met Leu Leu Ala Tyr Leu Leu Asp Pro Ser Asn
    370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
            405                 410                 415

Trp Gly Arg Leu Glu Gly Glu Glu Arg Leu Leu Trp Leu Tyr Arg Glu
        420                 425                 430

Val Glu Arg Pro Leu Ser Ala Val Leu Ala His Met Glu Ala Thr Gly
    435                 440                 445

Val Arg Leu Asp Val Ala Tyr Leu Arg Ala Leu Ser Leu Glu Val Ala
    450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
            485                 490                 495

Glu Leu Gly Leu Pro Ala Ile Gly Lys Thr Glu Lys Thr Gly Lys Arg
        500                 505                 510

Ser Thr Ser Ala Ala Val Leu Glu Ala Leu Arg Glu Ala His Pro Ile
    515                 520                 525

Val Glu Lys Ile Leu Gln Tyr Arg Glu Leu Thr Lys Leu Lys Ser Thr
    530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
            565                 570                 575

Ser Asp Pro Asn Leu Gln Asn Ile Pro Val Arg Thr Pro Leu Gly Gln
        580                 585                 590

Arg Ile Arg Arg Phe Gly Val Pro Arg Glu Ala Val Asp Pro Leu Met
        595                 600                 605

Arg Arg Ala Ala Lys Thr Ile Asn Phe Gly Val Leu Tyr Gly Met Ser
610                 615                 620

Ala His Arg Leu Ser Gln Glu Leu Ala Ile Pro Tyr Glu Glu Ala Gln
625                 630                 635                 640

Ala Phe Ile Glu Arg Tyr Phe Gln Ser Phe Pro Lys Val Arg Ala Trp

```
                    645                 650                 655
Ile Glu Lys Thr Leu Glu Glu Gly Arg Arg Gly Tyr Val Glu Thr
                660                 665                 670
Leu Phe Gly Arg Arg Arg Tyr Val Pro Asp Leu Glu Ala Arg Val Lys
            675                 680                 685
Ser Val Arg Glu Ala Ala Glu Arg Met Ala Phe Asn Met Pro Val Gln
        690                 695                 700
Gly Thr Ala Ala Asp Leu Met Lys Leu Ala Met Val Lys Leu Phe Pro
    705                 710                 715                 720
Arg Leu Glu Glu Met Gly Ala Arg Met Leu Leu Gln Val His Asp Glu
                725                 730                 735
Leu Val Leu Glu Ala Pro Lys Glu Arg Ala Glu Ala Val Ala Arg Leu
                740                 745                 750
Ala Lys Glu Val Met Glu Gly Val Tyr Pro Leu Ala Val Pro Leu Glu
            755                 760                 765
Val Glu Val Gly Ile Gly Glu Asp Trp Leu Ser Ala Lys Glu
    770                 775                 780

<210> SEQ ID NO 60
<211> LENGTH: 834
<212> TYPE: PRT
<213> ORGANISM: Thermus thermophilus

<400> SEQUENCE: 60

Met Glu Ala Met Leu Pro Leu Phe Glu Pro Lys Gly Arg Val Leu Leu
1               5                   10                  15
Val Asp Gly His His Leu Ala Tyr Arg Thr Phe Phe Ala Leu Lys Gly
                20                  25                  30
Leu Thr Thr Ser Arg Gly Glu Pro Val Gln Ala Val Tyr Gly Phe Ala
            35                  40                  45
Lys Ser Leu Leu Lys Ala Leu Lys Glu Asp Gly Tyr Lys Ala Val Phe
        50                  55                  60
Val Val Phe Asp Ala Lys Ala Pro Ser Phe Arg His Glu Ala Tyr Glu
65                  70                  75                  80
Ala Tyr Lys Ala Gly Arg Ala Pro Thr Pro Glu Asp Phe Pro Arg Gln
                85                  90                  95
Leu Ala Leu Ile Lys Glu Leu Val Asp Leu Leu Gly Phe Thr Arg Leu
            100                 105                 110
Glu Val Pro Gly Tyr Glu Ala Asp Asp Val Leu Ala Thr Leu Ala Lys
        115                 120                 125
Lys Ala Glu Lys Glu Gly Tyr Glu Val Arg Ile Leu Thr Ala Asp Arg
    130                 135                 140
Asp Leu Tyr Gln Leu Val Ser Asp Arg Val Ala Val Leu His Pro Glu
145                 150                 155                 160
Gly His Leu Ile Thr Pro Glu Trp Leu Trp Glu Lys Tyr Gly Leu Arg
                165                 170                 175
Pro Glu Gln Trp Val Asp Phe Arg Ala Leu Val Gly Asp Pro Ser Asp
            180                 185                 190
Asn Leu Pro Gly Val Lys Gly Ile Gly Glu Lys Thr Ala Leu Lys Leu
        195                 200                 205
Leu Lys Glu Trp Gly Ser Leu Glu Asn Leu Leu Lys Asn Leu Asp Arg
    210                 215                 220
Val Lys Pro Glu Asn Val Arg Glu Lys Ile Lys Ala His Leu Glu Asp
225                 230                 235                 240
Leu Arg Leu Ser Leu Glu Leu Ser Arg Val Arg Thr Asp Leu Pro Leu
```

```
                245                 250                 255
Glu Val Asp Leu Ala Gln Gly Arg Glu Pro Asp Arg Glu Gly Leu Arg
            260                 265                 270

Ala Phe Leu Glu Arg Leu Glu Phe Gly Ser Leu Leu His Glu Phe Gly
        275                 280                 285

Leu Leu Glu Ala Pro Ala Pro Leu Glu Glu Ala Pro Trp Pro Pro
    290                 295                 300

Glu Gly Ala Phe Val Gly Phe Val Leu Ser Arg Pro Gly Pro Met Trp
305                 310                 315                 320

Ala Glu Leu Lys Ala Leu Ala Ala Cys Arg Asp Gly Arg Val His Arg
            325                 330                 335

Ala Ala Asp Pro Leu Ala Gly Leu Lys Asp Leu Lys Glu Val Arg Gly
        340                 345                 350

Leu Leu Ala Lys Asp Leu Ala Val Leu Ala Ser Arg Glu Gly Leu Asp
    355                 360                 365

Leu Val Pro Gly Asp Asp Pro Met Leu Leu Ala Tyr Leu Leu Asp Pro
370                 375                 380

Ser Asn Thr Thr Pro Glu Gly Val Ala Arg Arg Tyr Gly Gly Glu Trp
385                 390                 395                 400

Thr Glu Asp Ala Ala His Arg Ala Leu Leu Ser Glu Arg Leu His Arg
            405                 410                 415

Asn Leu Leu Lys Arg Leu Glu Gly Glu Lys Leu Leu Trp Leu Tyr
        420                 425                 430

His Glu Val Glu Lys Pro Leu Ser Arg Val Leu Ala His Met Glu Ala
            435                 440                 445

Thr Gly Val Arg Leu Asp Val Ala Tyr Leu Gln Ala Leu Ser Leu Glu
        450                 455                 460

Leu Ala Glu Glu Ile Arg Arg Leu Glu Glu Glu Val Phe Arg Leu Ala
465                 470                 475                 480

Gly His Pro Phe Asn Leu Asn Ser Arg Asp Gln Leu Glu Arg Val Leu
            485                 490                 495

Phe Asp Glu Leu Arg Leu Pro Ala Leu Gly Lys Thr Gln Lys Thr Gly
        500                 505                 510

Lys Arg Ser Thr Ser Ala Ala Val Leu Glu Ala Leu Arg Glu Ala His
    515                 520                 525

Pro Ile Val Glu Lys Ile Leu Gln His Arg Glu Leu Thr Lys Leu Lys
        530                 535                 540

Asn Thr Tyr Val Asp Pro Leu Pro Ser Leu Val His Pro Arg Thr Gly
545                 550                 555                 560

Arg Leu His Thr Arg Phe Asn Gln Thr Ala Thr Ala Thr Gly Arg Leu
            565                 570                 575

Ser Ser Ser Asp Pro Asn Leu Gln Asn Ile Pro Val Arg Thr Pro Leu
        580                 585                 590

Gly Gln Arg Ile Arg Arg Ala Phe Val Ala Glu Ala Gly Trp Ala Leu
    595                 600                 605

Val Ala Leu Asp Tyr Ser Gln Ile Glu Leu Arg Val Leu Ala His Leu
610                 615                 620

Ser Gly Asp Glu Asn Leu Ile Arg Val Phe Gln Glu Gly Lys Asp Ile
625                 630                 635                 640

His Thr Gln Thr Ala Ser Trp Met Phe Gly Val Pro Pro Glu Ala Val
            645                 650                 655

Asp Pro Leu Met Arg Arg Ala Ala Lys Thr Val Asn Phe Gly Val Leu
        660                 665                 670
```

-continued

```
Tyr Gly Met Ser Ala His Arg Leu Ser Gln Glu Leu Ala Ile Pro Tyr
            675                 680                 685

Glu Glu Ala Val Ala Phe Ile Glu Arg Tyr Phe Gln Ser Phe Pro Lys
690                 695                 700

Val Arg Ala Trp Ile Glu Lys Thr Leu Glu Glu Gly Arg Lys Arg Gly
705                 710                 715                 720

Tyr Val Glu Thr Leu Phe Gly Arg Arg Tyr Val Pro Asp Leu Asn
                725                 730                 735

Ala Arg Val Lys Ser Val Arg Glu Ala Ala Glu Arg Met Ala Phe Asn
            740                 745                 750

Met Pro Val Gln Gly Thr Ala Ala Asp Leu Met Lys Leu Ala Met Val
            755                 760                 765

Lys Leu Phe Pro Arg Leu Arg Glu Met Gly Ala Arg Met Leu Leu Gln
770                 775                 780

Val His Asp Glu Leu Leu Leu Glu Ala Pro Gln Ala Arg Ala Glu Glu
785                 790                 795                 800

Val Ala Ala Leu Ala Lys Glu Ala Met Glu Lys Ala Tyr Pro Leu Ala
                805                 810                 815

Val Pro Leu Glu Val Glu Val Gly Met Gly Glu Asp Trp Leu Ser Ala
                820                 825                 830

Lys Gly

<210> SEQ ID NO 61
<211> LENGTH: 833
<212> TYPE: PRT
<213> ORGANISM: Thermus filiformis

<400> SEQUENCE: 61

Met Thr Pro Leu Phe Asp Leu Glu Glu Pro Pro Lys Arg Val Leu Leu
1               5                   10                  15

Val Asp Gly His His Leu Ala Tyr Arg Thr Phe Tyr Ala Leu Ser Leu
            20                  25                  30

Thr Thr Ser Arg Gly Glu Pro Val Gln Met Val Tyr Gly Phe Ala Arg
        35                  40                  45

Ser Leu Leu Lys Ala Leu Lys Glu Asp Gly Gln Ala Val Val Val Val
    50                  55                  60

Phe Asp Ala Lys Ala Pro Ser Phe Arg His Glu Ala Tyr Glu Ala Tyr
65                  70                  75                  80

Lys Ala Gly Arg Ala Pro Thr Pro Glu Asp Phe Pro Arg Gln Leu Ala
                85                  90                  95

Leu Val Lys Arg Leu Val Asp Leu Leu Gly Leu Val Arg Leu Glu Ala
            100                 105                 110

Pro Gly Tyr Glu Ala Asp Asp Val Leu Gly Thr Leu Ala Lys Lys Ala
        115                 120                 125

Glu Arg Glu Gly Met Glu Val Arg Ile Leu Thr Gly Asp Arg Asp Phe
    130                 135                 140

Phe Gln Leu Leu Ser Glu Lys Val Ser Val Leu Leu Pro Asp Gly Thr
145                 150                 155                 160

Leu Val Thr Pro Lys Asp Val Gln Glu Lys Tyr Gly Val Pro Pro Glu
                165                 170                 175

Arg Trp Val Asp Phe Arg Ala Leu Thr Gly Asp Arg Ser Asp Asn Ile
            180                 185                 190

Pro Gly Val Ala Gly Ile Gly Glu Lys Thr Ala Leu Arg Leu Leu Ala
        195                 200                 205

Glu Trp Gly Ser Val Glu Asn Leu Leu Lys Asn Leu Asp Arg Val Lys
```

```
            210                 215                 220
Pro Asp Ser Leu Arg Arg Lys Ile Glu Ala His Leu Glu Asp Leu His
225                 230                 235                 240

Leu Ser Leu Asp Leu Ala Arg Ile Arg Thr Asp Leu Pro Leu Glu Val
                245                 250                 255

Asp Phe Lys Ala Leu Arg Arg Thr Pro Asp Leu Glu Gly Leu Arg
            260                 265                 270

Ala Phe Leu Glu Glu Leu Glu Phe Gly Ser Leu Leu His Glu Phe Gly
                275                 280                 285

Leu Leu Gly Gly Glu Lys Pro Arg Glu Ala Pro Trp Pro Pro
290                 295                 300

Glu Gly Ala Phe Val Gly Phe Leu Leu Ser Lys Glu Pro Met Trp
305                 310                 315                 320

Ala Glu Leu Leu Ala Leu Ala Ala Ser Glu Gly Arg Val His Arg
                325                 330                 335

Ala Thr Ser Pro Val Glu Ala Leu Ala Asp Leu Lys Glu Ala Arg Gly
                340                 345                 350

Phe Leu Ala Lys Asp Leu Ala Val Leu Ala Leu Arg Glu Gly Val Ala
                355                 360                 365

Leu Asp Pro Thr Asp Pro Leu Leu Val Ala Tyr Leu Leu Asp Pro
370                 375                 380

Ala Asn Thr His Pro Glu Gly Val Ala Arg Arg Tyr Gly Gly Glu Phe
385                 390                 395                 400

Thr Glu Asp Ala Ala Glu Arg Ala Leu Leu Ser Glu Arg Leu Phe Gln
                405                 410                 415

Asn Leu Phe Pro Arg Leu Ser Glu Lys Leu Leu Trp Leu Tyr Gln Glu
                420                 425                 430

Val Glu Arg Pro Leu Ser Arg Val Leu Ala His Met Glu Ala Arg Gly
                435                 440                 445

Val Arg Leu Asp Val Pro Leu Leu Glu Ala Leu Ser Phe Glu Leu Glu
                450                 455                 460

Lys Glu Met Glu Arg Leu Glu Gly Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Thr Pro Val Gly Arg Thr Glu Lys Thr Gly Lys Arg
                500                 505                 510

Ser Thr Ala Gln Gly Ala Leu Glu Ala Leu Arg Gly Ala His Pro Ile
                515                 520                 525

Val Glu Leu Ile Leu Gln Tyr Arg Glu Leu Ser Lys Leu Lys Ser Thr
                530                 535                 540

Tyr Leu Asp Pro Leu Pro Arg Leu Val His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
                580                 585                 590

Arg Ile Arg Lys Ala Phe Val Ala Glu Glu Gly Trp Leu Leu Leu Ala
                595                 600                 605

Ala Asp Tyr Ser Gln Ile Glu Leu Arg Val Leu Ala His Leu Ser Gly
                610                 615                 620

Asp Glu Asn Leu Lys Arg Val Phe Arg Glu Gly Lys Asp Ile His Thr
625                 630                 635                 640
```

```
Glu Thr Ala Ala Trp Met Phe Gly Leu Asp Pro Ala Leu Val Asp Pro
            645                 650                 655

Lys Met Arg Arg Ala Ala Lys Thr Val Asn Phe Gly Val Leu Tyr Gly
        660                 665                 670

Met Ser Ala His Arg Leu Ser Gln Glu Leu Gly Ile Asp Tyr Lys Glu
            675                 680                 685

Ala Glu Ala Phe Ile Glu Arg Tyr Phe Gln Ser Phe Pro Lys Val Arg
        690                 695                 700

Ala Trp Ile Glu Arg Thr Leu Glu Glu Gly Arg Thr Arg Gly Tyr Val
705                 710                 715                 720

Glu Thr Leu Phe Gly Arg Arg Tyr Val Pro Asp Leu Ala Ser Arg
            725                 730                 735

Val Arg Ser Val Arg Glu Ala Ala Glu Arg Met Ala Phe Asn Met Pro
        740                 745                 750

Val Gln Gly Thr Ala Ala Asp Leu Met Lys Ile Ala Met Val Lys Leu
            755                 760                 765

Phe Pro Arg Leu Lys Pro Leu Gly Ala His Leu Leu Leu Gln Val His
    770                 775                 780

Asp Glu Leu Val Leu Glu Val Pro Glu Asp Arg Ala Glu Glu Ala Lys
785                 790                 795                 800

Ala Leu Val Lys Glu Val Met Glu Asn Ala Tyr Pro Leu Asp Val Pro
            805                 810                 815

Leu Glu Val Glu Val Gly Val Gly Arg Asp Trp Leu Glu Ala Lys Gln
            820                 825                 830

Asp

<210> SEQ ID NO 62
<211> LENGTH: 831
<212> TYPE: PRT
<213> ORGANISM: Thermus flavus

<400> SEQUENCE: 62

Met Ala Met Leu Pro Leu Phe Glu Pro Lys Gly Arg Val Leu Leu Val
1               5                   10                  15

Asp Gly His His Leu Ala Tyr Arg Thr Phe Phe Ala Leu Lys Gly Leu
            20                  25                  30

Thr Thr Ser Arg Gly Glu Pro Val Gln Ala Val Tyr Gly Phe Ala Lys
        35                  40                  45

Ser Leu Leu Lys Ala Leu Lys Glu Asp Gly Asp Val Val Val Val Val
    50                  55                  60

Phe Asp Ala Lys Ala Pro Ser Phe Arg His Glu Ala Tyr Glu Ala Tyr
65                  70                  75                  80

Lys Ala Gly Arg Ala Pro Thr Pro Glu Asp Phe Pro Arg Gln Leu Ala
            85                  90                  95

Leu Ile Lys Glu Leu Val Asp Leu Leu Gly Leu Val Arg Leu Glu Val
            100                 105                 110

Pro Gly Phe Glu Ala Asp Asp Val Leu Ala Thr Leu Ala Lys Arg Ala
        115                 120                 125

Glu Lys Glu Gly Tyr Glu Val Arg Ile Leu Thr Ala Asp Arg Asp Leu
    130                 135                 140

Tyr Gln Leu Leu Ser Glu Arg Ile Ala Ile Leu His Pro Glu Gly Tyr
145                 150                 155                 160

Leu Ile Thr Pro Ala Trp Leu Tyr Glu Lys Tyr Gly Leu Arg Pro Glu
            165                 170                 175

Gln Trp Val Asp Tyr Arg Ala Leu Ala Gly Asp Pro Ser Asp Asn Ile
```

```
                180             185             190
Pro Gly Val Lys Gly Ile Gly Glu Lys Thr Ala Gln Arg Leu Ile Arg
            195                 200                 205
Glu Trp Gly Ser Leu Glu Asn Leu Phe Gln His Leu Asp Gln Val Lys
    210                 215                 220
Pro Ser Leu Arg Glu Lys Leu Gln Ala Gly Met Glu Ala Leu Ala Leu
225                 230                 235                 240
Ser Arg Lys Leu Ser Gln Val His Thr Asp Leu Pro Leu Glu Val Asp
                245                 250                 255
Phe Gly Arg Arg Arg Thr Pro Asn Leu Glu Gly Leu Arg Ala Phe Leu
            260                 265                 270
Glu Arg Leu Glu Phe Gly Ser Leu Leu His Glu Phe Gly Leu Leu Glu
        275                 280                 285
Gly Pro Lys Ala Ala Glu Glu Ala Pro Trp Pro Pro Glu Gly Ala
    290                 295                 300
Phe Leu Gly Phe Ser Phe Ser Arg Pro Glu Pro Met Trp Ala Glu Leu
305                 310                 315                 320
Leu Ala Leu Ala Gly Ala Trp Glu Gly Arg Leu His Arg Ala Gln Asp
                325                 330                 335
Pro Leu Arg Gly Leu Arg Asp Leu Lys Gly Val Arg Gly Ile Leu Ala
            340                 345                 350
Lys Asp Leu Ala Val Leu Ala Leu Arg Glu Gly Leu Asp Leu Phe Pro
        355                 360                 365
Glu Asp Asp Pro Met Leu Leu Ala Tyr Leu Leu Asp Pro Ser Asn Thr
    370                 375                 380
Thr Pro Glu Gly Val Ala Arg Arg Tyr Gly Gly Glu Trp Thr Glu Asp
385                 390                 395                 400
Ala Gly Glu Arg Ala Leu Leu Ala Glu Arg Leu Phe Gln Thr Leu Lys
                405                 410                 415
Glu Arg Leu Lys Gly Glu Glu Arg Leu Leu Trp Leu Tyr Glu Glu Val
            420                 425                 430
Glu Lys Pro Leu Ser Arg Val Leu Ala Arg Met Glu Ala Thr Gly Val
        435                 440                 445
Arg Leu Asp Val Ala Tyr Leu Gln Ala Leu Ser Leu Glu Val Glu Ala
    450                 455                 460
Glu Val Arg Gln Leu Glu Glu Val Phe Arg Leu Ala Gly His Pro
465                 470                 475                 480
Phe Asn Leu Asn Ser Arg Asp Gln Leu Glu Arg Val Leu Phe Asp Glu
                485                 490                 495
Leu Gly Leu Pro Ala Ile Gly Lys Thr Glu Lys Thr Gly Lys Arg Ser
            500                 505                 510
Thr Ser Ala Ala Val Leu Glu Ala Leu Arg Glu Ala His Pro Ile Val
        515                 520                 525
Asp Arg Ile Leu Gln Tyr Arg Glu Leu Thr Lys Leu Lys Asn Thr Tyr
    530                 535                 540
Ile Asp Pro Leu Pro Ala Leu Val His Pro Lys Thr Gly Arg Leu His
545                 550                 555                 560
Thr Arg Phe Asn Gln Thr Ala Thr Ala Thr Gly Arg Leu Ser Ser Ser
                565                 570                 575
Asp Pro Asn Leu Gln Asn Ile Pro Val Arg Thr Pro Leu Gly Gln Arg
            580                 585                 590
Ile Arg Arg Ala Phe Val Ala Glu Glu Gly Trp Val Leu Val Val Leu
        595                 600                 605
```

-continued

```
Asp Tyr Ser Gln Ile Glu Leu Arg Val Leu Ala His Leu Ser Gly Asp
    610                 615                 620

Glu Asn Leu Ile Arg Val Phe Gln Glu Gly Arg Asp Ile His Thr Gln
625                 630                 635                 640

Thr Ala Ser Trp Met Phe Gly Val Ser Pro Glu Gly Val Asp Pro Leu
                645                 650                 655

Met Arg Arg Ala Ala Lys Thr Ile Asn Phe Gly Val Leu Tyr Gly Met
                660                 665                 670

Ser Ala His Arg Leu Ser Gly Glu Leu Ser Ile Pro Tyr Glu Glu Ala
        675                 680                 685

Val Ala Phe Ile Glu Arg Tyr Phe Gln Ser Tyr Pro Lys Val Arg Ala
    690                 695                 700

Trp Ile Glu Gly Thr Leu Glu Glu Gly Arg Arg Arg Gly Tyr Val Glu
705                 710                 715                 720

Thr Leu Phe Gly Arg Arg Arg Tyr Val Pro Asp Leu Asn Ala Arg Val
                725                 730                 735

Lys Ser Val Arg Glu Ala Ala Glu Arg Met Ala Phe Asn Met Pro Val
                740                 745                 750

Gln Gly Thr Ala Ala Asp Leu Met Lys Leu Ala Met Val Arg Leu Phe
                755                 760                 765

Pro Arg Leu Gln Glu Leu Gly Ala Arg Met Leu Leu Gln Val His Asp
    770                 775                 780

Glu Leu Val Leu Glu Ala Pro Lys Asp Arg Ala Glu Arg Val Ala Ala
785                 790                 795                 800

Leu Ala Lys Glu Val Met Glu Gly Val Trp Pro Leu Gln Val Pro Leu
                805                 810                 815

Glu Val Glu Val Gly Leu Gly Glu Asp Trp Leu Ser Ala Lys Glu
                820                 825                 830
```